(12) United States Patent
Beaulieu et al.

(10) Patent No.: US 7,897,622 B2
(45) Date of Patent: Mar. 1, 2011

(54) VIRAL POLYMERASE INHIBITORS

(75) Inventors: Pierre Beaulieu, Rosemére (CA); René Coulombe, Montreal (CA); Gulrez Fazal, Roxboro (CA); Sylvie Goulet, Pierrefonds (CA); Martin Poirier, Blainville (CA); Jean Rancourt, Laval (CA); Tim Stammers, Rosemére (CA); Bounkham Thavonekham, Longueuil (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 538 days.

(21) Appl. No.: 11/837,202

(22) Filed: Aug. 10, 2007

(65) Prior Publication Data

US 2008/0045516 A1  Feb. 21, 2008

Related U.S. Application Data

(60) Provisional application No. 60/822,711, filed on Aug. 17, 2006.

(51) Int. Cl.
C07D 211/84 (2006.01)
A61K 31/44 (2006.01)

(52) U.S. Cl. ............ 514/336; 514/351; 546/268.1; 546/300

(58) Field of Classification Search .......... 546/268.1, 546/300; 514/336, 351
See application file for complete search history.

(56) References Cited

U.S. PATENT DOCUMENTS

| 7,112,600 B1 | 9/2006 | Hashimoto et al. |
| 2004/0082635 A1 | 4/2004 | Hashimoto et al. |

FOREIGN PATENT DOCUMENTS

| EP | 1 688 420 A1 | 8/2006 |
|---|---|---|
| WO | 99/07733 A2 | 2/1999 |
| WO | 99/07734 A2 | 2/1999 |
| WO | 00/09543 A2 | 2/2000 |
| WO | 00/09558 A1 | 2/2000 |
| WO | 00/59929 A1 | 10/2000 |
| WO | 01/47883 A1 | 7/2001 |
| WO | 01/77113 A2 | 10/2001 |
| WO | 01/81325 A2 | 11/2001 |
| WO | 02/04425 A2 | 1/2002 |
| WO | 02/08187 A1 | 1/2002 |
| WO | 02/08198 A2 | 1/2002 |
| WO | 02/08244 A2 | 1/2002 |
| WO | 02/08256 A2 | 1/2002 |
| WO | 02/48172 A2 | 6/2002 |
| WO | 02/060926 A2 | 8/2002 |
| WO | 03/000254 A1 | 1/2003 |
| WO | 03/004458 A1 | 1/2003 |
| WO | 03/007945 A1 | 1/2003 |
| WO | 03/010140 A2 | 2/2003 |
| WO | 03/010141 A2 | 2/2003 |
| WO | 03/026587 A2 | 4/2003 |
| WO | 03/053349 A2 | 7/2003 |
| WO | 03/062228 A1 | 7/2003 |
| WO | 03/062265 A2 | 7/2003 |
| WO | 03/064416 A1 | 8/2003 |
| WO | 03/064455 A2 | 8/2003 |
| WO | 03/064456 A1 | 8/2003 |
| WO | 03/093316 A1 | 12/2003 |
| WO | 03/099274 A1 | 12/2003 |
| WO | 03/101993 A1 | 12/2003 |
| WO | 2004/030670 A1 | 4/2004 |
| WO | 2004/032827 A2 | 4/2004 |
| WO | 2004/037855 A1 | 5/2004 |
| WO | 2004-039833 A1 | 5/2004 |
| WO | 2004/043339 A2 | 5/2004 |
| WO | 2004/064925 A1 | 8/2004 |
| WO | 2004/065367 A1 | 8/2004 |
| WO | 2004/072243 A2 | 8/2004 |
| WO | 2004/087714 A1 | 10/2004 |
| WO | 2004/093798 A2 | 11/2004 |
| WO | 2004/094452 A2 | 11/2004 |
| WO | 2004/101602 A2 | 11/2004 |
| WO | 2004/101605 A1 | 11/2004 |
| WO | 2004/103996 A1 | 12/2004 |
| WO | 2004/113365 A2 | 12/2004 |
| WO | 2005/010029 A1 | 2/2005 |
| WO | 2005/014543 A1 | 2/2005 |
| WO | 2205/012288 A1 | 2/2005 |
| WO | 2005/021584 A2 | 3/2005 |

(Continued)

OTHER PUBLICATIONS

A.F. Abdel-Magid, et al., "Reductive Amination of Aldehydes and Ketones with Sodium Triacetoxyborohydride. Studies on Direct and Indirect Reductive Amination Procedures", J. Org. Chem., 1996, vol. 61, p. 3849.
S. M. Berge, et al., "Pharmaceutical Salts", Journal of Pharmaceutical Sciences, 1977, vol. 66, No. 1, p. 1.
E. Buck, et al., "Preparation of 1-Methoxy-2-(4-Methoxyphenoxy) Benzene", Org. Syntheses, 2005, vol. 82, p. 69.
R. Hemalatha, et al., "QSAR Analysis of 5-substituted-2-Benzoylaminobenzoic acids as PPAR Modulator", E-Journal of Chemistry, 2004, vol. 1, No. 5, p. 243-250S.

(Continued)

*Primary Examiner*—Kahsay T Habte
(74) *Attorney, Agent, or Firm*—Michael P. Morris; David A. Dow

(57) ABSTRACT

Compounds of formula I:

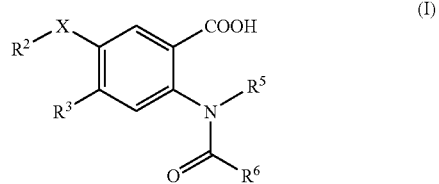

wherein X, $R^2$, $R^3$, $R^5$ and $R^6$ are defined herein, are useful as inhibitors of the hepatitis C virus NS5B polymerase.

22 Claims, No Drawings

FOREIGN PATENT DOCUMENTS

| WO | 2005/028501 A1 | 3/2005 |
|---|---|---|
| WO | 2005/030796 A1 | 4/2005 |
| WO | 2005/037214 A2 | 4/2005 |
| WO | 2005/046712 A1 | 5/2005 |
| WO | 2005/049622 A1 | 6/2005 |
| WO | 2005/051410 A1 | 6/2005 |
| WO | 2005/051980 A1 | 6/2005 |
| WO | 2005/054430 A2 | 6/2005 |
| WO | 2005/058821 A1 | 6/2005 |
| WO | 2005/070955 A1 | 8/2005 |
| WO | 2005/080388 A1 | 9/2005 |
| WO | 2005/085197 A1 | 9/2005 |
| WO | 2005/085242 A1 | 9/2005 |
| WO | 2005/085275 A1 | 9/2005 |
| WO | 2005/087721 A1 | 9/2005 |
| WO | 2005/087725 A2 | 9/2005 |
| WO | 2005/087730 A1 | 9/2005 |
| WO | 2005/087731 A1 | 9/2005 |
| WO | 2005/107745 A1 | 11/2005 |
| WO | 2005/113581 A1 | 12/2005 |
| WO | 2005/121132 A1 | 12/2005 |
| WO | 2006/000085 A1 | 1/2006 |
| WO | 2006/007693 A1 | 1/2006 |
| WO | 2006/007700 A1 | 1/2006 |
| WO | 2006/007708 A1 | 1/2006 |

OTHER PUBLICATIONS

E. J. Hennessy, et al., "A General and Mild Copper-Catalyzed Arylation of Diethyl Malonate", Organic Letters, 2002, vol. 4, No. 2, p. 269.

A. A. Kolykhalov, et al., "Hepatitis C Virus-Encoded Enzymatic Activities and Conserved RNA Elements in the 3' Nontranslated Region are Essential for Virus Replication in Vivo", J. Virology, 2000, vol. 74, No. 4, p. 2046.

G. McKercher, et al., "Specific inhibitors of HCV polymerase identified using an NS5B with lower affinity for template/primer substrate", Nucleic Acids Res., 2004, vol. 32, No. 2, p. 422.

T. Östberg, et al., "A New Class of Peroxisome Proliferator-activated Receptor Agonists with a novel Binding Epitope Shows Antidiabetic Effects", J. Biological Chemistry, 2004, vol. 279, No. 39, p. 41124.

W. C. Still, et al., "Rapid Chromatographic Technique for Preparative Separations with Moderate Resolution", J. Org. Chem., 1978, vol. 43, No. 14, p. 2923.

K. Takagi, "Synthesis of Aromatic Thiols from Aryl Iodides and Thiourea by Means of Nickel Catalyst", Chemistry Letters, 1985, p. 1307.

K. Tanaka, et al., "Synthesis and Reaction of 5-Amino-3-trifluoromethylisoxazole and—pyrazole-4-carboxylic Acids", J. Heterocyclic Chem., 1986, vol. 23, p. 1535.

M. Thor, et al., "Synthesis and Pharmacological Evaluation of a New Class of Peroxisome Proliferator-Activated Receptor Modulators", Bioorganic and Medicinal Chemistry Letters, 2002, vol. 12, p. 3565.

International Search Report PCT/CA2007/001363, Mailed Oct. 29, 2007.

SEQUENCE LISTING

<160> NUMBER OF SEQ ID NOS: 1

<210> SEQ ID NO 1
<211> LENGTH: 591
<212> TYPE: PRT
<213> ORGANISM: Artificial Sequence
<220> FEATURE:
<223> OTHER INFORMATION: HCV NS5B

<400> SEQUENCE: 1

```
Met Gly Ser Ser His His His His His His Ser Ser Gly Leu Val Pro
 1               5                  10                  15

Arg Gly Ser His Met Ser Met Ser Tyr Thr Trp Thr Gly Ala Leu Ile
            20                  25                  30

Thr Pro Cys Ala Ala Glu Glu Ser Gln Leu Pro Ile Asn Ala Leu Ser
        35                  40                  45

Asn Ser Leu Val Arg His Arg Asn Met Val Tyr Ser Thr Thr Ser Arg
    50                  55                  60

Ser Ala Ala Leu Arg Gln Lys Lys Val Thr Phe Asp Arg Leu Gln Val
65                  70                  75                  80

Leu Asp Asp His Tyr Arg Asp Val Leu Lys Glu Met Lys Ala Lys Ala
                85                  90                  95

Ser Thr Val Lys Ala Lys Leu Leu Ser Val Glu Glu Ala Cys Lys Leu
            100                 105                 110

Thr Pro Pro His Ser Ala Lys Ser Lys Phe Gly Tyr Gly Ala Lys Asp
        115                 120                 125

Val Arg Asn Leu Ser Ser Lys Ala Val Asp His Ile Arg Ser Val Trp
    130                 135                 140

Lys Asp Leu Leu Glu Asp Thr Glu Thr Pro Ile Asp Thr Thr Ile Met
145                 150                 155                 160

Ala Lys Asn Glu Val Phe Cys Val Gln Pro Glu Lys Gly Gly Arg Lys
                165                 170                 175

Pro Ala Arg Leu Ile Val Phe Pro Asp Leu Gly Val Arg Val Cys Glu
            180                 185                 190

Lys Met Ala Leu Tyr Asp Val Val Ser Thr Leu Pro Gln Ala Val Met
        195                 200                 205

Gly Ser Ser Tyr Gly Phe Gln Tyr Ser Pro Lys Gln Arg Val Glu Phe
    210                 215                 220

Leu Val Asn Ala Trp Lys Ser Lys Lys Cys Pro Met Gly Phe Ser Tyr
225                 230                 235                 240

Asp Thr Arg Cys Phe Asp Ser Thr Val Thr Glu Ser Asp Ile Arg Val
                245                 250                 255

Glu Glu Ser Ile Tyr Gln Cys Cys Asp Leu Ala Pro Glu Ala Arg Gln
            260                 265                 270

Ala Ile Lys Ser Leu Thr Glu Arg Leu Tyr Ile Gly Gly Pro Leu Thr
        275                 280                 285

Asn Ser Lys Gly Gln Asn Cys Gly Tyr Arg Arg Cys Arg Ala Ser Gly
    290                 295                 300

Val Leu Thr Thr Ser Cys Gly Asn Thr Leu Thr Cys Tyr Leu Lys Ala
305                 310                 315                 320

Ser Ala Ala Cys Arg Ala Ala Lys Leu Gln Asp Cys Thr Met Leu Val
                325                 330                 335

Asn Gly Asp Asp Leu Val Val Ile Cys Glu Ser Ala Gly Thr Gln Glu
            340                 345                 350
```

```
Asp Ala Ala Asn Leu Arg Val Phe Thr Glu Ala Met Thr Arg Tyr Ser
        355                 360                 365
Ala Pro Pro Gly Asp Leu Pro Gln Pro Glu Tyr Asp Leu Glu Leu Ile
    370                 375                 380
Thr Ser Cys Ser Ser Asn Val Ser Val Ala His Asp Ala Ser Gly Lys
385                 390                 395                 400
Arg Val Tyr Tyr Leu Thr Arg Asp Pro Thr Thr Pro Leu Ala Arg Ala
                405                 410                 415
Ala Trp Glu Thr Ala Arg His Thr Pro Ile Asn Ser Trp Leu Gly Asn
            420                 425                 430
Ile Ile Met Tyr Ala Pro Thr Leu Trp Ala Arg Met Val Leu Met Thr
        435                 440                 445
His Phe Phe Ser Ile Leu Leu Ala Gln Glu Gln Leu Glu Lys Ala Leu
    450                 455                 460
Asp Cys Gln Ile Tyr Gly Ala Cys Tyr Ser Ile Glu Pro Leu Asp Leu
465                 470                 475                 480
Pro Gln Ile Ile Glu Arg Leu His Gly Leu Ser Ala Phe Ser Leu His
                485                 490                 495
Ser Tyr Ser Pro Gly Glu Ile Asn Arg Val Ala Ser Cys Leu Arg Lys
            500                 505                 510
Leu Gly Val Pro Pro Leu Arg Val Trp Arg His Arg Ala Arg Ser Val
        515                 520                 525
Arg Ala Lys Leu Leu Ser Gln Gly Gly Arg Ala Ala Thr Cys Gly Lys
    530                 535                 540
Tyr Leu Phe Asn Trp Ala Val Arg Thr Lys Leu Lys Leu Thr Pro Ile
545                 550                 555                 560
Pro Ala Ala Ser Arg Leu Asp Leu Ser Gly Trp Phe Val Ala Gly Tyr
                565                 570                 575
Asn Gly Gly Asp Ile Tyr His Ser Leu Ser Arg Ala Arg Pro Arg
            580                 585                 590
```

VIRAL POLYMERASE INHIBITORS

RELATED APPLICATIONS

This application claims benefit of U.S. Ser. No. 60/822,711, filed Aug. 17, 2006, which is herein incorporated by reference.

FIELD OF THE INVENTION

The present invention relates to compounds, compositions and methods for the treatment of hepatitis C virus (HCV) infection. In particular, the present invention provides novel inhibitors of the hepatitis C virus NS5B polymerase, pharmaceutical compositions containing such compounds and methods for using these compounds in the treatment of HCV infection.

BACKGROUND OF THE INVENTION

It is estimated that at least 130 million persons worldwide are infected with the hepatitis C virus (HCV). Acute HCV infection progresses to chronic infection in a high number of cases, and, in some infected individuals, chronic infection leads to serious liver diseases such as cirrhosis and hepatocellular carcinoma.

Currently, standard treatment of chronic hepatitis C infection involves administration of pegylated interferon-alpha in combination with ribavirin. However, this therapy is not effective in reducing HCV RNA to undetectable levels in many infected patients and is associated with often intolerable side effects such as fever and other influenza-like symptoms, depression, thrombocytopenia and hemolytic anemia. Furthermore, some HCV-infected patients have co-existing conditions which contraindicate this treatment.

Therefore, a need exists for alternative treatments for hepatitis C viral infection. One possible strategy to address this need is the development of effective antiviral agents which inactivate viral or host cell factors which are essential for viral replication.

HCV is an enveloped positive strand RNA virus in the genus *Hepacivirus* in the Flaviviridae family. The single strand HCV RNA genome is approximately 9500 nucleotides in length and has a single open reading frame (ORF), flanked by 5' and 3' non-translated regions. The HCV 5' non-translated region is 341 nucleotides in length and functions as an internal ribosome entry site for cap-independent translation initiation. The open reading frame encodes a single large polyprotein of about 3000 amino acids which is cleaved at multiple sites by cellular and viral proteases to produce the mature structural and non-structural (NS2, NS3, NS4A, NS4B, NS5A, and NS5B) proteins. The viral NS2/3 protease cleaves at the NS2-NS3 junction; while the viral NS3 protease mediates the cleavages downstream of NS3, at the NS3-NS4A, NS4A-NS4B, NS4B-NS5A and NS5A-NS5B cleavage sites. The NS3 protein also exhibits nucleoside triphosphatase and RNA helicase activities. The NS4A protein acts as a cofactor for the NS3 protease and may also assist in the membrane localization of NS3 and other viral replicase components. Although NS4B and the NS5A phosphoprotein are also likely components of the replicase, their specific roles are unknown. The NS5B protein is the elongation subunit of the HCV replicase possessing RNA-dependent RNA polymerase (RdRp) activity.

The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics. It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046-2051).

WO 03/004458 describes compounds of the general formula:

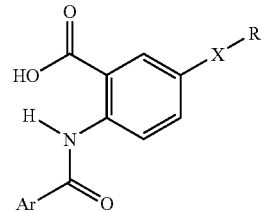

which modulate the activity of peroxisome proliferator-activated receptors α and/or γ. Similar compounds are described in Thor, M., et al, *Bioorganic & Medicinal Chemistry Letters* (2002) 12: 3565-3567; Östberg, T., et al, *Journal of Biological Chemistry* (2004) 279(39): 41124-41130; and Hemalatha, R., et al, *E-Journal of Chemistry* (2004) 1(5): 243-250 (abstracted in *Chemical Abstracts* 142: 190216).

SUMMARY OF THE INVENTION

The present invention provides a novel series of compounds having inhibitory activity against HCV polymerase. In particular compounds according to this invention inhibit RNA synthesis by the RNA dependent RNA polymerase of HCV, especially the enzyme NS5B encoded by HCV. A further advantage of compounds provided by this invention is their low to very low or even non-significant activity against other polymerases. Further objects of this invention arise for the one skilled in the art from the following description and the examples.

One aspect of the invention provides compounds of formula (I):

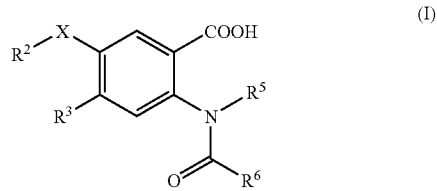

wherein:

X is selected from O and S;

$R^2$ is Het, optionally substituted with 1 to 5 $R^{20}$ substituents, wherein $R^{20}$ in each case is independently selected from:

a) halo, cyano or nitro;

b) $R^7$, —C(=O)—$R^7$, —C(=O)—O—$R^7$, —O—$R^7$, —S—$R^7$, —SO—$R^7$, —SO$_2$—$R^7$—($C_{1-6}$)alkylene-$R^7$, —($C_{1-6}$)alkylene-C(=O)—$R^7$, —($C_{1-6}$)alkylene-C(=O)—O—$R^7$, —($C_{1-6}$)alkylene-O—$R^7$, —($C_{1-6}$)alkylene-O—$R^7$, —($C_{1-6}$)alkylene-S—$R^7$, —($C_{1-6}$)alkylene-SO—$R^7$ or —($C_{1-6}$)alkylene-SO$_2$—$R^7$;

wherein $R^7$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; wherein the $(C_{1-6})$alkyl is optionally substituted with 1 or 2 substituents each independently selected from —OH, —O—$(C_{1-6})$alkyl, cyano, COOH, —NH$_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$; and wherein each of the aryl and Het is optionally substituted with 1 to 3 substituents each independently selected from:

i) halo, cyano, oxo, thioxo, imino, —OH, —O—$(C_{1-6})$alkyl, —O—$(C_{1-6})$haloalkyl, $(C_{3-7})$cycloalkyl, $(C_{1-6})$haloalkyl, —C(=O)—$(C_{1-6})$alkyl, —SO$_2(C_{1-6})$alkyl, —C(=O)—NH$_2$, —C(=O)—NH$(C_{1-4})$alkyl, —C(=O)—N$((C_{1-4})$alkyl$)_2$, —C(=O)—NH$(C_{3-7})$cycloalkyl, —C(=O)—N$((C_{1-4})$alkyl$)(C_{3-7})$cycloalkyl, —NH$_2$, —NH$(C_{1-4})$alkyl, —N$((C_{1-4})$alkyl$)_2$, —NH$(C_{3-7})$cycloalkyl, —N$((C_{1-4})$alkyl$)(C_{3-7})$cycloalkyl or —NH—C(=O)$(C_{1-4})$alkyl;

ii) $(C_{1-6})$alkyl optionally substituted with —OH, —O—$(C_{1-6})$haloalkyl, or —O—$(C_{1-6})$alkyl; and iii) aryl or Het, wherein each of the aryl and Het is optionally substituted with halo or $(C_{1-6})$alkyl; and c) —N(R$^8$)R$^9$, —C(=O)—N(R$^8$)R$^9$, —O—C(=O)—N(R$^8$)R$^9$, —SO$_2$—N(R$^8$)R$^9$, —$(C_{1-6})$alkylene-N(R$^8$)R$^9$, —$(C_{1-6})$alkylene-C(=O)—N(R$^8$)R$^9$, —$(C_{1-6})$alkylene-O—C(=O)—N(R$^8$)R$^9$, or —$(C_{1-6})$alkylene-SO$_2$—N(R$^8$)R$^9$ wherein R$^8$ is in each instance independently selected from H, $(C_{1-6})$alkyl and $(C_{3-7})$cycloalkyl; and R$^9$ is in each instance independently selected from R$^7$, —$(C_{1-6})$alkylene-R$^7$, —SO$_2$—R$^7$, —C(=O)—R$^7$, —C(=O)OR$^7$ and —C(=O)N(R$^8$)R$^7$; wherein R$^7$ and R$^8$ are as defined above;

R$^3$ is selected from H, halo, $(C_{1-4})$alkyl, —O—$(C_{1-4})$alkyl, —S—$(C_{1-4})$alkyl, —NH$_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$;

R$^5$ is H, $(C_{1-6})$alkyl, $(C_{3-7})$cycloalkyl or Het; the $(C_{1-6})$alkyl and Het each being optionally substituted with 1 to 4 substituents each independently selected from $(C_{1-6})$alkyl, Het, —OH, —COOH, —C(=O)—$(C_{1-6})$alkyl, —C(=O)—O—$(C_{1-6})$alkyl, —SO$_2(C_{1-6})$alkyl and —C(=O)—N(R$^{51}$)R$^{52}$;

wherein R$^{51}$ is H, $(C_{1-6})$alkyl or $(C_{3-7})$cycloalkyl; and

R$^{52}$ is H, $(C_{1-6})$alkyl, $(C_{3-7})$cycloalkyl, aryl, Het, aryl-$(C_{1-3})$alkyl- or Het-$(C_{1-3})$alkyl-; wherein each of the $(C_{1-6})$alkyl, $(C_{3-7})$cycloalkyl, aryl, Het, aryl-$(C_{1-3})$alkyl- and Het-$(C_{1-3})$alkyl- are optionally substituted with 1 to 3 substituents each independently selected from $(C_{1-6})$alkyl, $(C_{1-6})$haloalkyl, halo, oxo, —OH, —O$(C_{1-6})$alkyl, —NH$_2$, —NH$(C_{1-6})$alkyl, —N$((C_{1-6})$alkyl$)_2$, —NH$(C_{3-7})$cycloalkyl, —N$((C_{1-4})$alkyl$)(C_{3-7})$cycloalkyl, —C(=O)$(C_{1-6})$alkyl and —NHC(=O)—$(C_{1-6})$alkyl;

wherein the $(C_{1-6})$alkyl is optionally substituted with OH;

or R$^{51}$ and R$^{52}$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;

wherein the heterocycle is optionally substituted with 1 to 3 substituents each independently selected from $(C_{1-6})$alkyl, $(C_{1-6})$haloalkyl, halo, oxo, —OH, —O$(C_{1-6})$alkyl, —NH$_2$, —NH$(C_{1-6})$alkyl, —N$((C_{1-6})$alkyl$)_2$, —NH$(C_{3-7})$cycloalkyl, —N$((C_{1-4})$alkyl$)(C_{3-7})$cycloalkyl, —C(=O)$(C_{1-6})$alkyl and —NHC(=O)—$(C_{1-6})$alkyl;

wherein the $(C_{1-6})$alkyl is optionally substituted with OH;

R$^6$ is $(C_{3-7})$cycloalkyl or aryl;

the $(C_{3-7})$cycloalkyl and aryl each being optionally substituted with 1 to 5 substituents each independently selected from halo, $(C_{1-6})$alkyl, $(C_{1-6})$haloalkyl, $(C_{3-7})$cycloalkyl, —OH, —SH, —O—$(C_{1-4})$alkyl and —S—$(C_{1-4})$alkyl; and Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;

provided that when R$^2$ is selected from:

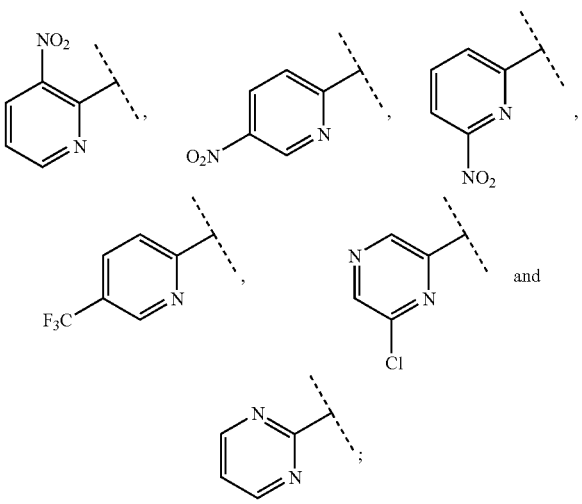

X is O; R$^3$ is H; and R$^5$ is H;
then R$^6$ is not

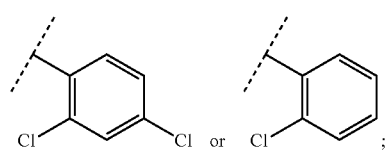

or a salt or ester thereof.

Another aspect of this invention provides a compound of formula (I), or a pharmaceutically acceptable salt or ester thereof, as a medicament.

Still another aspect of this invention provides a pharmaceutical composition comprising a therapeutically effective amount of a compound of formula (I) or a pharmaceutically acceptable salt or ester thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of a hepatitis C viral infection in a mammal having or at risk of having the infection.

A further aspect of the invention involves a method of treating a hepatitis C viral infection in a mammal having or at risk of having the infection, the method comprising administering to the mammal a therapeutically effective amount of a compound of formula (I), a pharmaceutically acceptable salt or ester thereof, or a composition thereof as described hereinabove.

Another aspect of the invention involves a method of treating a hepatitis C viral infection in a mammal having or at risk of having the infection, the method comprising administering to the mammal a therapeutically effective amount of a combination of a compound of formula (I) or a pharmaceutically acceptable salt or ester thereof, and at least one other antiviral agent; or a composition thereof.

Also within the scope of this invention is the use of a compound of formula (I) as described herein, or a pharmaceutically acceptable salt or ester thereof, for the treatment of a hepatitis C viral infection in a mammal having or at risk of having the infection.

Another aspect of this invention provides the use of a compound of formula (I) as described herein, or a pharmaceutically acceptable salt or ester thereof, for the manufacture of a medicament for the treatment of a hepatitis C viral infection in a mammal having or at risk of having the infection.

An additional aspect of this invention refers to an article of manufacture comprising a composition effective to treat a hepatitis C viral infection; and packaging material comprising a label which indicates that the composition can be used to treat infection by the hepatitis C virus; wherein the composition comprises a compound of formula (I) according to this invention or a pharmaceutically acceptable salt or ester thereof.

Still another aspect of this invention relates to a method of inhibiting the replication of hepatitis C virus comprising exposing the virus to an effective amount of the compound of formula (I), or a salt or ester thereof, under conditions where replication of hepatitis C virus is inhibited.

Further included in the scope of the invention is the use of a compound of formula (I), or a salt or ester thereof, to inhibit the replication of hepatitis C virus.

DETAILED DESCRIPTION OF THE INVENTION

Definitions

As used herein, the following definitions apply unless otherwise noted:

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "$(C_{1-n})$alkyl" as used herein, wherein n is an integer, either alone or in combination with another radical, is intended to mean acyclic, straight or branched chain alkyl radicals containing from 1 to n carbon atoms. "$(C_{1-6})$alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "$(C_{1-n})$alkylene" as used herein, wherein n is an integer, either alone or in combination with another radical, is intended to mean acyclic, straight or branched chain divalent alkyl radicals containing from 1 to n carbon atoms. "$(C_{1-6})$alkylene" includes, but is not limited to,

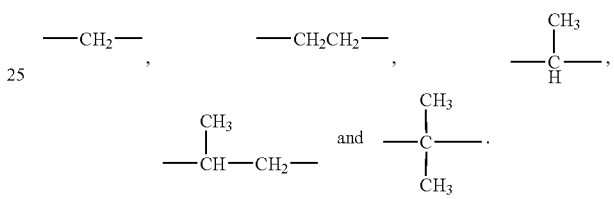

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$ alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{3-m})$cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl.

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of $(C_{3-7})$cycloalkyl-$(C_{1-6})$alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-n})$alkyl- include, but are not limited to, phenylmethyl (benzyl), 1-phenylethyl, 2-phenylethyl and phenylpropyl. When an aryl-$(C_{1-n})$alkyl- group is substituted, it is understood that substituents may be attached to either the aryl or the alkyl portion thereof or both, unless specified otherwise.

The term "Het" as used herein, either alone or in combination with another radical, is intended to mean a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$, unless specified otherwise. When a Het group is substituted, it is understood that substituents may be attached to any carbon atom or heteroatom thereof which would otherwise bear a hydrogen atom, unless specified otherwise.

The term "Het-$(C_{1-n})$alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-$(C_{1-n})$alkyl- include, but are not limited to, thienylmethyl, furylmethyl, piperidinylethyl, 2-pyridinylmethyl, 3-pyridinylmethyl, 4-pyridinylmethyl, quinolinylpropyl, and the like. When a Het-$(C_{1-n})$alkyl- group is substituted, it is understood that substituents may be attached to either the Het or the alkyl portion thereof or both, unless specified otherwise.

The term "heteroatom" as used herein is intended to mean O, S or N.

The term "heterocycle" as used herein and unless specified otherwise, either alone or in combination with another radical, is intended to mean a 4- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine, pyrimidine, and the following heterocycles:

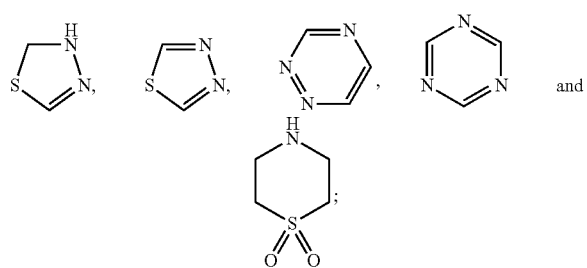

and saturated, unsaturated and aromatic derivatives thereof.

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, isoindole, benzimidazole, benzothiophene, benzofuran, benzodioxole, benzothiazole, quinoline, isoquinoline, naphthyridine, and the following heteropolycycles:

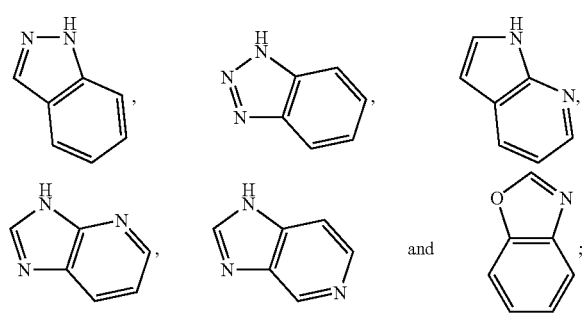

and saturated, unsaturated and aromatic derivatives thereof.

The term "halo" as used herein is intended to mean a halogen substituent selected from fluoro, chloro, bromo or iodo.

The term "$(C_{1-n})$haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of $(C_{1-n})$haloalkyl include but are not limited to chloromethyl, chloroethyl, dichloroethyl, bromomethyl, bromoethyl, dibromoethyl, fluoromethyl, difluoromethyl, trifluoromethyl, fluoroethyl and difluoroethyl.

The terms "—O—$(C_{1-n})$alkyl" or "$(C_{1-n})$alkoxy" as used herein interchangeably, wherein n is an integer, either alone or in combination with another radical, is intended to mean an oxygen atom further bonded to an alkyl radical having 1 to n carbon atoms as defined above. Examples of —O—($C_{1-n}$) alkyl include but are not limited to methoxy ($CH_3O$—), ethoxy ($CH_3CH_2O$—), propoxy ($CH_3CH_2CH_2O$—), 1-methylethoxy (iso-propoxy; $(CH_3)_2CH$—O—) and 1,1-dimethylethoxy (tert-butoxy; $(CH_3)_3C$—O—). When an —O—($C_{1-n}$)alkyl radical is substituted, it is understood to be substituted on the ($C_{1-n}$)alkyl portion thereof.

The terms "—S—($C_{1-n}$)alkyl" or "($C_{1-n}$)alkylthio" as used herein interchangeably, wherein n is an integer, either alone or in combination with another radical, is intended to mean an sulfur atom further bonded to an alkyl radical having 1 to n carbon atoms as defined above. Examples of —S—($C_{1-n}$) alkyl include but are not limited to methylthio ($CH_3S$—), ethylthio ($CH_3CH_2S$—), propylthio ($CH_3CH_2CH_2S$—), 1-methylethylthio (isopropylthio; $(CH_3)_2CH$—S—) and 1,1-dimethylethylthio (tert-butylthio; $(CH_3)_3C$—S—). When —S—($C_{1-n}$)alkyl radical, or an oxidized derivative thereof, such as an —SO—($C_{1-n}$)alkyl radical or an —$SO_2$—($C_{1-n}$) alkyl radical, is substituted, each is understood to be substituted on the ($C_{1-n}$)alkyl portion thereof.

The term "oxo" as used herein is intended to mean an oxygen atom attached to a carbon atom as a substituent by a double bond (=O).

The term "thioxo" as used herein is intended to mean a sulfur atom attached to a carbon atom as a substituent by a double bond (=S).

The term "imino" as used herein is intended to mean a NH group attached to a carbon atom as a substituent by a double bond (=NH).

The term "COOH" as used herein is intended to mean a carboxyl group (—C(=O)—OH). It is well known to one skilled in the art that carboxyl groups may be substituted by functional group equivalents. Examples of such functional group equivalents contemplated in this invention include, but are not limited to, esters, amides, imides, boronic acids, phosphonic acids, phosphoric acids, tetrazoles, triazoles, N-acylsulfamides ($RCONHSO_2NR_2$), and N-acylsulfonamides ($RCONHSO_2R$).

The term "functional group equivalent" as used herein is intended to mean an atom or group that may replace another atom or group which has similar electronic, hybridization or bonding properties.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof, herein incorporated by reference.

The following designation ⊤ is used in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Birge et al., J. Pharm. Sci., 1977, 66, pp. 1-19, herein incorporated by reference.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "ester thereof" as used herein is intended to mean any ester of a compound according to the invention in which any of the —COOH substituents of the molecule is replaced by a —COOR substituent, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl, each of which being optionally further substituted. The term "ester thereof" includes but is not limited to pharmaceutically acceptable esters thereof.

The term "pharmaceutically acceptable ester" as used herein is intended to mean esters of the compound according to the invention in which any of the COOH substituents of the molecule are replaced by a —COOR substituent, in which the R moiety of the ester is selected from alkyl (including, but not limited to, methyl, ethyl, propyl, 1-methylethyl, 1,1-dimethylethyl, butyl); alkoxyalkyl (including, but not limited to methoxymethyl); acyloxyalkyl (including, but not limited to acetoxymethyl); arylalkyl (including, but not limited to, benzyl); aryloxyalkyl (including, but not limited to, phenoxymethyl); and aryl (including, but not limited to phenyl) optionally substituted with halogen, $(C_{1-4})$alkyl or $(C_{1-4})$alkoxy. Other suitable esters can be found in Design of Prodrugs, Bundgaard, H. Ed. Elsevier (1985), herein incorporated by reference. Such pharmaceutically acceptable esters are usually hydrolyzed in vivo when injected into a mammal and transformed into the acid form of the compound according to the invention. With regard to the esters described above, unless otherwise specified, any alkyl moiety present preferably contains 1 to 16 carbon atoms, more preferably 1 to 6 carbon atoms. Any aryl moiety present in such esters preferably comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "mammal" as used herein is intended to encompass humans, as well as non-human mammals which are susceptible to infection by hepatitis C virus. Non-human mammals include but are not limited to domestic animals, such as cows, pigs, horses, dogs, cats, rabbits, rats and mice, and non-domestic animals.

The term "treatment" as used herein is intended to mean the administration of a compound or composition according to the present invention to alleviate or eliminate symptoms of the hepatitis C disease and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

The term "antiviral agent" as used herein is intended to mean an agent that is effective to inhibit the formation and/or replication of a virus in a mammal, including but not limited to agents that interfere with either host or viral mechanisms necessary for the formation and/or replication of a virus in a mammal.

PREFERRED EMBODIMENTS

In the following preferred embodiments, groups and substituents of the compounds according to this invention are described in detail.

X:

X-A: In one embodiment, X is O.

X-B: In another embodiment, X is S.

Any and each individual definition of X as set out herein may be combined with any and each individual definition of $R^2$, $R^3$, $R^5$ and $R^6$ as set out herein.

$R^2$:

Het-A: In one embodiment, $R^2$ is Het wherein Het is a 5- or 6-membered heterocycle containing 1 to 3 heteroatoms each independently selected from O, N and S, or a 9- or 10-membered bicyclic heteropolycycle containing 1 to 3 heteroatoms each independently selected from O, N and S; wherein Het is optionally substituted with 1 to 5 $R^{20}$ substituents, wherein $R^{20}$ is as defined herein.

Het-B: In another embodiment, $R^2$ is Het wherein Het is a 5- or 6-membered aromatic heterocycle containing 1 or 2 N heteroatoms, or a 9- or 10-membered bicyclic heteropolycycle containing 1 or 2 N heteroatoms; wherein Het is optionally substituted with 1 to 3 $R^{20}$ substituents, wherein $R^{20}$ is as defined herein.

Het-C: In another embodiment, $R^2$ is Het selected from the following formulas:

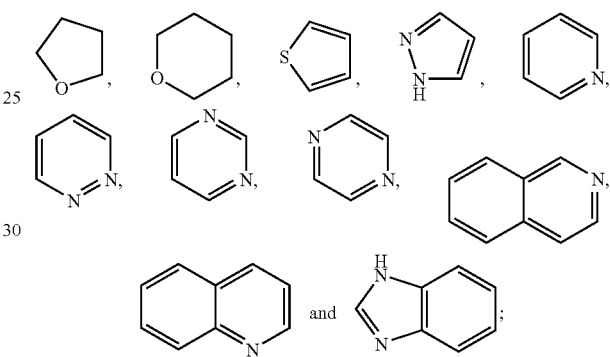

wherein Het is optionally substituted with 1 to 3 $R^{20}$ substituents, wherein $R^{20}$ is as defined herein.

Het-D: In another embodiment, $R^2$ is Het of the formula:

wherein Het is optionally substituted with 1 to 3 $R^{20}$ substituents, wherein $R^{20}$ is as defined herein.

Het-E: In another embodiment, $R^2$ is a group of the formula:

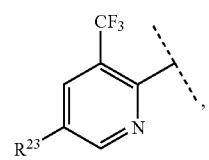

wherein $R^{23}$ is $R^{20}$ as defined herein.

$R^{20}$-A: In one embodiment, $R^{20}$ is selected from:

a) halo, cyano or nitro;

b) $R^7$, $-(C_{1-6})$alkylene-$R^7$, $-C(=O)-R^7$, $-O-R^7$, $-C(=O)-O-R^7$, $-(C_{1-6})$alkylene-$O-R^7$, $-S-R^7$, $-SO_2-R^7$, $-(C_{1-6})$alkylene-S-$R^7$ or $-(C_{1-6})$alkylene-$SO_2-R^7$;

wherein $R^7$ is in each instance independently selected from H, $(C_{1-6})$alkyl, $(C_{2-6})$alkenyl, $(C_{1-6})$haloalkyl, ($C_{3-7}$)cycloalkyl, aryl and Het; wherein the Het is a 5- or 6-membered heterocycle containing 1 to 4 heteroatoms, each independently selected from N, O and S, or Het is a 9- or 10-membered heteropolycycle containing 1 to 4 heteroatoms, each independently selected from N, O and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$; and wherein the ($C_{1-6}$)alkyl is optionally substituted with 1 or 2 substituents each independently selected from —OH, —O—($C_{1-6}$)alkyl and COOH; and wherein each of the aryl and Het is optionally substituted with 1 to 3 substituents each independently selected from halo, cyano, oxo, imino, —OH, —O—($C_{1-6}$)alkyl, —$NH_2$, —NH($C_{1-4}$)alkyl, —N(($C_{1-4}$)alkyl)$_2$, —NH—C(=O)($C_{1-4}$)alkyl, ($C_{1-6}$)alkyl and Het, wherein the Het is a 5- or 6-membered heterocycle containing 1 to 4 heteroatoms, each independently selected from N, O and S; and c) —N($R^8$)$R^9$, —($C_{1-6}$)alkylene-N($R^8$)$R^9$ or —($C_{1-6}$)alkylene-C(=O)—N($R^8$)$R^9$ wherein $R^8$ is in each instance independently selected from H and ($C_{1-6}$)alkyl; and $R^9$ is in each instance independently selected from $R^7$, —$SO_2$—$R^7$, —C(=O)—$R^7$, —C(=O)O$R^7$ and —C(=O)N($R^8$)$R^7$; wherein $R^7$ and $R^8$ are as defined above.

$R^{20}$-B: In another embodiment, $R^{20}$ is selected from:
a) halo or cyano;
b) $R^7$, —($C_{1-6}$)alkylene-$R^7$, —C(=O)—$R^7$, —($C_{1-6}$)alkylene-O—$R^7$, —$SO_2$—$R^7$, —($C_{1-6}$)alkylene-S—$R^7$ or —($C_{1-6}$)alkylene-$SO_2$—$R^7$;

wherein $R^7$ is in each instance independently selected from H, ($C_{1-6}$)alkyl, ($C_{2-6}$)alkenyl, ($C_{1-6}$)haloalkyl, ($C_{3-7}$)cycloalkyl, aryl and Het; wherein the Het is a 5- or 6-membered heterocycle containing 1 to 4 heteroatoms, each independently selected from N, O and S, or Het is a 9- or 10-membered heteropolycycle containing 1 to 4 heteroatoms, each independently selected from N, O and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$; and wherein the ($C_{1-6}$)alkyl is optionally substituted with 1 or 2 substituents each independently selected from —OH, —O—($C_{1-6}$)alkyl and COOH; and wherein each of the aryl and Het is optionally substituted with 1 to 3 substituents each independently selected from halo, cyano, oxo, imino, —OH, —O—($C_{1-6}$)alkyl, —$NH_2$, —NH($C_{1-4}$)alkyl, —N(($C_{1-4}$)alkyl)$_2$, —NH—C(=O)($C_{1-4}$)alkyl, ($C_{1-6}$)alkyl and Het, wherein the Het is a 5- or 6-membered heterocycle containing 1 to 4 heteroatoms, each independently selected from N, O and S; and c) —($C_{1-6}$)alkylene-N($R^8$)$R^9$ or —($C_{1-6}$)alkylene-C(=O)—N($R^8$)$R^9$ wherein $R^8$ is in each instance independently selected from H and ($C_{1-6}$)alkyl; and $R^9$ is in each instance independently selected from $R^7$, —$SO_2$—$R^7$, —C(=O)—$R^7$, —C(=O)O$R^7$ and —C(=O)N($R^8$)$R^7$; wherein $R^7$ and $R^8$ are as defined above.

$R^{20}$-C: In another embodiment, $R^{20}$ is selected from:
a) halo or cyano;
b) $R^7$, —$CH_2$—$R^7$, —C(=O)—$R^7$, —$CH_2$—O—$R^7$, —$SO_2$—$R^7$, —$CH_2$—S—$R^7$ or —$CH_2$—$SO_2$—$R^7$; wherein $R^7$ is in each instance independently selected from H, ($C_{1-6}$)alkyl, ($C_{2-6}$)alkenyl, ($C_{1-6}$)haloalkyl, ($C_{3-7}$)cycloalkyl, phenyl and Het; wherein the Het is selected from:

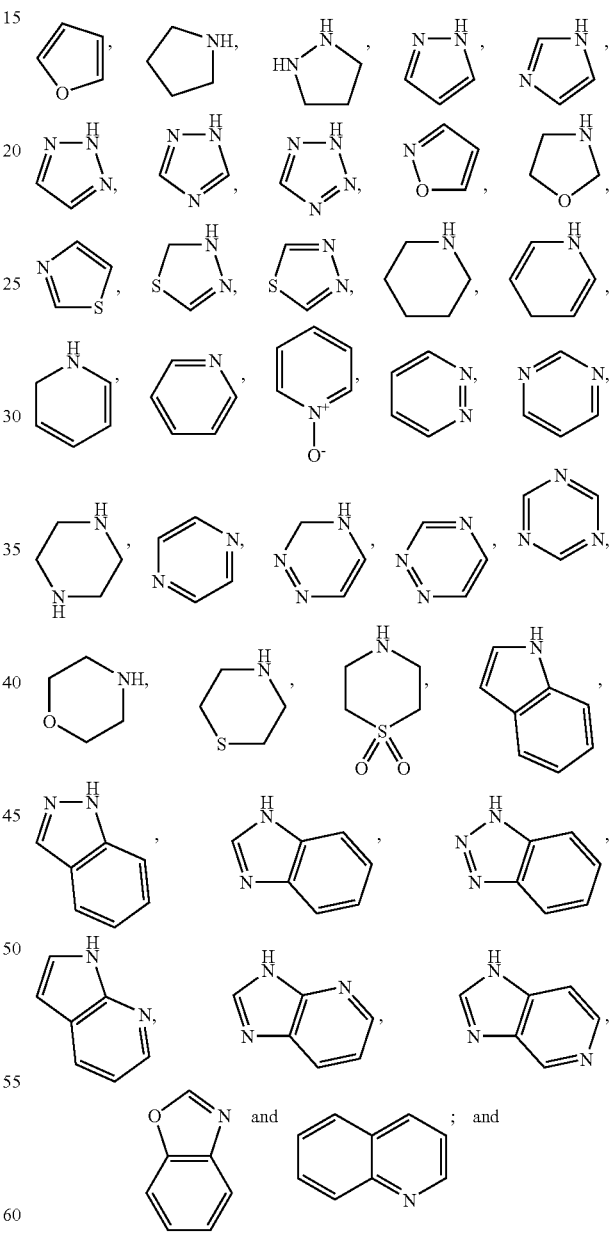

wherein the ($C_{1-6}$)alkyl is optionally substituted with 1 or 2 substituents each independently selected from —OH, —O—($C_{1-6}$)alkyl and COOH; and wherein each of the phenyl and Het is optionally substituted with 1 to 3 substituents each independently selected from halo, cyano, oxo, imino, —OH, —O—(C$_{1-6}$)alkyl, —NH$_2$, —NH(C$_{1-4}$)alkyl, —N((C$_{1-4}$)alkyl)$_2$, —NH—C(=O)(C$_{1-4}$)alkyl, (C$_{1-6}$)alkyl and

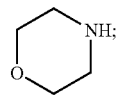

and c) —CH$_2$—N(R$^8$)R$^9$ or —CH$_2$—C(=O)—N(R$^8$)R$^9$ wherein
R$^8$ is in each instance independently selected from H and (C$_{1-6}$)alkyl; and
R$^9$ is in each instance independently selected from R$^7$, —SO$_2$—R$^7$, —C(=O)—R$^7$, —C(=O)OR$^7$ and —C(=O)N(R$^8$)R$^7$; wherein R$^7$ and R$^8$ are as defined above.

R$^{20}$-D: In another embodiment, R$^{20}$ is selected from:
b) —(C$_{1-3}$)alkylene-R$^7$, —(C$_{1-3}$)alkylene-O—R$^7$, —(C$_{1-3}$)alkylene-S—R$^7$ or —(C$_{1-3}$)alkylene-SO$_2$—R$^7$;
wherein R$^7$ is Het; wherein the Het is a 5- or 6-membered heterocycle containing 1 to 4 heteroatoms, each independently selected from N, O and S, or Het is a 9- or 10-membered heteropolycycle containing 1 to 4 heteroatoms, each independently selected from N, O and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;
wherein the Het is optionally substituted with 1 to 3 substituents each independently selected from halo, cyano, oxo, imino, —OH, —O—(C$_{1-6}$)alkyl, —O—(C$_{1-6}$)haloalkyl, (C$_{3-7}$)cycloalkyl, —NH$_2$, —NH(C$_{1-4}$)alkyl, —NH(C$_{3-7}$)cycloalkyl, —N((C$_{1-4}$)alkyl)(C$_{3-7}$)cycloalkyl, —N((C$_{1-4}$)alkyl)$_2$, —NH—C(=O)(C$_{1-4}$)alkyl, (C$_{1-6}$)alkyl and Het, wherein the Het is a 5- or 6-membered heterocycle containing 1 to 4 heteroatoms, each independently selected from N, O and S; and c) —(C$_{1-3}$)alkylene-N(R$^8$)R$^9$ wherein
R$^8$ is in each instance independently selected from H, (C$_{1-6}$)alkyl and (C$_{3-7}$)cycloalkyl; and
R$^9$ is R$^7$ wherein R$^7$ is as defined above.

R$^{20}$-E: In another embodiment, R$^{20}$ is selected from:
b) —CH$_2$—R$^7$, —CH$_2$CH$_2$—R$^7$, —CH$_2$—O—R$^7$, —CH$_2$—S—R$^7$ or —CH$_2$—SO$_2$—R$^7$;
wherein R$^7$ is Het; wherein the Het is selected from:

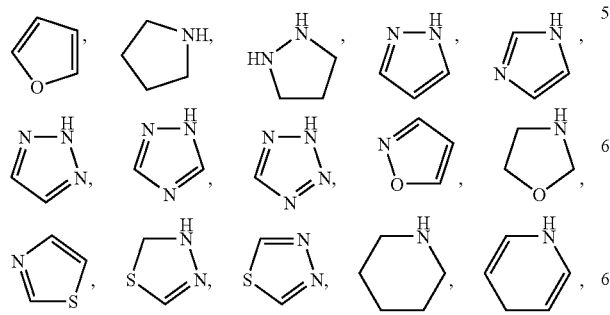

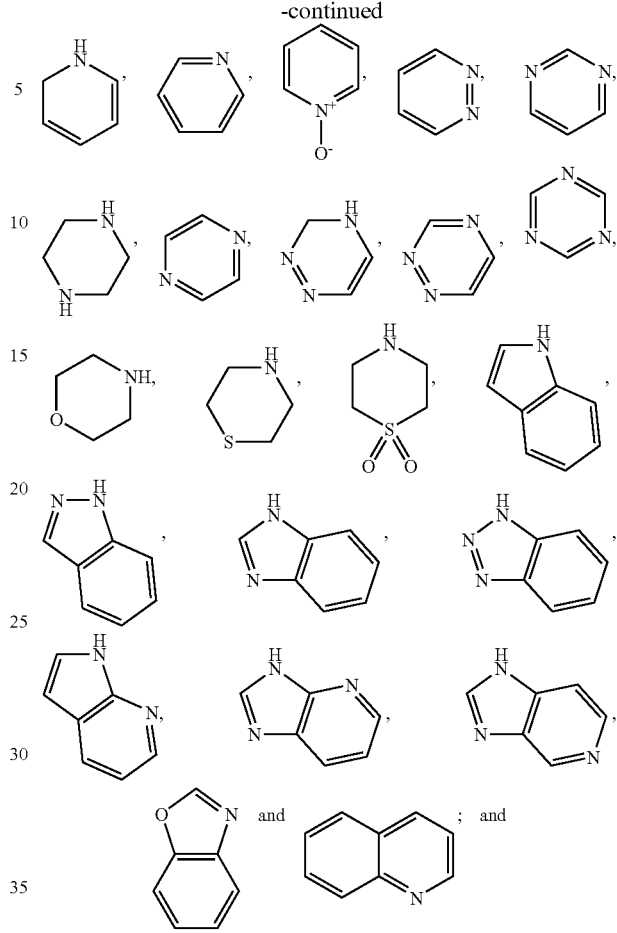

wherein the Het is optionally substituted with 1 to 3 substituents each independently selected from halo, cyano, oxo, imino, —OH, —O—(C$_{1-6}$)alkyl, —NH$_2$, —NH(C$_{1-4}$)alkyl, —N((C$_{1-4}$)alkyl)$_2$, —NH—C(=O)(C$_{1-4}$)alkyl, (C$_{1-6}$)alkyl and

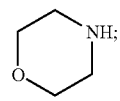

and c) —CH$_2$—N(R$^8$)R$^9$ wherein
R$^8$ is in each instance independently selected from H and (C$_{1-6}$)alkyl; and
R$^9$ is R$^7$ wherein R$^7$ is as defined above.

Therefore, examples of embodiments of R$^2$ are set forth in the following table, wherein each substituent group is defined according to the definitions set forth above:

| Embodiment | Het | R$^{20}$ |
|---|---|---|
| R$^2$-A | Het-A | R$^{20}$-A |
| R$^2$-B | Het-B | R$^{20}$-A |
| R$^2$-C | Het-C | R$^{20}$-A |
| R$^2$-D | Het-D | R$^{20}$-A |

| Embodiment | Het | R²⁰ |
|---|---|---|
| R²-E | Het-E | R²⁰-A |
| R²-F | Het-E | R²⁰-B |
| R²-G | Het-E | R²⁰-C |
| R²-H | Het-E | R²⁰-D |
| R²-I | Het-E | R²⁰-E |
R²-J: In another embodiment, R² is selected from:
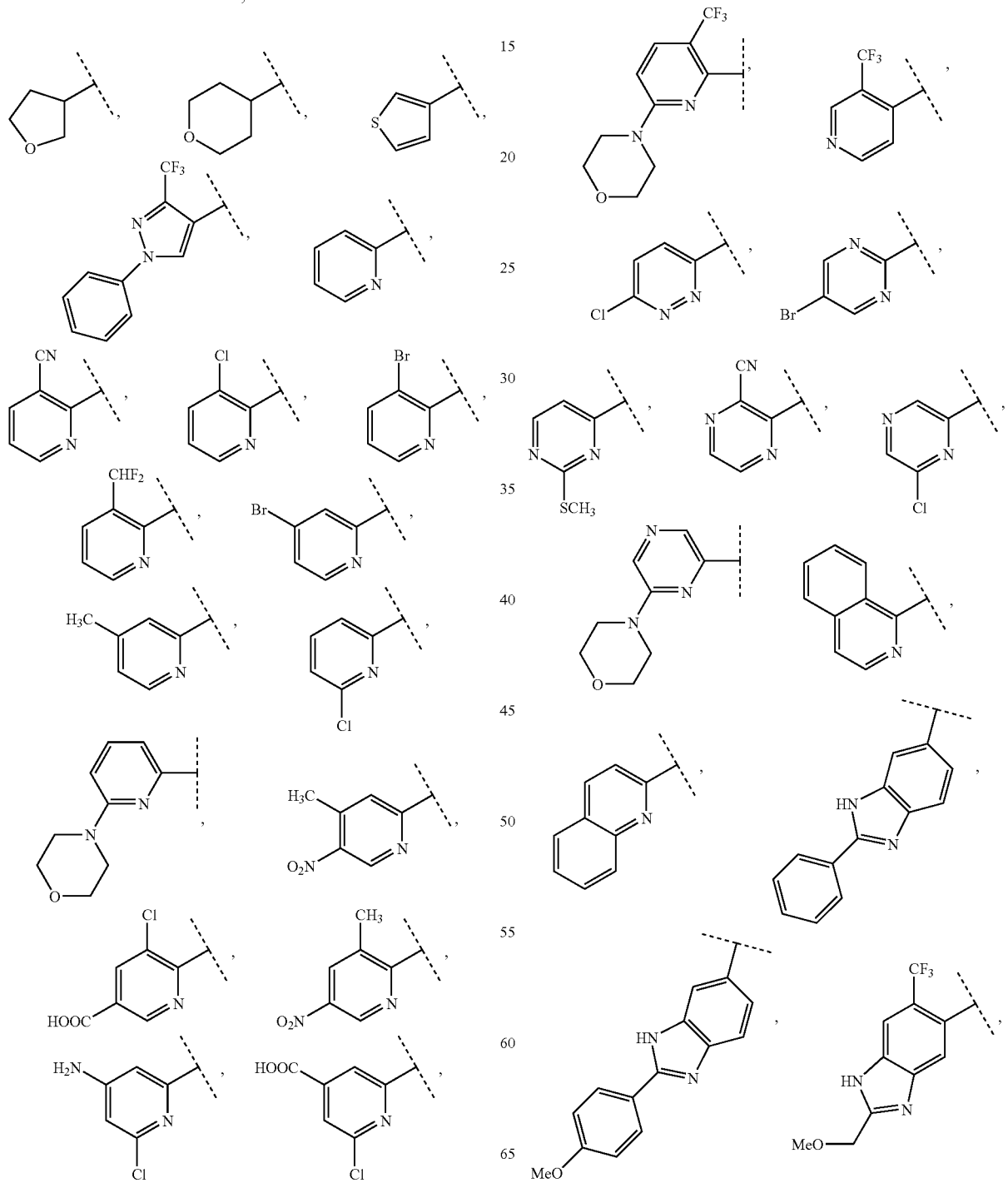

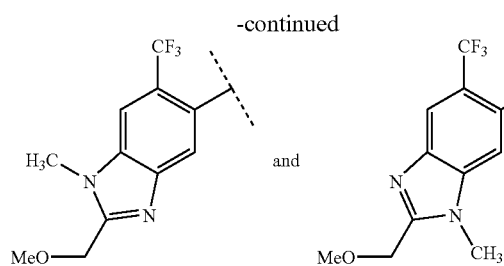
or R² is a group of the formula:
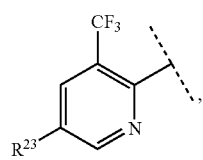
wherein R²³ is selected from:
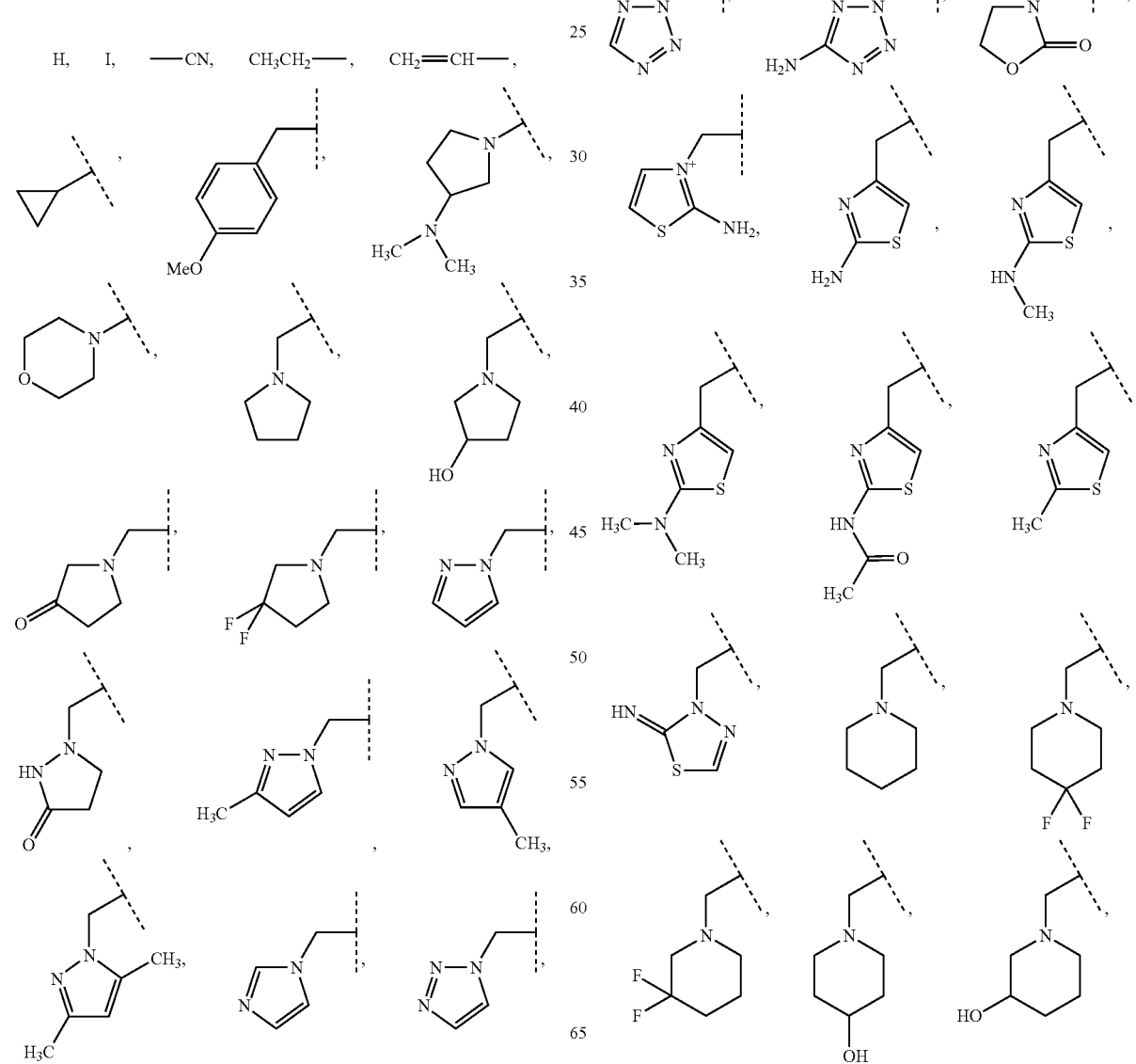

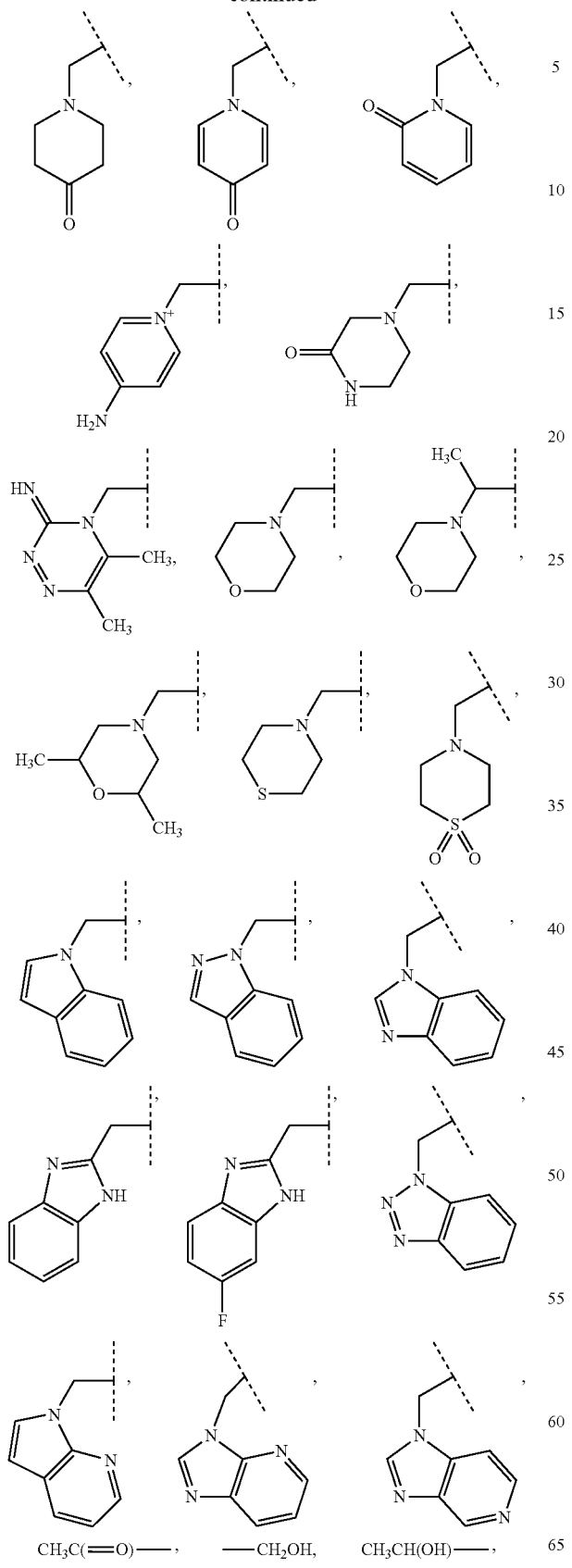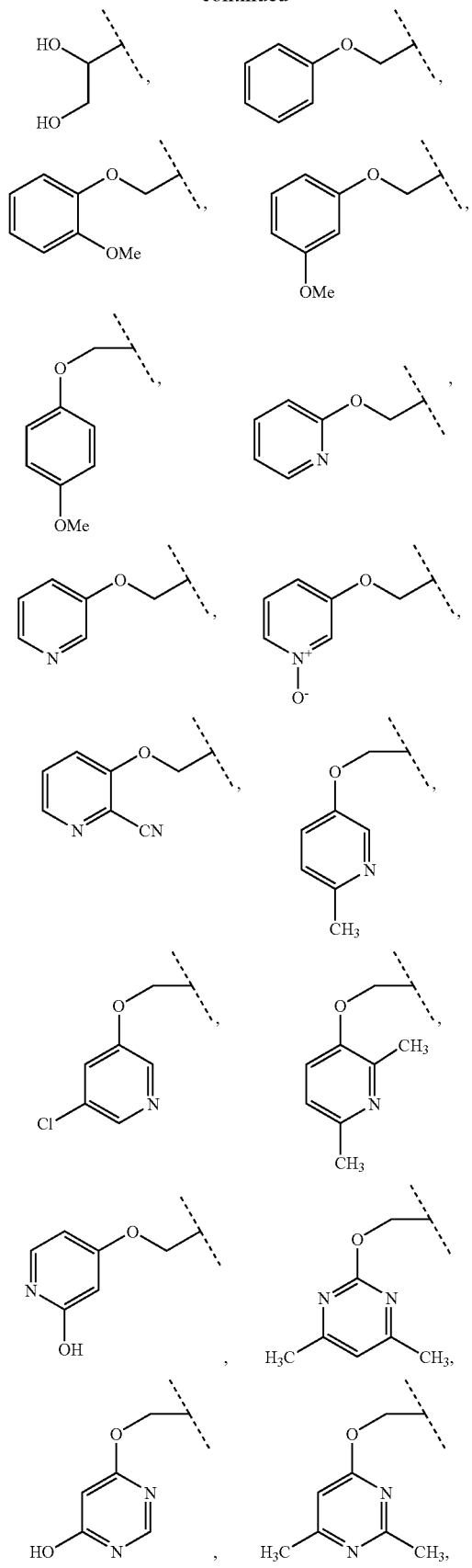

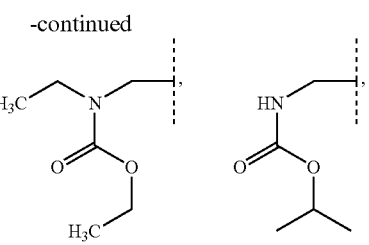
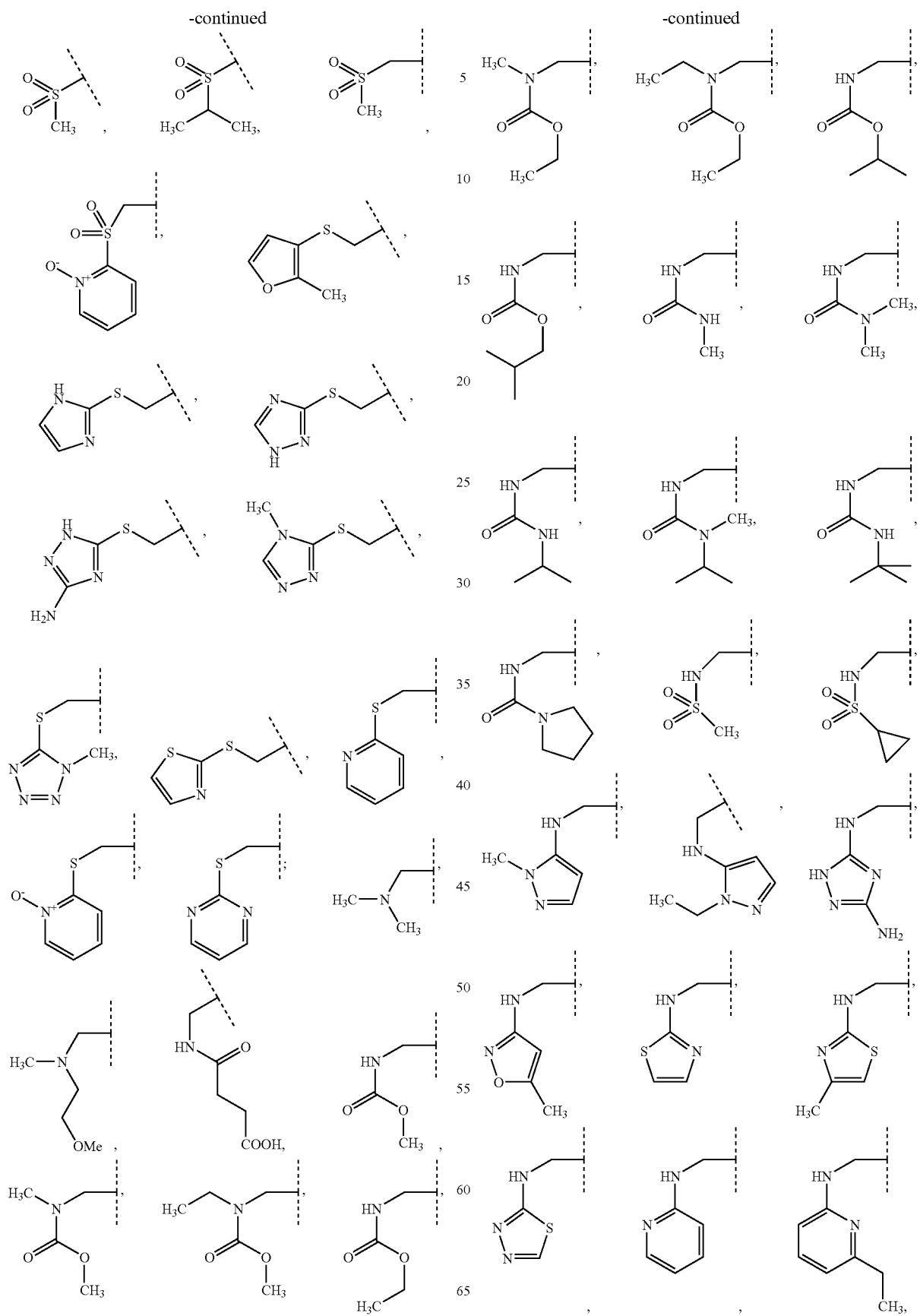

Any and each individual definition of $R^2$ as set out herein may be combined with any and each individual definition of X, $R^3$, $R^5$ and $R^6$ as set out herein.

$R^3$:
$R^3$-A: In one embodiment, $R^3$ is selected from H, halo, $(C_{1-4})$alkyl, —O—$(C_{1-4})$alkyl and —N$((C_{1-4})$alkyl$)_2$.
$R^3$-B: In another embodiment, $R^3$ is selected from H and halo.
$R^3$-C: In another embodiment, $R^3$ is H or F.
$R^3$-D: In another embodiment, $R^3$ is H.

Any and each individual definition of $R^3$ as set out herein may be combined with any and each individual definition of X, $R^2$, $R^5$ and $R^6$ as set out herein.

$R^5$:
$R^5$-A: In one embodiment, $R^5$ is $(C_{1-6})$alkyl.
$R^5$-B: In another embodiment, $R^5$ is methyl or 1-methylethyl.
$R^5$-C: In another embodiment, $R^5$ is 1-methylethyl.
$R^5$-D: In another embodiment, $R^5$ is $(C_{1-4})$alkyl substituted with Het, —COOH or —C(=O)—N$(R^{51})R^{52}$, wherein the Het is a 5- or 6-membered heterocycle containing from 1 to 4 N heteroatoms or Het is a 9- or 10-membered bicyclic heteropolycycle containing from 1 to 4 N heteroatoms;
and wherein $R^{51}$ is H or $(C_{1-6})$alkyl and $R^{52}$ is selected from H, $(C_{1-6})$alkyl, $(C_{3-7})$cycloalkyl, Het and Het-$(C_{1-3})$alkyl-;
wherein the $(C_{1-6})$alkyl is optionally substituted with 1 or 2 substituents each independently selected from —O$(C_{1-6})$alkyl and —N$((C_{1-6})$alkyl$)_2$; and wherein the Het and the Het portion of Het-$(C_{1-3})$alkyl- are each independently a 5- or 6-membered heterocycle containing 1 to 3 heteroatoms each independently selected from N, O and S, wherein the Het and the Het-$(C_{1-3})$alkyl- are each optionally substituted with 1 to 3 substituents each independently selected from halo, oxo, —OH, $(C_{1-6})$alkyl, $(C_{1-6})$haloalkyl, —(C=O)$(C_{1-6})$alkyl, —N$((C_{1-6})$alkyl$)_2$ and —NH(C=O)$(C_{1-6})$alkyl,
wherein the $(C_{1-6})$alkyl is optionally substituted with OH;
or $R^{51}$ and $R^{52}$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or $SO_2$;
wherein the heterocycle is optionally substituted with 1 to 3 substituents each independently selected from halo, oxo, —OH, $(C_{1-6})$alkyl, $(C_{1-6})$haloalkyl, —(C=O)$(C_{1-6})$alkyl, —N$((C_{1-6})$alkyl$)_2$ and —NH(C=O)$(C_{1-6})$alkyl,
wherein the $(C_{1-6})$alkyl is optionally substituted with OH.

$R^5$-E: In another embodiment, $R^5$ is $(C_{1-2})$alkyl substituted with Het, —COOH or —C(=O)—N($R^{51}$)$R^{52}$, wherein the Het is selected from

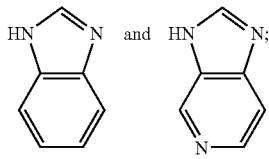

and wherein $R^{51}$ is H or $(C_{1-6})$alkyl and $R^{52}$ is selected from H, $(C_{1-4})$alkyl, $(C_{3-6})$cycloalkyl, Het and Het-$(C_{1-3})$alkyl-;
wherein the $(C_{1-6})$alkyl is optionally substituted with 1 or 2 substituents each independently selected from —O$(C_{1-4})$alkyl and —N$((C_{1-4})$alkyl$)_2$; and wherein the Het and the Het portion of Het-$(C_{1-3})$alkyl- are each independently selected from:

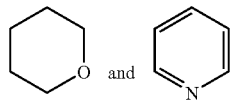

wherein the Het and the Het-$(C_{1-3})$alkyl- are each optionally substituted with 1 to 3 substituents each independently selected from halo, oxo, —OH, $(C_{1-6})$alkyl, $(C_{1-6})$haloalkyl, —(C=O)$(C_{1-6})$alkyl, —N$((C_{1-6})$alkyl$)_2$ and —NH(C=O)$(C_{1-6})$alkyl,
wherein the $(C_{1-6})$alkyl is optionally substituted with OH;
or $R^{51}$ and $R^{52}$, together with the N to which they are attached, are linked to form a heterocycle selected from:

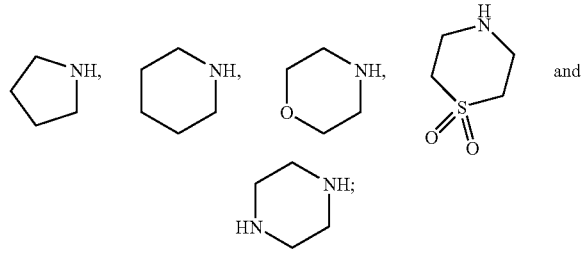

wherein the heterocycle is optionally substituted with 1 to 3 substituents each independently selected from halo, oxo, —OH, $(C_{1-6})$alkyl, $(C_{1-6})$haloalkyl, —(C=O)$(C_{1-6})$alkyl, —N$((C_{1-6})$alkyl$)_2$ and —NH(C=O)$(C_{1-6})$alkyl,
wherein the $(C_{1-6})$alkyl is optionally substituted with OH.

$R^5$-F: In another embodiment, $R^5$ is —CH$_2$—C(=O)—N($R^{51}$)$R^{52}$;
wherein $R^{51}$ is H or $(C_{1-6})$alkyl and $R^{52}$ is selected from H, $(C_{1-6})$alkyl, $(C_{3-7})$cycloalkyl, Het and Het-$(C_{1-3})$alkyl-;
wherein the $(C_{1-6})$alkyl is optionally substituted with 1 or 2 substituents each independently selected from —O$(C_{1-6})$alkyl and —N$((C_{1-6})$alkyl$)_2$; and wherein the Het and the Het portion of Het-$(C_{1-3})$alkyl- are each independently a 5- or 6-membered heterocycle containing 1 to 3 heteroatoms each independently selected from N, O and S, wherein the Het and the Het-$(C_{1-3})$alkyl- are each optionally substituted with 1 to 3 substituents each independently selected from halo, oxo, —OH, $(C_{1-6})$alkyl, $(C_{1-6})$haloalkyl, —(C=O)$(C_{1-6})$alkyl, —N$((C_{1-6})$alkyl$)_2$ and —NH(C=O)$(C_{1-6})$alkyl,
wherein the $(C_{1-6})$alkyl is optionally substituted with OH;
or $R^{51}$ and $R^{52}$, together with the N to which they are attached, are linked to form a 5- or 6-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;
wherein the heterocycle is optionally substituted with 1 to 3 substituents each independently selected from halo, oxo, —OH, $(C_{1-6})$alkyl, $(C_{1-6})$haloalkyl, —(C=O)$(C_{1-6})$alkyl, —N$((C_{1-6})$alkyl$)_2$ and —NH(C=O)$(C_{1-6})$alkyl,
wherein the $(C_{1-6})$alkyl is optionally substituted with OH.

$R^5$-G: In another embodiment, $R^5$ is —CH$_2$—C(=O)—N($R^{51}$)$R^{52}$, wherein $R^{51}$ is H or $(C_{1-6})$alkyl and $R^{52}$ is H or $(C_{1-6})$alkyl.

$R^5$-H: In another embodiment, $R^5$ is Het optionally substituted with 1 to 4 substituents each independently selected from $(C_{1-6})$alkyl, —OH, —COOH, —C(=O)—$(C_{1-6})$alkyl, —C(=O)—O—$(C_{1-6})$alkyl, —C(=O)—NH—$(C_{1-6})$alkyl, —C(=O)—N$((C_{1-6})$alkyl$)_2$, —C(=O)—NH$(C_{3-7})$cycloalkyl, —C(=O)—N$((C_{1-4})$alkyl$)(C_{3-7})$cycloalkyl and —SO$_2$$(C_{1-6})$alkyl.

$R^5$-I: In another embodiment, $R^5$ is a 5- or 6-membered saturated heterocycle containing 1 to 3 heteroatoms each independently selected from O, N and S, the heterocycle being optionally substituted with 1 to 4 substituents each independently selected from $(C_{1-4})$alkyl, —C(=O)—$(C_{1-4})$alkyl, —C(=O)—O—$(C_{1-4})$alkyl, —C(=O)—NH—$(C_{1-4})$alkyl, —C(=O)—N$((C_{1-4})$alkyl$)_2$, —C(=O)—NH$(C_{3-7})$cycloalkyl, —C(=O)—N$((C_{1-4})$alkyl$)(C_{3-7})$cycloalkyl and —SO$_2$$(C_{1-4})$alkyl.

$R^5$-J: In another embodiment, $R^5$ is selected from H, methyl, ethyl, propyl, 1-methylethyl,

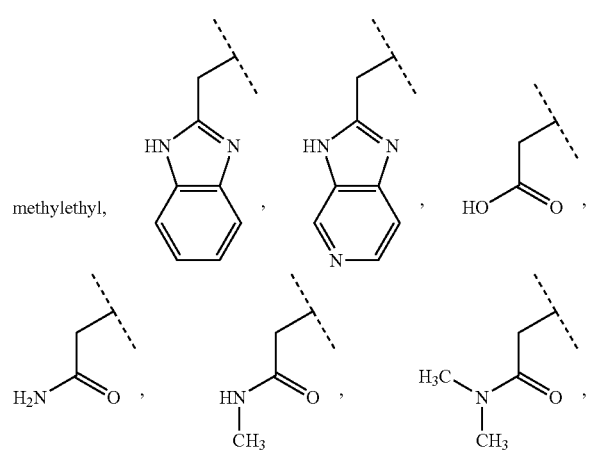

-continued

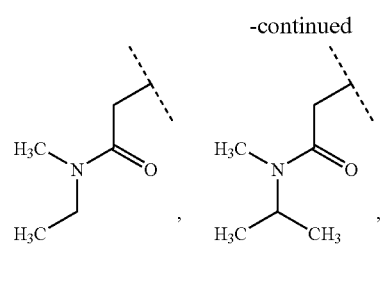
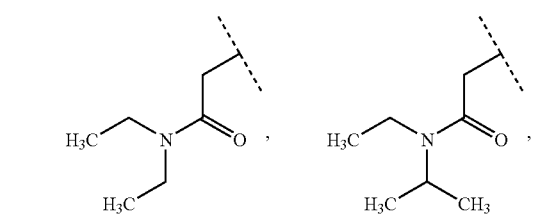
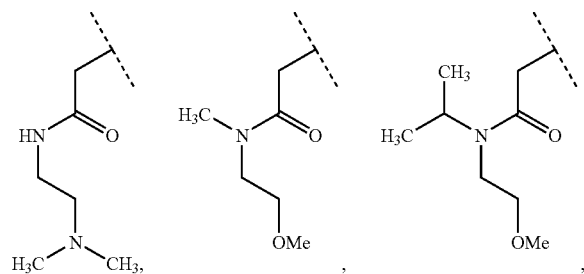
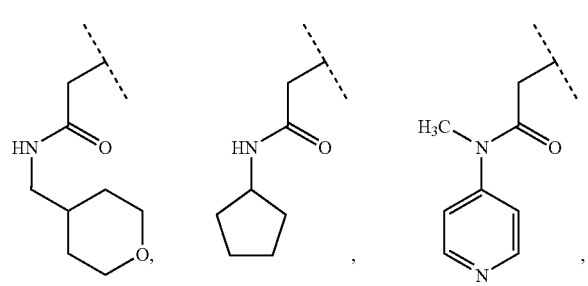
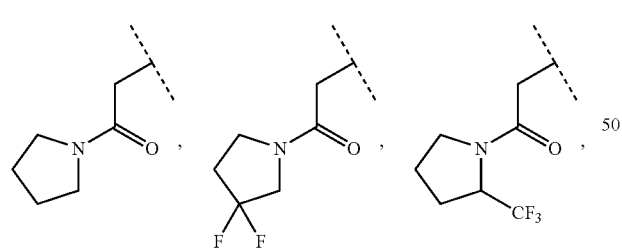
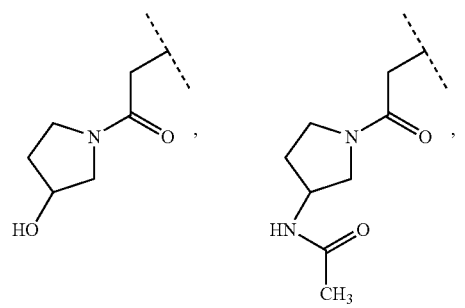

-continued

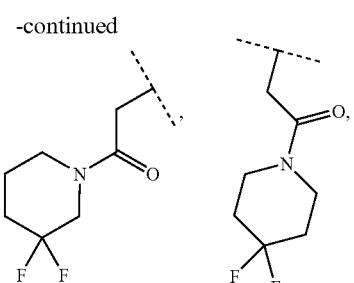
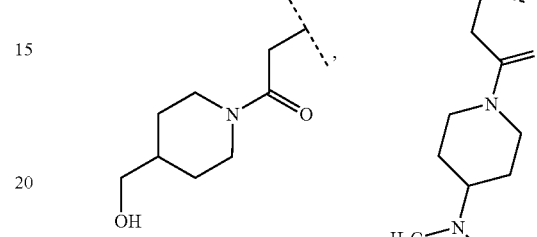
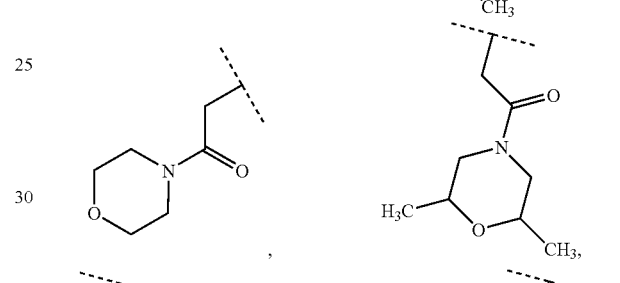
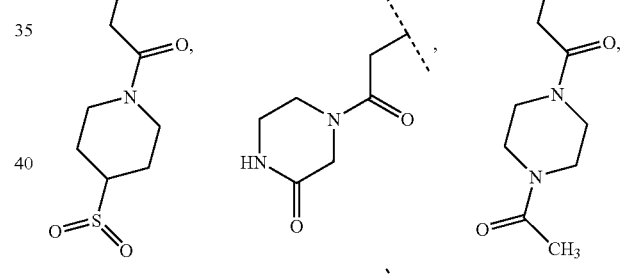
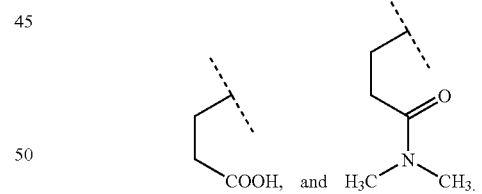

Any and each individual definition of $R^5$ as set out herein may be combined with any and each individual definition of X, $R^2$, $R^3$ and $R^6$ as set out herein.

$R^6$:

$R^6$-A: In one embodiment, $R^6$ is $(C_{3-7})$cycloalkyl optionally substituted with 1 to 5 substituents each independently selected from halo, $(C_{1-6})$alkyl, $(C_{1-6})$haloalkyl, $(C_{3-7})$cycloalkyl, —OH, —SH, —O—$(C_{1-4})$alkyl and —S—$(C_{1-4})$alkyl.

$R^6$-B: In another embodiment, $R^6$ is cyclohexyl optionally substituted with 1 to 3 substituents each independently selected from —OH and $(C_{1-4})$alkyl.

$R^6$-C: In still another embodiment, $R^6$ is selected from:

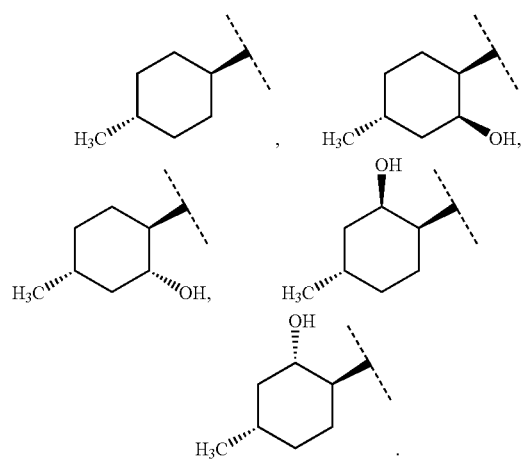

$R^6$-D: In still another embodiment, $R^6$ is

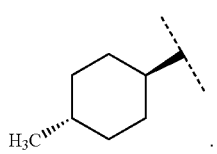

$R^6$-E: In an alternative embodiment, $R^6$ is aryl optionally substituted with 1 to 5 substituents each independently selected from halo, $(C_{1-6})$alkyl, $(C_{1-6})$haloalkyl, $(C_{3-7})$cycloalkyl, —OH, —SH, —O—$(C_{1-4})$alkyl and —S—$(C_{1-4})$alkyl;

provided that when $R^2$ is selected from:

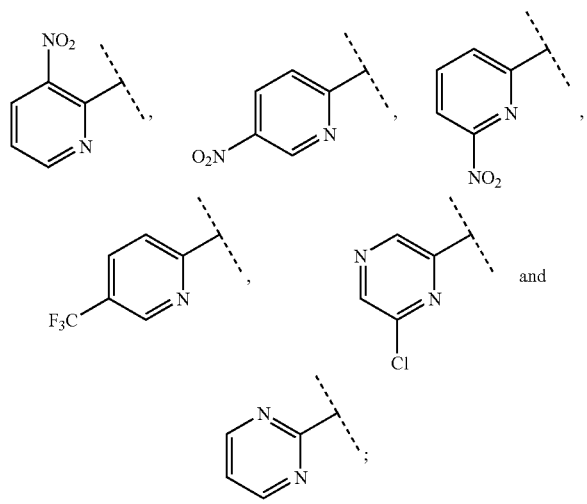

X is O; $R^3$ is H; and $R^5$ is H;
then $R^6$ is not

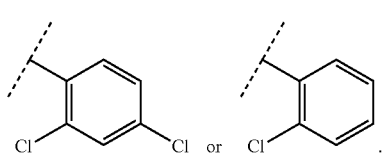

$R^6$-F: In another alternative embodiment, $R^6$ is phenyl optionally substituted with 1 to 3 substituents each independently selected from halo, $(C_{1-4})$alkyl, $(C_{3-7})$cycloalkyl and —S—$(C_{1-4})$alkyl;

provided that when $R^2$ is selected from:

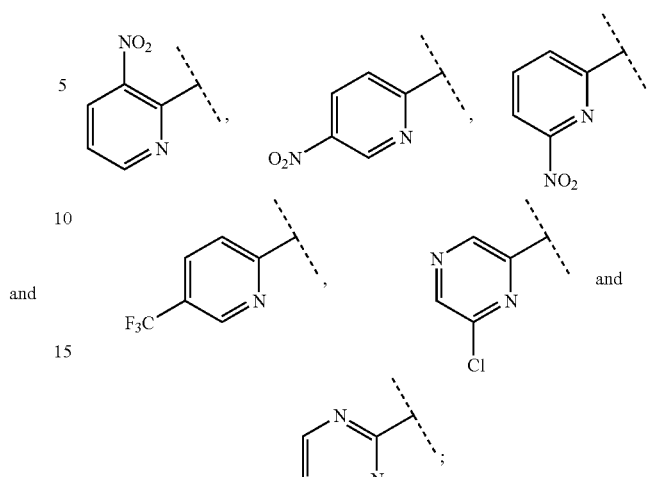

X is O; $R^3$ is H; and $R^5$ is H;
then $R^6$ is not

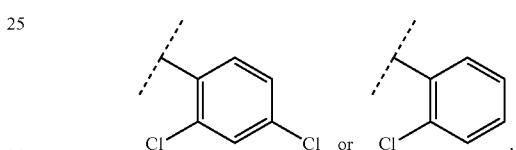

$R^6$-G: In yet another alternative embodiment, $R^6$ is phenyl optionally substituted with 1 to 3 substituents each independently selected from F, Cl, Br, methyl, ethyl, cyclopropyl and —S—$CH_3$;

provided that when $R^2$ is selected from:

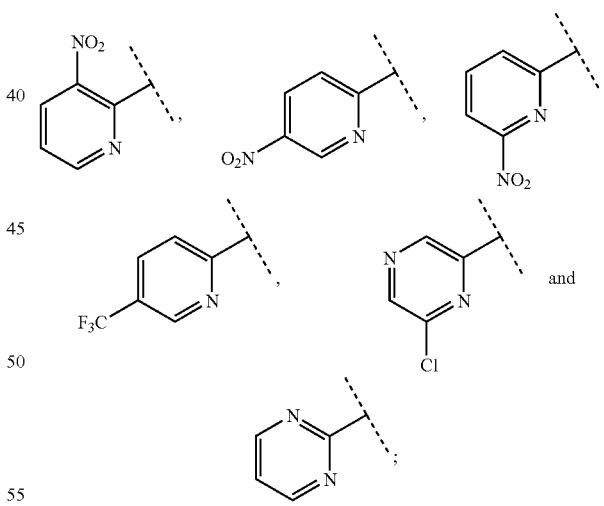

X is O; $R^3$ is H; and $R^5$ is H;
then $R^6$ is not

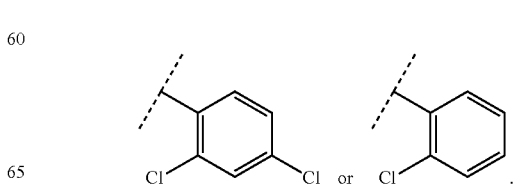

$R^6$-H: In still another embodiment, $R^6$ is selected from:

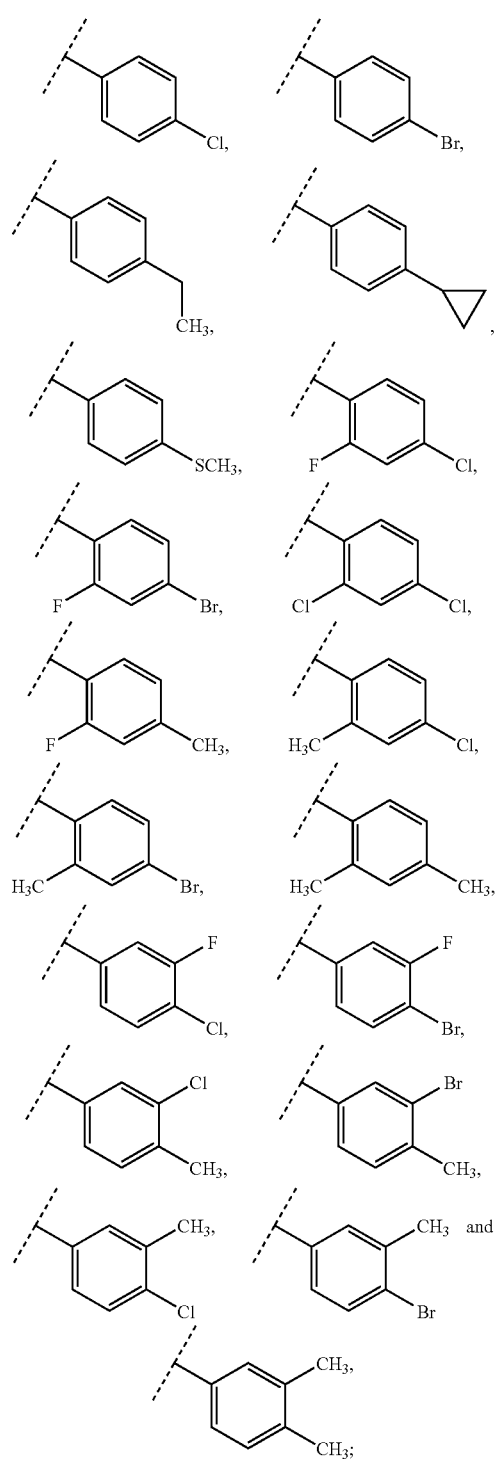

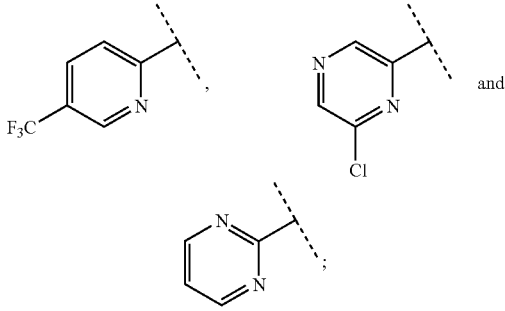

X is O; $R^3$ is H; and $R^5$ is H;
then $R^5$ is not

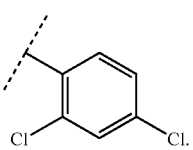

Any and each individual definition of $R^6$ as set out herein may be combined with any and each individual definition of X, $R^2$, $R^3$, and $R^5$ as set out herein.

Examples of preferred subgeneric embodiments of the present invention are set forth in the following table, wherein each substituent group of each embodiment is defined according to the definitions set forth above:

| Embodiment | X | $R^2$ | $R^3$ | $R^5$ | $R^6$ |
|---|---|---|---|---|---|
| E-1 | X-A | $R^2$-A | $R^3$-B | $R^5$-A | $R^6$-A |
| E-2 | X-B | $R^2$-A | $R^3$-B | $R^5$-A | $R^6$-A |
| E-3 | X-A | $R^2$-A | $R^3$-B | $R^5$-D | $R^6$-A |
| E-4 | X-B | $R^2$-A | $R^3$-B | $R^5$-D | $R^6$-A |
| E-5 | X-A | $R^2$-A | $R^3$-B | $R^5$-H | $R^6$-A |
| E-6 | X-B | $R^2$-A | $R^3$-B | $R^5$-H | $R^6$-A |
| E-7 | X-A | $R^2$-A | $R^3$-B | $R^5$-A | $R^6$-E |
| E-8 | X-B | $R^2$-A | $R^3$-B | $R^5$-A | $R^6$-E |
| E-9 | X-A | $R^2$-A | $R^3$-B | $R^5$-D | $R^6$-E |
| E-10 | X-B | $R^2$-A | $R^3$-B | $R^5$-D | $R^6$-E |
| E-11 | X-A | $R^2$-A | $R^3$-B | $R^5$-H | $R^6$-E |
| E-12 | X-B | $R^2$-A | $R^3$-B | $R^5$-H | $R^6$-E |
| E-13 | X-A | $R^2$-A | $R^3$-D | $R^5$-A | $R^6$-A |
| E-14 | X-B | $R^2$-A | $R^3$-D | $R^5$-A | $R^6$-A |
| E-15 | X-A | $R^2$-A | $R^3$-D | $R^5$-D | $R^6$-A |
| E-16 | X-B | $R^2$-A | $R^3$-D | $R^5$-D | $R^6$-A |
| E-17 | X-A | $R^2$-A | $R^3$-D | $R^5$-H | $R^6$-A |
| E-18 | X-B | $R^2$-A | $R^3$-D | $R^5$-H | $R^6$-A |
| E-19 | X-A | $R^2$-A | $R^3$-D | $R^5$-A | $R^6$-E |
| E-20 | X-B | $R^2$-A | $R^3$-D | $R^5$-A | $R^6$-E |
| E-21 | X-A | $R^2$-A | $R^3$-D | $R^5$-D | $R^6$-E |
| E-22 | X-B | $R^2$-A | $R^3$-D | $R^5$-D | $R^6$-E |
| E-23 | X-A | $R^2$-A | $R^3$-D | $R^5$-H | $R^6$-E |
| E-24 | X-B | $R^2$-A | $R^3$-D | $R^5$-H | $R^6$-E |
| E-25 | X-A | $R^2$-D | $R^3$-D | $R^5$-B | $R^6$-B |
| E-26 | X-A | $R^2$-D | $R^3$-D | $R^5$-F | $R^6$-B |
| E-27 | X-A | $R^2$-D | $R^3$-D | $R^5$-I | $R^6$-B |
| E-28 | X-A | $R^2$-D | $R^3$-D | $R^5$-B | $R^6$-D |
| E-29 | X-A | $R^2$-D | $R^3$-D | $R^5$-F | $R^6$-D |
| E-30 | X-A | $R^2$-D | $R^3$-D | $R^5$-I | $R^6$-D |
| E-31 | X-A | $R^2$-D | $R^3$-D | $R^5$-B | $R^6$-F |
| E-32 | X-A | $R^2$-D | $R^3$-D | $R^5$-F | $R^6$-F |
| E-33 | X-A | $R^2$-D | $R^3$-D | $R^5$-I | $R^6$-F |
| E-34 | X-A | $R^2$-F | $R^3$-D | $R^5$-B | $R^6$-B |
| E-35 | X-A | $R^2$-F | $R^3$-D | $R^5$-F | $R^6$-B |
| E-36 | X-A | $R^2$-F | $R^3$-D | $R^5$I | $R^6$-B | provided that when $R^2$ is selected from:

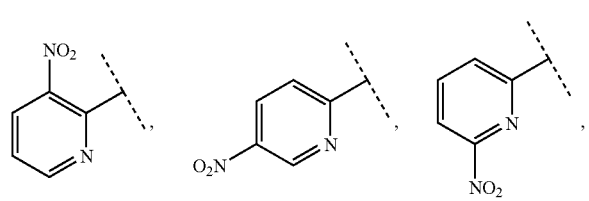

-continued

| Embodiment | X | R² | R³ | R⁵ | R⁶ |
|---|---|---|---|---|---|
| E-37 | X-A | R²-F | R³-D | R⁵-B | R⁶-D |
| E-38 | X-A | R²-F | R³-D | R⁵-F | R⁶-D |
| E-39 | X-A | R²-F | R³-D | R⁵-I | R⁶-D |
| E-40 | X-A | R²-F | R³-D | R⁵-B | R⁶-F |
| E-41 | X-A | R²-F | R³-D | R⁵-F | R⁶-F |
| E-42 | X-A | R²-F | R³-D | R⁵-I | R⁶-F |
| E-43 | X-A | R²-H | R³-D | R⁵-B | R⁶-B |
| E-44 | X-A | R²-H | R³-D | R⁵-F | R⁶-B |
| E-45 | X-A | R²-H | R³-D | R⁵-I | R⁶-B |
| E-46 | X-A | R²-H | R³-D | R⁵-B | R⁶-D |
| E-47 | X-A | R²-H | R³-D | R⁵-F | R⁶-D |
| E-48 | X-A | R²-H | R³-D | R⁵-I | R⁶-D |
| E-49 | X-A | R²-H | R³-D | R⁵-B | R⁶-F |
| E-50 | X-A | R²-H | R³-D | R⁵-F | R⁶-F |
| E-51 | X-A | R²-H | R³-D | R⁵-I | R⁶-F |

Examples of most preferred compounds according to this invention are each single compound listed in the following Tables 1 and 2.

In general, all tautomeric and isomeric forms and mixtures thereof, for example, individual geometric isomers, stereoisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000, herein incorporated by reference. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

The compounds according to the present invention are inhibitors of the hepatitis C virus NS5B RNA-dependent RNA polymerase and thus may be used to inhibit replication of hepatitis C viral RNA.

A compound according to the present invention may also be used as a laboratory reagent or a research reagent. For example, a compound of the present invention may be used as positive control to validate assays, including but not limited to surrogate cell-based assays and in vitro or in vivo viral replication assays.

Compounds according to the present invention may also be used as probes to study the hepatitis C virus NS5B polymerase, including but not limited to the mechanism of action of the polymerase, conformational changes undergone by the polymerase under various conditions and interactions with entities which bind to or otherwise interact with the polymerase.

Compounds of the invention used as probes may be labelled with a label which allows recognition either directly or indirectly of the compound such that it can be detected, measured and quantified. Labels contemplated for use with the compounds of the invention include, but are not limited to, fluorescent labels, chemiluminescent labels, calorimetric labels, enzymatic markers, radioactive isotopes, affinity tags and photoreactive groups.

Compounds of the invention used as probes may also be labelled with an affinity tag whose strong affinity for a receptor can be used to extract from a solution the entity to which the ligand is attached. Affinity tags include but are not limited to biotin or a derivative thereof, a histidine polypeptide, a polyarginine, an amylose sugar moiety or a defined epitope recognizable by a specific antibody.

Furthermore, compounds of the invention used as probes may be labelled with a photoreactive group which is transformed, upon activation by light, from an inert group to a reactive species, such as a free radical. Photoreactive groups include but are not limited to photoaffinity labels such as benzophenone and azide groups.

Furthermore, a compound according to the present invention may be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

Pharmaceutical Composition

Compounds of the present invention may be administered to a mammal in need of treatment for hepatitis C viral infection as a pharmaceutical composition comprising a therapeutically effective amount of a compound according to the invention or a pharmaceutically acceptable salt or ester thereof; and one or more conventional non-toxic pharmaceutically-acceptable carriers, adjuvants or vehicles. The specific formulation of the composition is determined by the solubility and chemical nature of the compound, the chosen route of administration and standard pharmaceutical practice. The pharmaceutical composition according to the present invention may be administered orally or systemically.

For oral administration, the compound, or a pharmaceutically acceptable salt or ester thereof, can be formulated in any orally acceptable dosage form including but not limited to aqueous suspensions and solutions, capsules or tablets. For systemic administration, including but not limited to administration by subcutaneous, intracutaneous, intravenous, intramuscular, intra-articular, intrasynovial, intrasternal, intrathecal, and intralesional injection or infusion techniques, it is preferred to use a solution of the compound, or a pharmaceutically acceptable salt or ester thereof, in a pharmaceutically acceptable sterile aqueous vehicle.

Pharmaceutically acceptable carriers, adjuvants, vehicles, excipients and additives as well as methods of formulating pharmaceutical compositions for various modes of administration are well-known to those of skill in the art and are described in pharmaceutical texts such as Remington: The Science and Practice of Pharmacy, 21 st Edition, Lippincott Williams & Wilkins, 2005; and L. V. Allen, N. G. Popovish and H. C. Ansel, Pharmaceutical Dosage Forms and Drug Delivery Systems, 8th ed., Lippincott Williams & Wilkins, 2004, herein incorporated by reference.

The dosage administered will vary depending upon known factors, including but not limited to the activity and pharmacodynamic characteristics of the specific compound employed and its mode, time and route of administration; the age, diet, gender, body weight and general health status of the recipient; the nature and extent of the symptoms; the severity and course of the infection; the kind of concurrent treatment; the frequency of treatment; the effect desired; and the judgment of the treating physician. In general, the compound is most desirably administered at a dosage level that will generally afford antivirally effective results without causing any harmful or deleterious side effects.

A daily dosage of active ingredient can be expected to be about 0.01 to about 200 milligrams per kilogram of body weight, with the preferred dose being about 0.1 to about 50 mg/kg. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Combination Therapy

Combination therapy is contemplated wherein a compound according to the invention, or a pharmaceutically acceptable salt or ester thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt or ester thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, $\alpha$-, $\beta$-, $\delta$-, $\omega$-, and $\tau$-interferons, while examples of class II interferons include, but are not limited to, $\gamma$-interferons.

Inhibitors of HCV NS3 protease include agents (compounds or biologicals) that are effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700, WO 2006/007708 (all by Boehringer Ingelheim), WO 02/060926, WO 03/053349, WO 03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune), WO 01/77113, WO 01/81325, WO 02/08187, WO 02/08198, WO 02/08244, WO 02/08256, WO 02/48172, WO 03/062228, WO 03/062265, WO 2005/021584, WO 2005/030796, WO 2005/058821, WO 2005/051980, WO 2005/085197, WO 2005/085242, WO 2005/085275, WO 2005/087721, WO 2005/087725, WO 2005/087730, WO 2005/087731, WO 2005/107745 and WO 2005/113581 (all by Schering); and the candidates VX-950, ITMN-191 and SCH-503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388, WO 2006/007693 (all by Boehringer Ingelheim), WO 01/47883 (Japan Tobacco), WO 03/000254 (Japan Tobacco), WO 03/026587 (BMS), WO 03/101993 (Neogenesis), WO 2004/087714 (IRBM), WO 2005/012288 (Genelabs), WO 2005/014543 (Japan Tobacco), WO 2005/049622 (Japan Tobacco), and WO 2005/121132 (Shionogi), and the candidates XTL-2125, HCV 796, R-1626, R-7128, NM 283, VCH-759, GSK625433 and PF868554. Inhibitors of another target in the HCV life cycle include agents (compounds or biologicals) that are effective to inhibit the formation and/or replication of HCV other than by inhibiting the function of the HCV NS3 protease or HCV polymerase. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

HIV inhibitors include agents (compounds or biologicals) that are effective to inhibit the formation and/or replication of HIV. This includes but is not limited to agents that interfere with either host or viral mechanisms necessary for the formation and/or replication of HIV in a mammal. HIV inhibitors include, but are not limited to:

NRTIs (nucleoside or nucleotide reverse transcriptase inhibitors; including but not limited to zidovudine, didanosine, zalcitabine, stavudine, lamivudine, emtricitabine, abacavir, and tenofovir);

NNRTIs (non-nucleoside reverse transcriptase inhibitors; including but not limited to nevirapine, delavirdine, efavirenz, etravirine, rilpivirine and BILR 355);

protease inhibitors (including but not limited to ritonavir, tipranavir, saquinavir, nelfinavir, indinavir, amprenavir, fosamprenavir, atazanavir, lopinavir, darunavir and brecanavir);

entry inhibitors including but not limited to
  CCR5 antagonists (including but not limited to maraviroc (UK-427,857) and TAK-652),
  CXCR4 antagonists (including but not limited to AMD-11070),
  fusion inhibitors (including but not limited to enfuvirtide (T-20)) and
  others (including but not limited to BMS-488043);
integrase inhibitors (including but not limited to MK-0518, c-1605, BMS-538158 and GS 9137);
TAT inhibitors;
maturation inhibitors (including but not limited to bevirimat (PA-457)); and
immunomodulating agents (including but not limited to levamisole).

HAV inhibitors include agents (compounds or biologicals) that are effective to inhibit the formation and/or replication of HAV. This includes but is not limited to agents that interfere with either host or viral mechanisms necessary for the formation and/or replication of HAV in a mammal. HAV inhibitors include but are not limited to Hepatitis A vaccines.

HBV inhibitors include agents (compounds or biologicals) that are effective to inhibit the formation and/or replication of HBV in a mammal. This includes but is not limited to agents that interfere with either host or viral mechanisms necessary for the formation and/or replication of HBV in a mammal. HBV inhibitors include, but are not limited to, agents that inhibit the HBV viral DNA polymerase and HBV vaccines.

Therefore, according to one embodiment, the pharmaceutical composition of this invention additionally comprises a therapeutically effective amount of one or more antiviral agents.

A further embodiment provides the pharmaceutical composition of this invention wherein the one or more antiviral agent comprises at least one other anti-HCV agent.

According to a more specific embodiment of the pharmaceutical composition of this invention, the at least one other anti-HCV agent comprises at least one immunomodulatory agent.

According to another more specific embodiment of the pharmaceutical composition of this invention, the at least one other anti-HCV agent comprises at least one other inhibitor of HCV polymerase.

According to yet another more specific embodiment of the pharmaceutical composition of this invention, the at least one other anti-HCV agent comprises at least one inhibitor of HCV NS3 protease.

According to still another more specific embodiment of the pharmaceutical composition of this invention, the at least one other anti-HCV agent comprises at least one inhibitor of another target in the HCV life cycle.

All of the documents cited herein are incorporated in to the invention as a reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

Methodology and Synthesis

The synthesis of compounds of formula (I) according to this invention is conveniently accomplished following the general procedure outlined in Schemes 1 and 2 below wherein $R^2$, X, $R^3$, $R^5$ and $R^6$ are as defined herein. Other procedures by which compounds of the invention may be prepared are well known in the art or are set forth in the examples below.

Scheme 1:

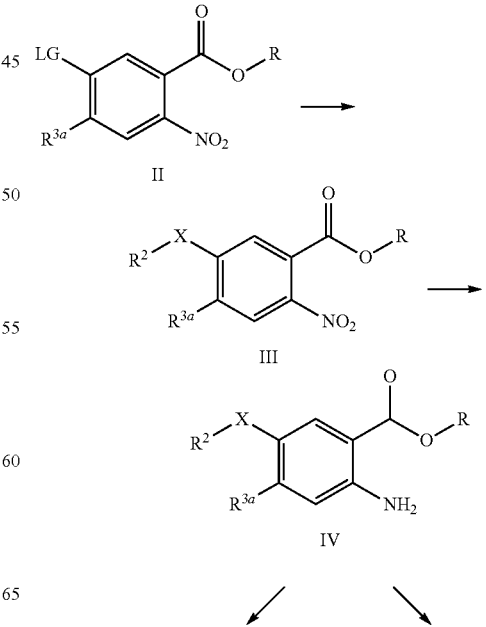

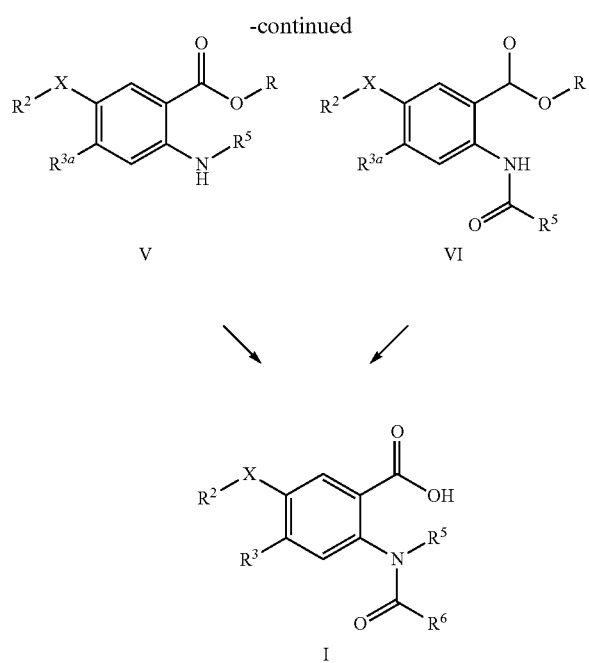

Intermediates of formula (II) wherein $R^{3a}$ is $R^3$ as defined herein or is a precursor group transformable to $R^3$ as defined herein, R is an ester protecting group, such as methyl or ethyl, and LG is a leaving group such as F or Cl, are commercially available or may be prepared by procedures well known in the art or as set forth in the examples below. It will be apparent to one skilled in the art that when the group $R^{3a}$ is a precursor group, it may be transformed to $R^3$ as defined herein at any chemically convenient intermediate stage in the scheme prior to formation of the compounds of formula (I), by procedures well known in the art or as set forth in the examples below.

Coupling of intermediates (II) with reactants of the formula $R^2X$—H, wherein $R^2$ and X are as defined herein, using reaction conditions well known in the art or as set forth in the examples below, provides intermediates of formula (III). Such reaction conditions include but are not limited to $S_NAr$ reaction conditions and Ullman coupling conditions. One skilled in the art will appreciate that $R^2$ groups of the compounds according to the invention differ in their substitution patterns and that it is contemplated that one $R^2$ group may be transformed to another $R^2$ group by procedures well known in the art or as set forth in the examples below, at any chemically convenient intermediate stage in the scheme.

The nitro group of intermediates (III) is reduced to an amino group under well-known conditions to provide intermediates of formula (IV), or their salts with acids such as hydrochloric acid. The $R^5$ group may be added to the amino group of intermediates of formula (IV) by any suitable reaction known to the skilled in the art, including but not limited to alkylation and reductive amination, to provide intermediates of formula (V). The reductive amination reaction is conveniently carried out by allowing the intermediate of formula (IV) to react with an appropriately substituted aldehyde or ketone or suitable derivative thereof, followed by treatment with sodium triacetoxyborohydride, according to Abdel-Magid, A. F.; Carson, K. G.; Harris, B. D.; Maryanoff, C. A.; Shah, R. D. *J. Org. Chem.* 1996, 61, 3849. Suitable derivatives of aldehydes and ketones are well known in the art and include, but are not limited to, enol ethers and the like. The aldehydes, ketones, or suitable derivatives thereof are commercially available or obtainable by procedures well known in the art or as set forth in the examples below. Intermediates (V) are acylated with appropriate acylating agents, which are commercially available or obtainable by procedures well known in the art or as set forth in the examples below. The ester protecting group R is then hydrolysed, by procedures well known in the art or as set forth in the examples below, to provide compounds of formula (I).

Alternatively, the amino group of intermediates of formula (IV) may be acylated as previously described to provide intermediates of formula (VI). Alkylation of the amide nitrogen atom of intermediates of formula (VI), by procedures well known in the art or as set forth in the examples below, followed by hydrolysis of the ester protecting group as previously described, provides compounds of formula (I).

One skilled in the art will appreciate that $R^5$ and $R^6$ groups of the compounds according to the invention differ in their substitution patterns and that it is contemplated that one $R^5$ group may be transformed to another $R^5$ group, or that one $R^6$ group may be transformed to another $R^6$ group, by procedures well known in the art or as set forth in the examples below, at any chemically convenient intermediate stage in the scheme.

Alternatively, the preparation of compounds of formula (I) may be accomplished by the procedure outlined in Scheme 2 below, wherein $R^2$, X, $R^3$, $R^5$ and $R^6$ are as defined herein, R is an ester protecting group such as methyl or ethyl and PG is a suitable protecting group for the XH functionality, well known to one skilled in the art, including but not limited to a benzyl group.

Scheme 2:

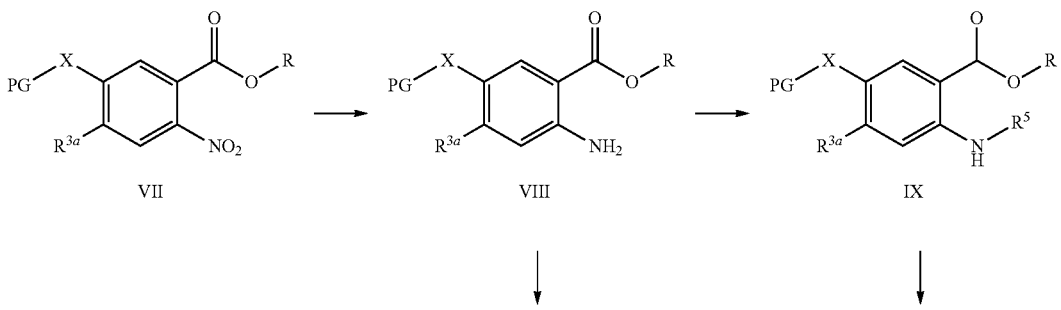

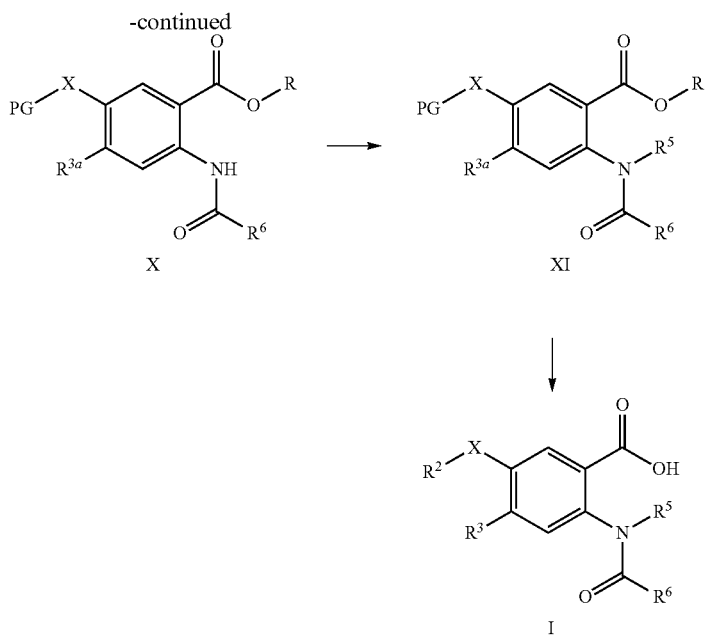

Intermediates of formula VII are commercially available or may be prepared by procedures well known in the art or as set forth in the examples below. Reduction of the nitro group to the amino group and introduction of the $R^5$ and —C(=O)$R^6$ groups is achieved as described above to give intermediates of formula (XI). The intermediates of formula (XI) are transformed to compounds of formula (I) by deprotecting the XH group by procedures well known in the art or as set forth in the examples below and coupling the resulting free phenol or thiol to a reactant of formula $R^2$-LG wherein LG is a leaving group such as F or Cl, using procedures well known in the art or as set forth in the examples below. Such procedures include but are not limited to $S_NAr$ reactions and Ullman coupling reactions. Finally, the ester is deprotected by hydrolysis as previously described.

EXAMPLES

Other features of the present invention will become apparent from the following non-limiting examples which illustrate, by way of example, the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem., (1978), 43, 2923. Mass spectral analyses are recorded using electrospray mass spectrometry. Analytical HPLC is carried out under standard conditions using a Combiscreen™ ODS-AQ C18 reverse phase column, YMC, 50×4.6 mm i.d., 5 μM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:
Ac: acetyl;
AcCl: acetyl chloride;
AcOH: acetic acid;
$Ac_2O$: acetic anhydride;
BINAP: 2,2'-bis(diphenylphosphino)-1,1'-binaphthyl;
Bn: benzyl (phenylmethyl);
BnBr: benzyl bromide;
BOC or Boc: tert-butyloxycarbonyl;
Bu: butyl;
n-BuOAc: n-butyl acetate
DBU: 1,8-diazabicyclo[5.4.0]undec-7-ene;
DCE: dichloroethane;
DCM: dichloromethane;
DIEA: diisopropylethylamine;
DMAP: 4-dimethylaminopyridine;
DME: dimethoxyethane;
DMF: N,N-dimethylformamide;
DMSO: dimethylsulfoxide;
$EC_{50}$: 50% effective concentration;
EEDQ: 2-ethoxy-1-ethoxycarbonyl-1,2-dihydroquinoline;
eq.: molar equivalent;
Et: ethyl;
$Et_3N$: triethylamine;
$Et_2O$: diethyl ether;
EtOAc: ethyl acetate;
EtOH: ethanol;
HPLC: high performance liquid chromatography;
$IC_{50}$: 50% inhibitory concentration;
$^iPr$ or i-Pr: 1-methylethyl (iso-propyl);
Me: methyl;
MeCN: acetonitrile;

MeI: iodomethane;
MeOH: methanol;
MS: mass spectrometry (MALDI-TOF: Matrix Assisted Laser Desorption Ionization-Time of Flight, FAB: Fast Atom Bombardment);
NIS: N-iodosuccinamide;
NMP: N-methylpyrrolidone;
NMR: nuclear magnetic resonance spectroscopy;
Ph: phenyl;
PG: protecting group;
Pr: propyl;
RT: room temperature (approximately 18° C. to 25° C.);
TBTU: O-benzotriazol-1-yl-N,N,N',N'-tetramethyluronium tetrafluoroborate;
tert-butyl or t-butyl: 1,1-dimethylethyl;
TFA: trifluoroacetic acid;
THF: tetrahydrofuran;
TLC: thin layer chromatography.

Example 1A

Preparation of Intermediate 1a9

Step 1:

To a mixture of 5-hydroxy-2-nitrobenzoic acid 1a1 (50 g, 0.273 mol) in MeOH (500 mL), is added $SOCl_2$ (40 mL, 65.2 g, 0.55 mol) dropwise over about 30 minutes and the mixture is heated at reflux for 2 hours. Excess $SOCl_2$ (20 mL, 32.6 g, 0.27 mol) is carefully added and heating at reflux is continued overnight. Further $SOCl_2$ (20 mL, 32.6 g, 0.27 mol) is added and heating at reflux is continued for 1 hour. The reaction mixture is cooled to room temperature and concentrated under reduced pressure. The residue is diluted with EtOAc (600 mL), washed with saturated aqueous $NaHCO_3$ and brine, dried over $MgSO_4$, filtered and concentrated to dryness. The methyl ester 1a2 is recovered as a solid from $CH_2Cl_2$ and hexane.

Step 2:

A mixture of compound 1a2 (51.2 g, 0.26 mol), anhydrous $K_2CO_3$ (150 g, 1.09 mol) and $PhCH_2Br$ (39 mL, 56 g, 0.33 mol) in acetone (500 mL) is stirred overnight at room temperature. The mixture is filtered and the filtrate is concentrated, diluted with EtOAc (1.5 L), washed with water and brine, dried over $MgSO_4$, filtered and concentrated to dryness. Compound 1a3 is recovered from EtOAc and hexane.

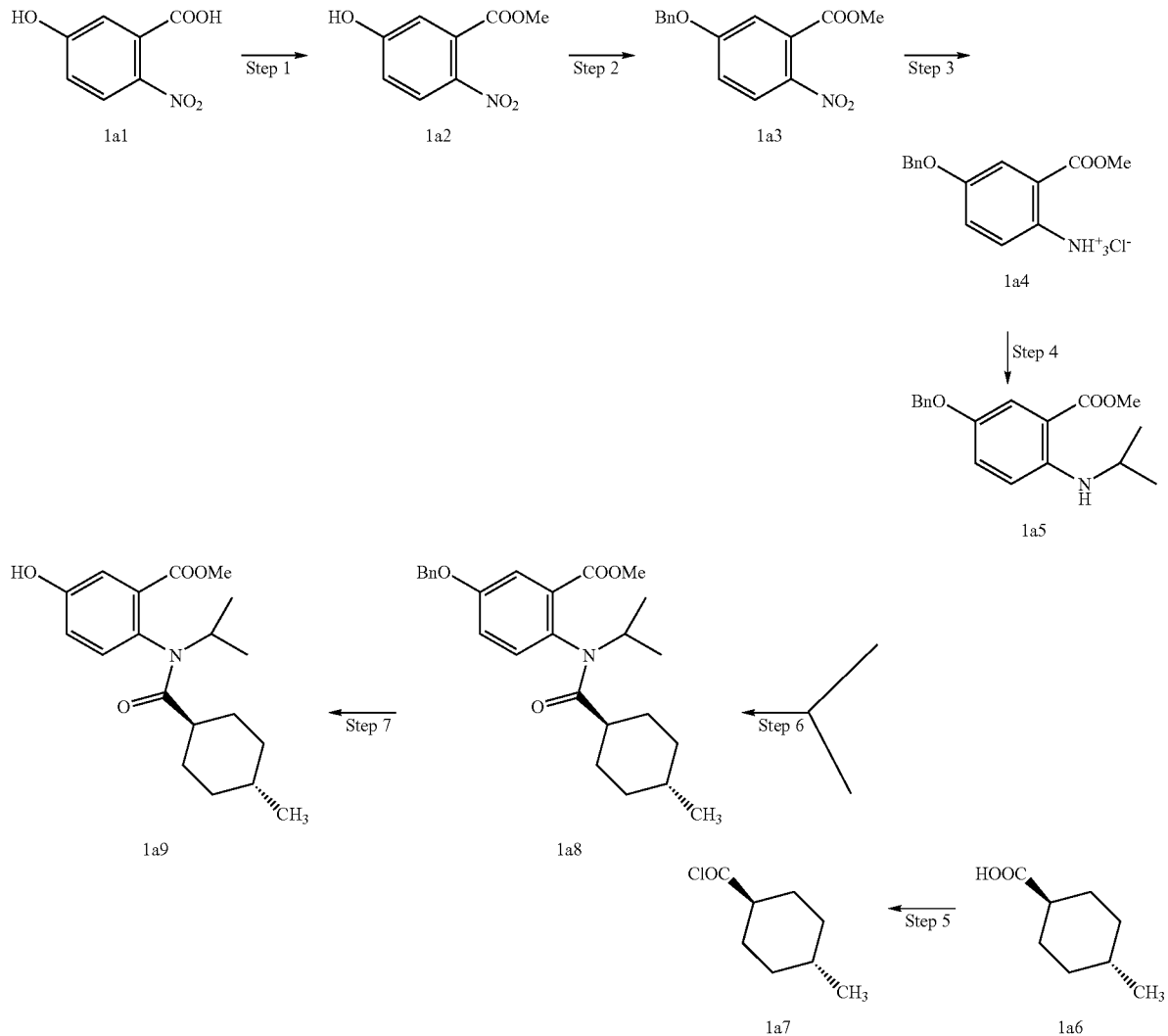

Step 3:

To a stirred mixture of compound 1a3 (68.4 g, 0.24 mol) in ethanol (1.2 L) is added Fe powder (150 g, 2.7 mol) followed by AcOH (65 mL). The mixture is heated under reflux for 4 hours, then further Fe powder (75 g, 1.3 mol) and AcOH (30 mL) are added and heating at reflux is continued for 1.5 hours. The mixture is filtered and the solid and filtrate are treated separately.

The solid is mixed with saturated aqueous $NaHCO_3$ and EtOAc, and solid $NaHCO_3$ is added until a basic pH is attained. The mixture is filtered through Celite™ and rinsed with EtOAc. The aqueous layer is extracted twice with EtOAc (2×1 L) and the organic layers are combined.

The filtrate is concentrated under reduced pressure, the residue is diluted with EtOAc (1 L) and saturated aqueous $NaHCO_3$ is added. Solid $NaHCO_3$ is added to the mixture until the pH is basic. The mixture is filtered through Celite™ and rinsed with EtOAc.

The organic phases obtained from treatment of the solid and filtrate portions above are combined, then washed with brine, dried over $MgSO_4$ and concentrated to dryness and the residue is recovered from $CH_2Cl_2$ and hexane. To a stirred mixture of the recovered residue (46.7 g, 0.18 mol) in $Et_2O$ (400 mL) is added 2M HCl in $Et_2O$ (180 mL, 0.38 mol). The mixture is stirred at room temperature for 2 hours and compound 1a4 is collected by filtration.

Step 4:

The procedure used is adapted from: Abdel-Magid, A. F.; Carson, K. G.; Harris, B. D.; Maryanoff, C. A.; Shah, R. D. *J. Org. Chem.* 1996, 61, 3849. To a mixture of compound 1a4 (30 g, 0.1 mol) and $CH_2Cl_2$ (600 mL) is added 2-methoxypropene (36 mL, 27 g, 0.38 mol), followed by $NaBH(OAc)_3$ (43.2 g, 0.2 mol). The mixture is stirred at RT for 7 hours, diluted with EtOAc, washed with saturated aqueous $NaHCO_3$ and brine, dried over $MgSO_4$, filtered and concentrated to dryness. Compound 1a5 is recovered from EtOAc and hexane.

Step 5:

To a mixture of compound 1a6 (43.4 g, 305 mmol) and anhydrous $CH_2Cl_2$ (400 mL) under Ar atmosphere at room temperature is added $(COCl)_2$ (53.2 mL, 610 mmol) in $CH_2Cl_2$ (305 mL) dropwise over 1 hour at room temperature. The mixture is stirred for 1 hour at room temperature and anhydrous DMF (1 mL) is added dropwise. The mixture is stirred overnight at RT and concentrated under reduced pressure. The residue is diluted with pentane and filtered. The filtrate is twice concentrated under reduced pressure, diluted with pentane and filtered, then concentrated under reduced pressure to provide acid chloride 1a7.

Step 6:

To a mixture of compound 1a5 (99.6 g, 0.32 mol) in anhydrous pyridine (1.5 L) is added compound 1a7 (100 mL, 100 g, 0.62 mol) and DMAP (3.8 g, 0.03 mol). The mixture is stirred at 60° C. overnight and concentrated under reduced pressure. The residue is diluted with EtOAc (3 L), washed with 2M HCl aqueous solution (4×1 L), saturated aqueous $NaHCO_3$ (6×500 mL) and brine, dried over $MgSO_4$, filtered and concentrated to dryness to give compound 1a8.

Step 7:

A mixture of compound 1a8 (130 g, 0.3 mol), MeOH (0.6 L) and EtOAc (1.5 L) is carefully added to 10% Pd/C (15 g) under Ar. Argon is bubbled through the mixture for 10 minutes with stirring then $H_2$ is bubbled into the mixture and stirring is continued at room temperature for 8 hours. The mixture is filtered through Celite™ and the filtrate is concentrated under reduced pressure. Compound 1a9 is collected from Hexanes.

Example 1B

Preparation of Intermediate 1b3

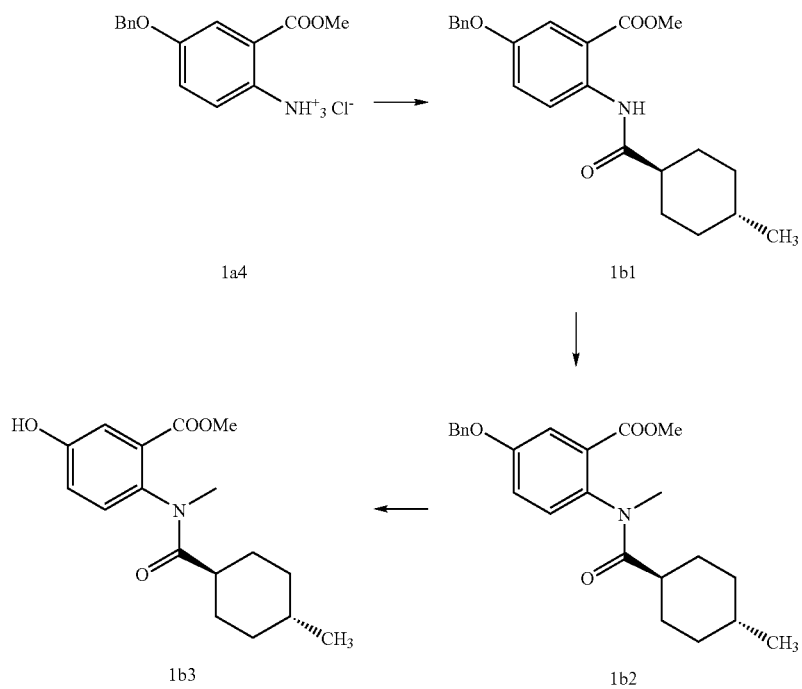

49

Step 1:

To a mixture of compound 1a4 (Example 1A) (2.0 g, 6.8 mmol) in anhydrous pyridine (35 mL) is added compound 1a7 (Example 1A) (1.65 mL, 10.2 mmol) and DMAP (82 mg, 0.67 mmol). The mixture is stirred at 50° C. for 1 hour and concentrated under reduced pressure. The residue is diluted with EtOAc (300 mL), washed with 2M HCl aqueous solution (5×200 mL), saturated aqueous $NaHCO_3$ solution (6×200 mL) and brine (200 mL), dried over $MgSO_4$, filtered and concentrated. Compound 1b1 is recovered from DCM/Hexanes.

Step 2:

To a mixture of compound 1b1 (2.0 g, 5.24 mmol) and anhydrous DMF (30 mL) cooled in an ice-water bath is added NaH (60%, 0.25 g, 10.5 mmol) and the mixture is stirred for 40 minutes. $CH_3I$ (0.9 mL, 14.5 mmol, 2.8 eq) is added and the mixture is allowed to stir at room temperature overnight. The mixture is diluted with EtOAc (600 mL), washed with saturated aqueous $NH_4Cl$ (3×300 mL), saturated aqueous $NaHCO_3$ (300 mL) and brine (300 mL), dried over $MgSO_4$, filtered and concentrated. The crude product is purified by ISCO CombiFlash column ($SiO_2$, Hexane/EtOAc: 10/0 to 5/5) to afford compound 1b2.

Step 3:

A mixture of compound 1b2 (2.07 g, 5.24. mmol) in anhydrous MeOH (33 mL) and anhydrous EtOAc (83 mL) is carefully added to Pd/C (10%, 0.23 g) under Ar atmosphere. Ar is bubbled through the mixture for 2 minutes and $H_2$ is then bubbled through the mixture with stirring at room temperature for 2.5 hours. The mixture is filtered through Celite™ and the filtrate is concentrated. Solid phenol 1b3 is obtained from a diethylether/hexanes mixture (1/9, 100 mL).

Intermediate 1b3 can be converted to compounds of formula (I) using the methods of the following examples.

Example 2A

Preparation of Compound 1001, Table 1

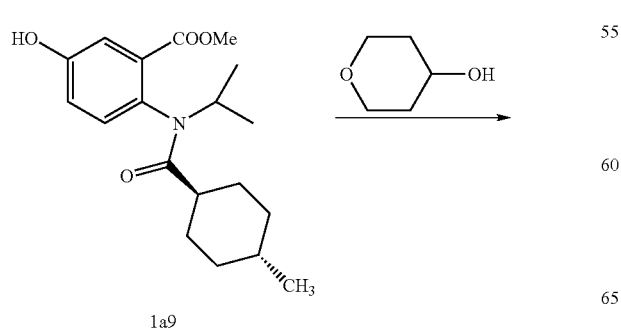

1a9

50

-continued

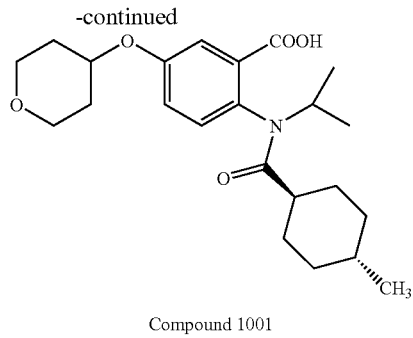

Compound 1001

Phenol 1a9 (Example 1A) (20 mg, 0.06 mmol) is combined with 4-hydroxytetrahydropyran (0.08 mmol) and triphenylphosphine (20 mg, 0.08 mmol) in THF (1 mL). Diisopropylazodicarboxylate (0.02 mL, 0.10 mmol) is added and the mixture is allowed to stir overnight at ambient temperature. Aqueous NaOH (10N, 0.06 mL, 0.6 mmol), water (0.06 mL) and methanol (0.4 mL) are added and the mixture is warmed to 50° C. and allowed to stir for 2.5 hours. Purification by preparative HPLC affords compound 1001 (Table 1).

Example 2B

Preparation of Compound 1003, Table 1

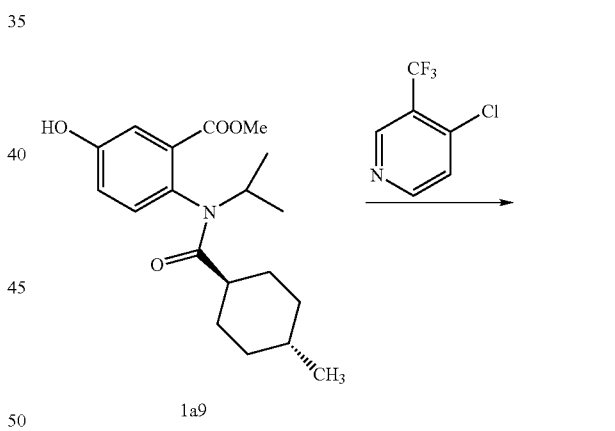

1a9

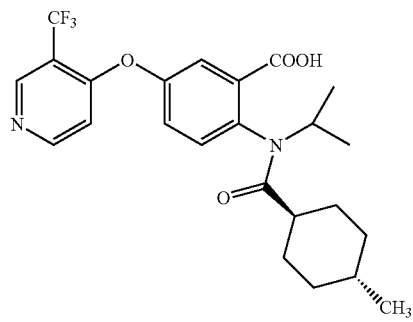

Compound 1003

Phenol 1a9 (Example 1A) (20 mg, 0.06 mmol) is combined with 3-trifluoromethyl-4-chloropyridine (16 mg, 0.07 mmol) and K₂CO₃ (31 mg, 0.22 mmol) in DMSO (0.5 mL). The mixture is heated to 100° C. and allowed to stir for 24 hours. Aqueous NaOH (5N, 0.12 mL, 0.6 mmol) is added and the mixture is warmed to 55° C. and allowed to stir for 1 hour. The mixture is acidified with AcOH and purified by preparative HPLC to afford compound 1003 (Table 1).

Example 2C

Preparation of Compound 1031, Table 1

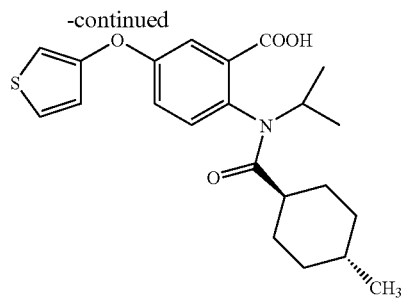

Compound 1031

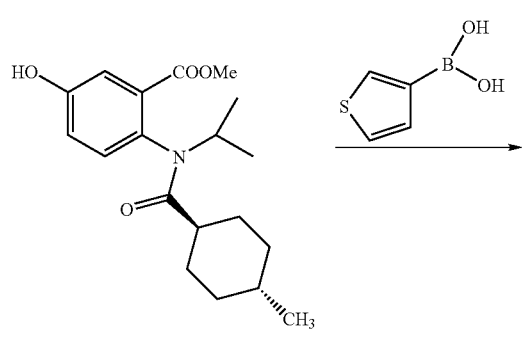

A mixture of phenol 1a9 (Example 1A) (60 mg, 0.18 mmol), 3-thiopheneboronic acid (46 mg, 0.36 mmol), Cu(OAc)₂ (33 mg, 0.18 mmol), Et₃N (0.13 mL, 0.90 mmol) and 4 Å molecular sieves (50 mg) in DCM is stirred for 20 h open to the atmosphere. The mixture is diluted with EtOAc and washed with aqueous 0.2 N HCl, saturated aqueous NaHCO₃ and brine. The organic phase is dried with MgSO₄, filtered and concentrated. The residue is dissolved in DMSO (4 mL) and aqueous NaOH (2.5 N, 1.0 mL, 2.5 mmol) is added. The mixture is allowed to stir 2 hours at ambient temperature, then is acidified with AcOH and purified by preparative HPLC to isolate compound 1031 (Table 1).

Example 2D

Preparation of Compound 2011, Table 2

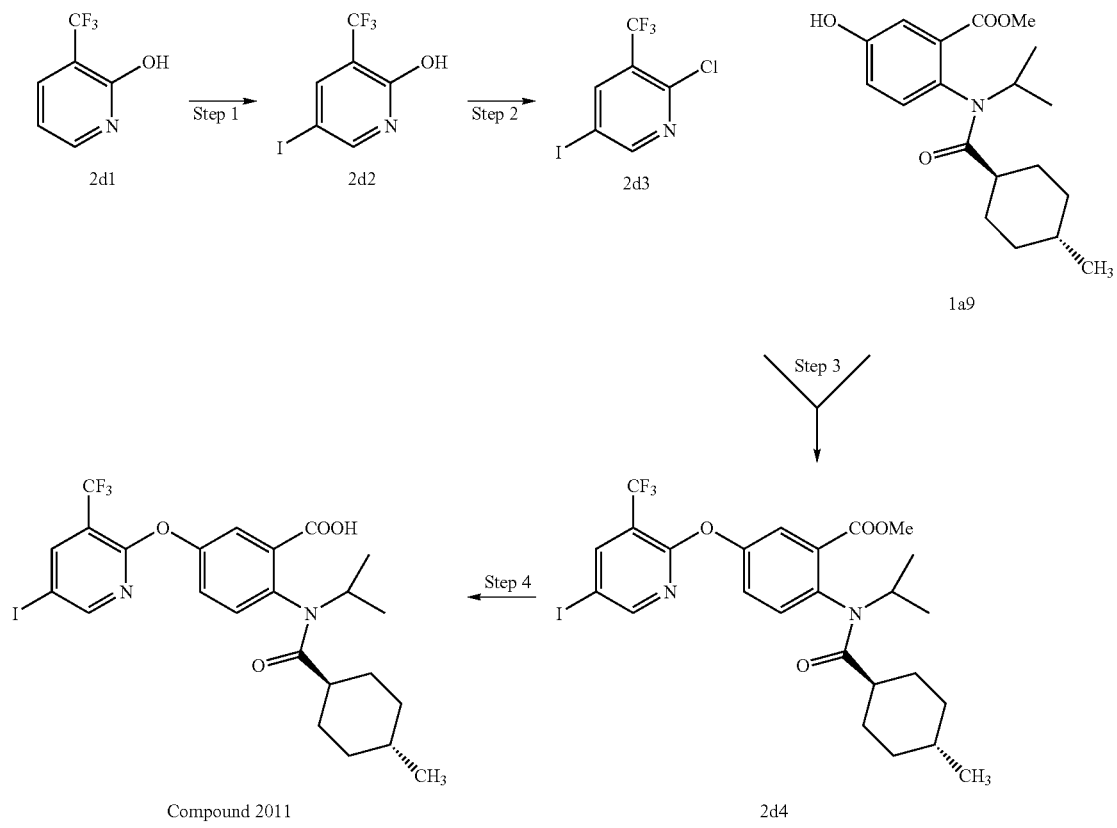

Step 1:

To a mixture of compound 2d1 (39.01 g, 239 mmol) and anhydrous DMF (800 mL) under Ar is added N-iodosuccinimide (4.89 g, 244 mmol) and anhydrous K$_2$CO$_3$ (33.72 g, 244 mmol) and the mixture is allowed to stir at 60° C. for 3 hours. The mixture is cooled to ambient temperature, filtered and concentrated under reduced pressure. The residue is dissolved in DCM (1 L) and the organic phase is washed with brine. The aqueous phase is adjusted to pH 4 by the addition of 2M HCl then extracted with DCM (1 L). The combined organic extracts are washed with brine (2 L) and dried over Na$_2$SO$_4$. The mixture is concentrated to approx 300 mL and cooled overnight in a fridge. The precipitated solid is removed by filtration and dried to provide aryl iodide 2d2.

Step 2:

A mixture of compound 2d2 (115.7 g, 400 mmol) and PhPOCl$_2$ (668.6 g, 343 mmol) under N$_2$ is stirred at 136° C. overnight, then cooled to room temperature and added slowly to 3 L of crushed ice. The aqueous mixture is adjusted to pH 6 and filtered. The aqueous filtrate is extracted with DCM (3 L) then the organic phase is washed with saturated NaHCO$_3$ and brine, dried over Na$_2$SO$_4$, filtered and concentrated to provide compound 2d3.

Step 3:

A mixture of compound 1a9 (Example 1A) (62.7 g, 0.19 mol), compound 2d3 (66.7 g, 0.22 mol), anhydrous K$_2$CO$_3$ (65 g, 0.47 mol) and anhydrous DMSO (250 mL) is heated at 100° C. for 2 hr. The mixture is cooled to RT, filtered and the solid is washed with EtOAc. The filtrate is diluted with EtOAc (4 L), washed with saturated NH$_4$Cl and brine, dried over MgSO$_4$ and concentrated. The residue is purified by flash chromatography on silica gel (95:5 hexane/EtOAc to 7:3 Hexane/EtOAc) to afford biarylether 2d4.

Step 4:

To a mixture of compound 2d4 (125 mg, 0.21 mmol), THF (6.0 mL), MeOH (3.0 mL) and H$_2$O (1.0 mL) is added LiOH (5N, 300 µL, 1.5 mmol) at 0° C. The mixture is allowed to react at 0° C. for 15 minutes, then allowed to stir at room temperature overnight. The mixture is diluted with EtOAc and acidified with 1N HCl, and the organic extract is washed with water and brine, dried (MgSO$_4$) and concentrated to provide compound 2011.

Example 2E

Preparation of Compound 1008, Table 1

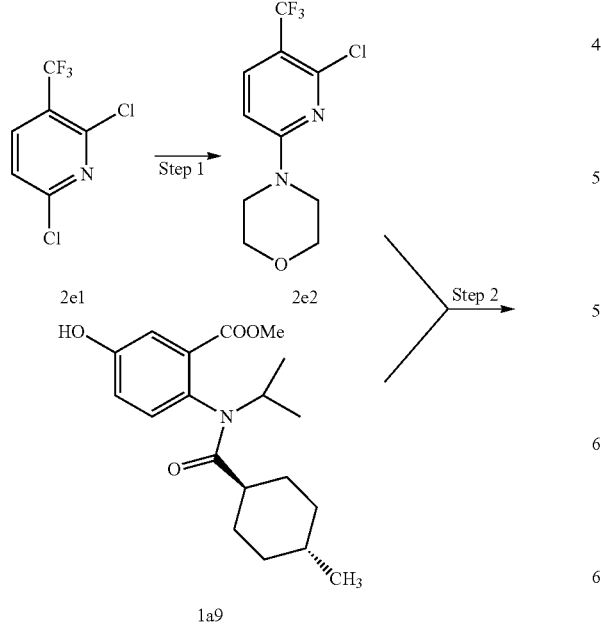

1a9

-continued

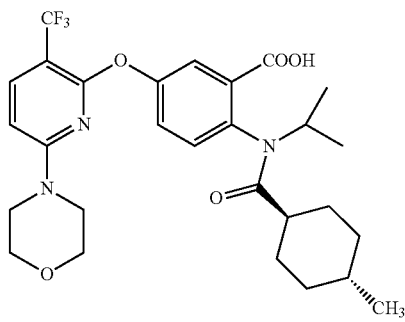

Compound 1008

Step 1:

A mixture of compound 2e1 (64 mg, 0.30 mmol), morpholine (0.027 mL, 0.31 mmol) and triethylamine (0.050 mL, 0.36 mmol) in DMF (1 mL) is stirred overnight at ambient temperature. The mixture is then diluted with EtOAc and successively washed with water (4×) and brine. The organic phase is dried with MgSO$_4$, filtered and concentrated to afford intermediate 2e2.

Step 2:

Intermediate 2e2 and phenol 1a9 (Example 1A) are coupled to synthesize compound (Table 1) using the procedure of Example 2B.

Example 2F

Preparation of Compound 1010, Table 1

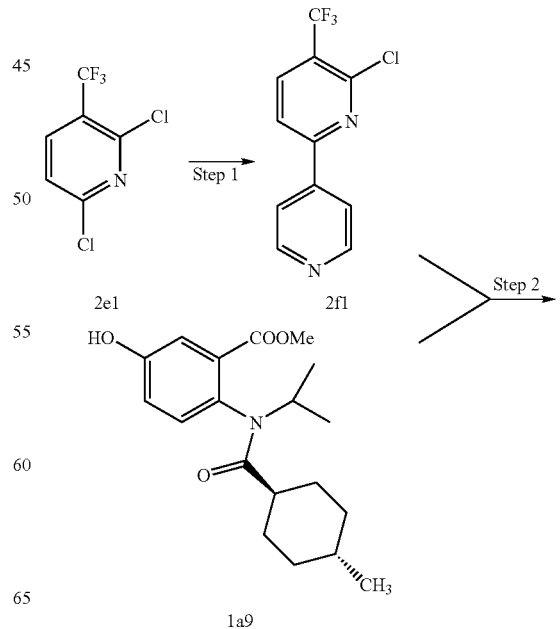

1a9

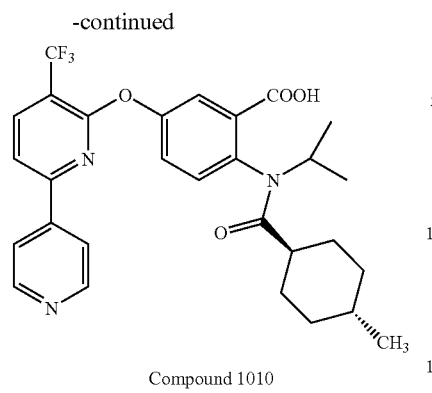

Compound 1010

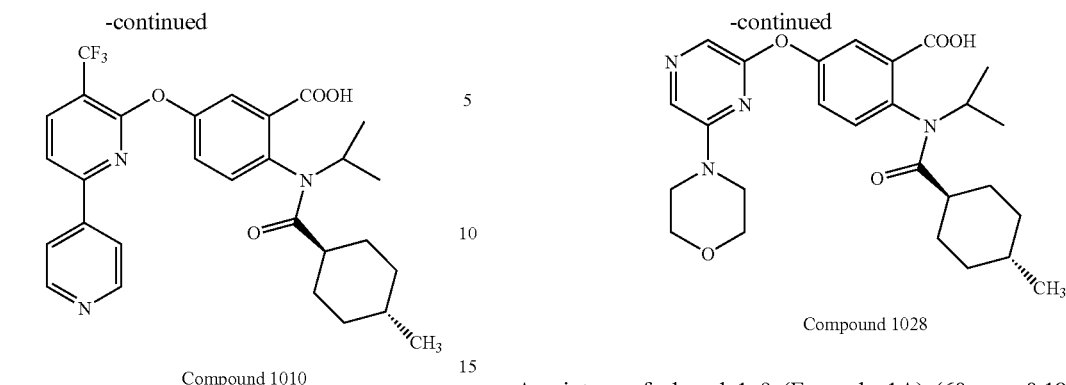

Compound 1028

Step 1:

A mixture of compound 2e1 (Example 2E) (32 mg, 0.15 mmol), 4-pyridylboronic acid (18 mg, 0.15 mmol), $Cs_2CO_3$ (72 mg, 0.22 mmol) and $Pd(PPh_3)_4$ (9 mg, 0.01 mmol) in DMF (1 mL) is degassed and heated at 100° C. overnight. The mixture is poured into water and extracted three times with EtOAc. The combined organic extracts are washed with water (4×) and brine, dried with $MgSO_4$, then passed through a short pad of silica gel, eluting with excess EtOAc. After concentration, the crude product is purified by flash chromatography (15 to 50% EtOAc-hexane) to afford compound 2f1.

Step 2:

Intermediate 2f1 and phenol 1a9 (Example 1A) are coupled to synthesize compound 1010 (Table 1) using the procedure of Example 2B.

Example 3A

Preparation of Compound 1028, Table 1

A mixture of phenol 1a9 (Example 1A) (60 mg, 0.18 mmol), compound 3a1 (22 mg, 0.15 mmol) and $K_2CO_3$ (50 mg, 0.36 mmol) in DMSO (1 mL) is allowed to stir at 100° C. for 20 h. Morpholine (0.031 mL, 0.36 mmol) is added and the mixture is stirred at 100° C. for an additional 20 h. This mixture is allowed to cool to 50° C. and aqueous NaOH (2.5 N, 0.72 mL, 1.8 mmol) is added. After 1 hour, the mixture is acidified with TFA and purified by preparative HPLC to afford compound 1028 (Table 1).

Example 3B

Preparation of Compound 1007, Table 1

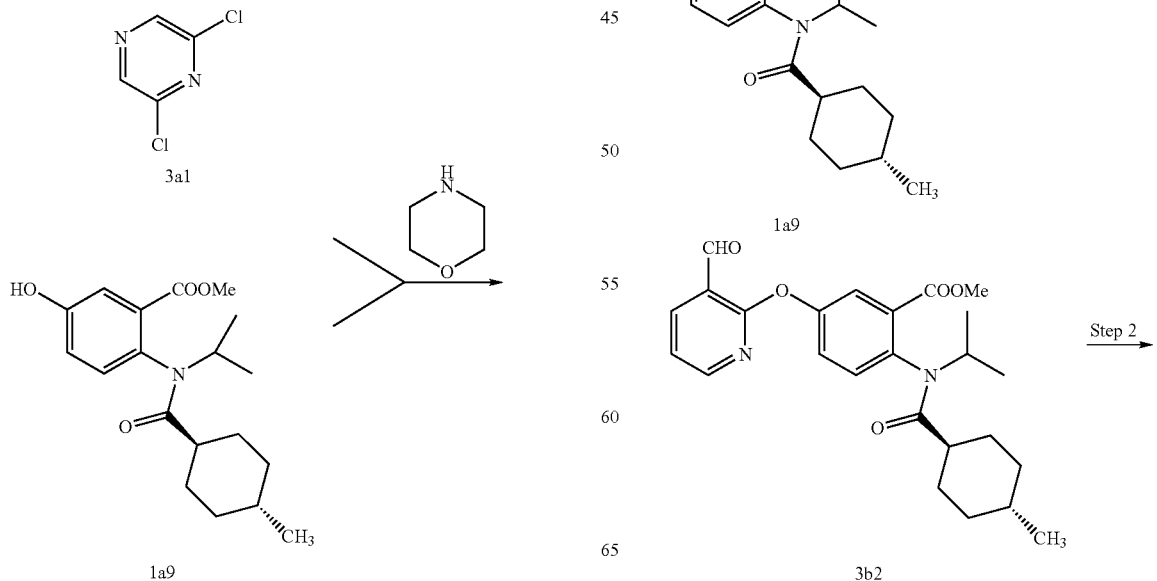

-continued

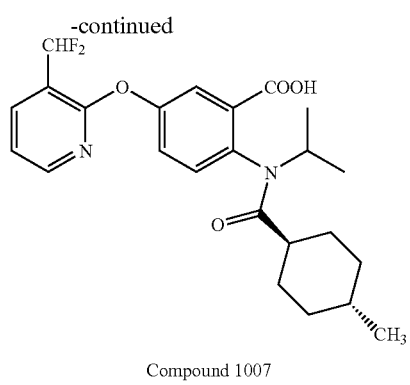

Compound 1007

Step 1:

Phenol 1a9 (Example 1A) (200 mg, 0.60 mmol) and compound 3b1 (90 mg, 0.72 mmol) are combined in DMSO (2 mL). Anhydrous $K_2CO_3$ (200 mg, 1.5 mmol) is added and the mixture is stirred at 100° C. for 1 hour. Further compound 3b1 (50 mg 0.4 mmol) is added and stirring is continued at 100° C. for 45 minutes. The mixture is cooled to ambient temperature, diluted with EtOAc, and washed with water (x2) and brine (x2). The organic phase is dried over NaCl and $Na_2SO_4$, filtered and concentrated in vacuo. Purification by flash chromatography (2:3 EtOAc/hexanes) affords intermediate 3b2.

Step 2:

To a mixture of aldehyde 3b2 (160 mg, 0.36 mmol), Deoxofluor™ (0.12 mL, 0.65 mmol) and anhydrous DCM (1 mL) is added anhydrous MeOH (3 μL, 0.07 mmol, 0.2 eq.) and the mixture is stirred 30 h at ambient temperature. The mixture is diluted with DCM and carefully washed with saturated aqueous $NaHCO_3$. The organic layer is dried over $NaCl/Na_2SO_4$, filtered and concentrated in vacuo. The residue is purified by flash chromatography (2:3 EtOAc/hexane) and a portion of the purified residue (60 mg, 0.1 mmol) is combined with aqueous NaOH (2.5 M, 0.28 mL, 0.7 mmol) in DMSO (1 mL). The mixture is stirred at ambient temperature for 1 hour, then diluted with water (5 mL) and added to rapidly stirred 1N aqueous HCl (100 mL). The resulting solid is collected by suction filtration through a 45 μm filter membrane and dried in vacuo to afford inhibitor 1007 (Table 1).

Example 3C

Preparation of Compound 1029, Table 1

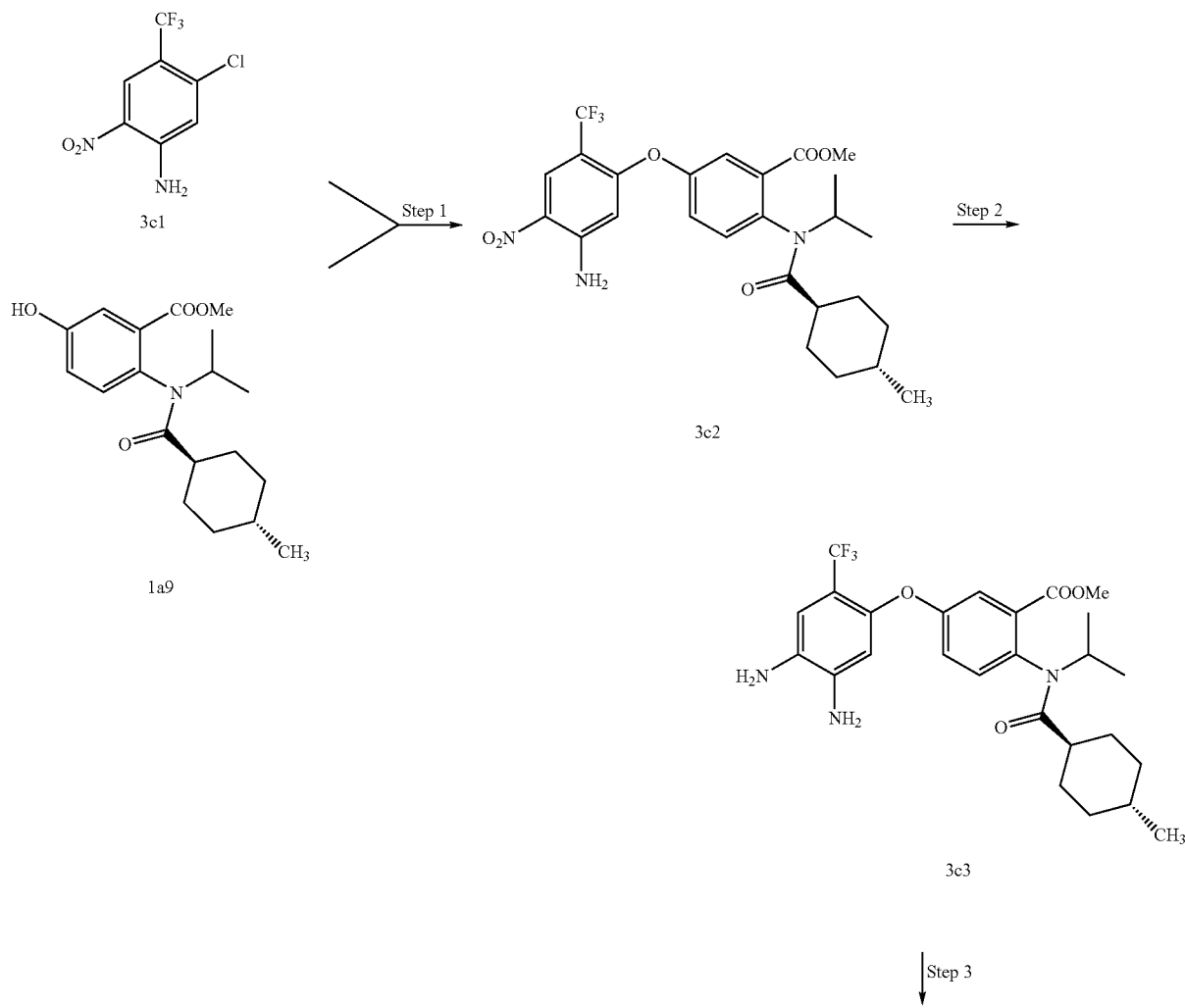

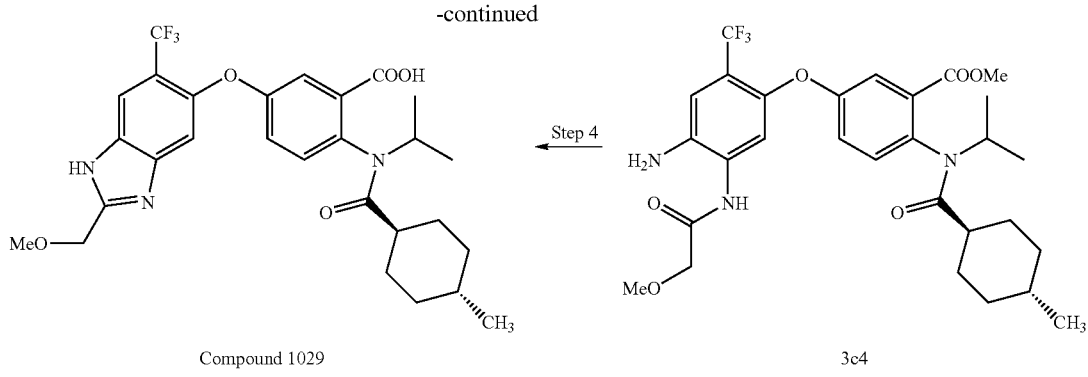

Compound 1029 ← Step 4 ← 3c4

Step 1:

To a mixture of compound 3c1 (38 mg, 0.16 mmol) and dry DMSO (1 mL) is successively added $K_2CO_3$ (55 mg, 0.4 mmol) and phenol 1a9 (Example 1A) (53 mg, 0.16 mmol). The reaction mixture is stirred at 55° C. for 1 h 15 min and then at 70° C. for 16 h. The reaction mixture is poured into water and extracted with EtOAc (3×). The combined organic extract is successively washed with water (4×) and brine, dried with $MgSO_4$, filtered and concentrated to afford intermediate 3c2.

Step 2:

A mixture of compound 3c2 (83 mg, 0.15 mmol) and 10% palladium on carbon (25 mg) in EtOAc (4 mL) is allowed to stir overnight at ambient temperature under 1 atm of $H_2$. The mixture is filtered and concentrated to provide compound 3c3.

Step 3:

To a mixture of dianiline 3c3 (39 mg, 0.08 mmol) and DMF (1 mL) is successively added DIPEA (0.040 mL, 0.23 mmol), 2-methoxyacetic acid (0.006 mL, 0.08 mmol) and HATU (35 mg, 0.09 mmol). The mixture is allowed to stir overnight at ambient temperature, then is diluted with EtOAc and successively washed with 10% aq. citric acid, water, saturated aq. $NaHCO_3$, water and brine. The organic phase is dried with $MgSO_4$, filtered and concentrated to afford intermediate 3c4.

Step 4:

A mixture of compound 3c4 (45 mg, 0.08 mol), methanol (1 mL) and 4 N HCl/dioxane (1 mL) is heated at 75° C. for 1 h. The mixture is concentrated and the residue dissolved in DMSO. Aqueous NaOH (5 N, 0.16 mL, 0.78 mmol) is added and the mixture is stirred for 30 min. at 55° C. then AcOH (300 μL) is added. The mixture is purified by preparative HPLC to isolate compound 1029 (Table 1).

Example 3D

Preparation of Compound 1035, Table 1

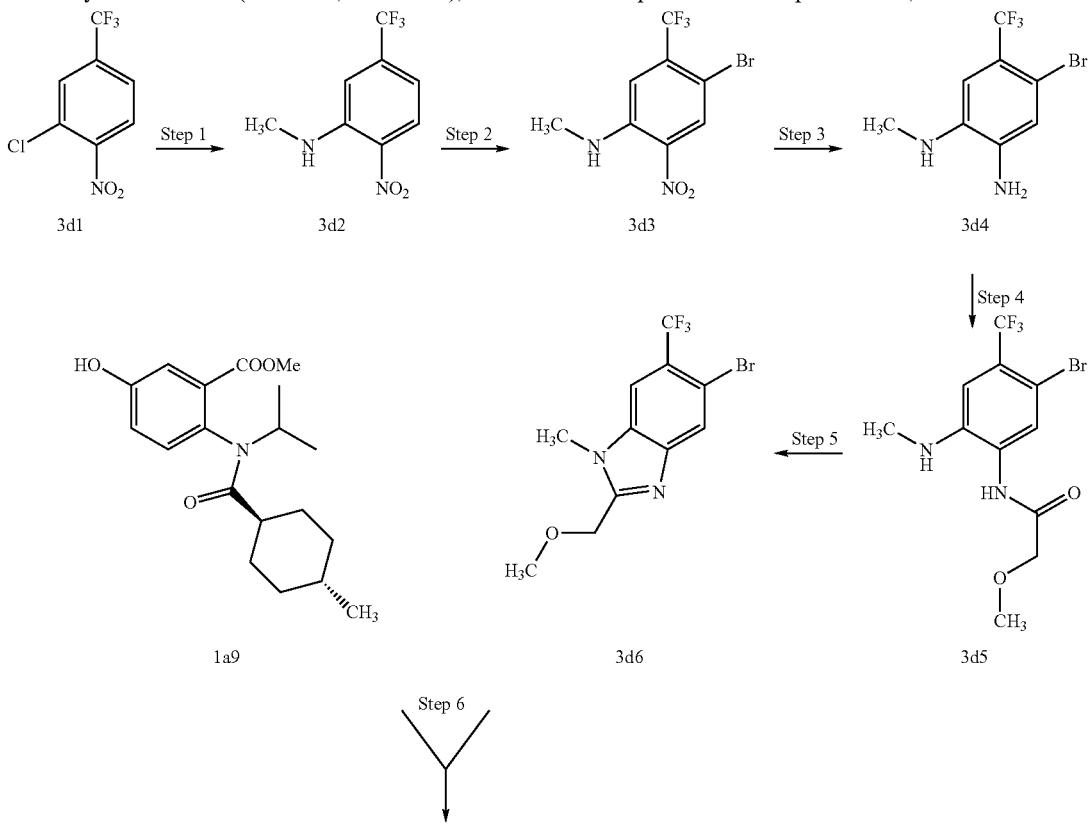

-continued

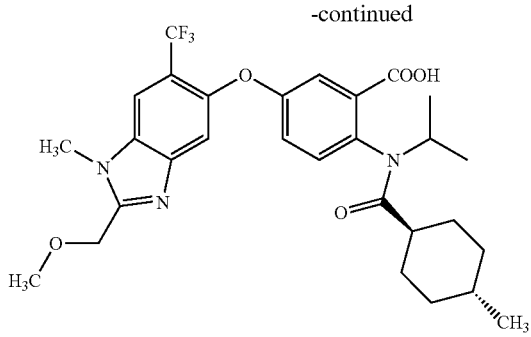

Compound 1035

Step 1:

To a mixture of compound 3d1 (508 mg, 2.3 mmol) and dry DMSO (3 mL) are successively added $CH_3NH_2 \cdot HCl$ (305 mg, 4.5 mmol) and $Et_3N$ (0.79 mL, 5.6 mmol). The reaction mixture is stirred at ambient temperature for 3.5 h and then at 70° C. overnight. The mixture is poured into water and extracted with EtOAc (3×). The combined organic layers are washed with water (4×) and brine, dried with $MgSO_4$, filtered and concentrated. Purification by flash chromatography (2% EtOAc-hexanes) affords compound 3d2.

Step 2:

Bromine (0.012 mL, 0.24 mmol) is added to a mixture of aniline 3d2 (53 mg, 0.24 mmol) and glacial AcOH (0.5 mL). The mixture is heated to 70° C. and allowed to stir 5 hours. Excess $Br_2$ (5 μL, 0.1 mmol) is added and stirring is continued for an additional hour at 70° C. Concentration of the mixture provides compound 3d3.

Step 3:

To a mixture of compound 3d3 (72 mg, 0.24 mmol) and absolute MeOH is added $SnCl_2 \cdot 2H_2O$ (540 mg, 2.4 mmol) and the mixture is heated at reflux for 3 hours, then concentrated. The residue is taken up in EtOAc and poured into saturated aqueous $NH_4Cl$. The aqueous layer is extracted twice more with EtOAc and the combined organic extracts are filtered through a short pad of Celite™. The organic phase is washed with water and brine, dried with $MgSO_4$, filtered and concentrated to afford compound 3d4.

Step 4:

To a mixture of compound 3d4 (60 mg, 0.22 mmol) and DMF (1 mL), are successively added DIPEA (0.12 mL, 0.67 mmol), 2-methoxyacetic acid (0.021 mL, 0.27 mmol) and HATU (100 mg, 0.27 mmol). The reaction mixture is stirred for 6 hours at ambient temperature then diluted with EtOAc and successively washed with 10% aq. citric acid, water, saturated aq. $NaHCO_3$, water and brine. The organic phase is dried with $MgSO_4$, filtered and concentrated to provide compound 3d5.

Step 5:

A mixture of compound 3d5 (76 mg, 0.22 mmol) and glacial AcOH (2 mL) is heated at 60° C. for 6 hours on a J-Kem® orbital shaker (set at 250 rpm). The mixture is concentrated and the residue is purified by flash chromatography (1:1 to 2:1 EtOAc/Hex) to afford benzimidazole 3d6.

Step 6:

The following procedure was adapted from: Elizabeth Buck, E.; Song, Z. J. *Organic Syntheses* 82, 2005, 69.

In a screw cap reaction vessel purged with $N_2$, a mixture of bromobenzimidazole 3d6 (41 mg, 0.13 mmol), phenol 1a9 (Example 1A) (42 mg, 0.13 mmol), CuCl (3 mg, 0.03 mmol), $Cs_2CO_3$ (83 mg, 0.25 mmol) and 2,2,6,6-tetramethylheptane-3,5-dione (0.003 mL, 0.01 mmol) in anhydrous NMP (1 mL) is agitated with a J-Kem® orbital shaker (270 rpm) at 120° C. for a total of 20 hours. The mixture is acidified with AcOH and purified by preparative HPLC to afford compound 1035 (Table 1).

Example 3E

Preparation of Compound 1036, Table 1

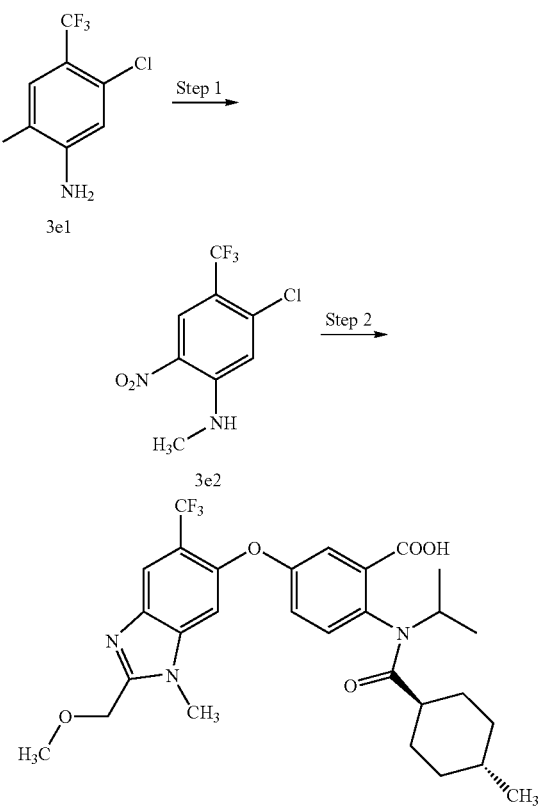

Compound 1036

Step 1:

To a mixture of compound 3e1 (100 mg, 0.45 mmol) and dry DMF (2 mL) are successively added Cs₂CO₃ (218 mg, 0.67 mol) and CH₃I (0.042 mL, 0.67 mmol). The mixture is stirred for 1 hour at ambient temperature, poured into water and extracted with EtOAc. The organic extract is washed with water (4×) and brine, dried with MgSO₄, filtered and concentrated to afford compound 3e2.

Step 2:

Compound 3e2 is converted to compound 1036 (Table 1) using the procedures of Example 3D, steps 3-6.

Example 4A

Preparation of Compound 2010, Table 2

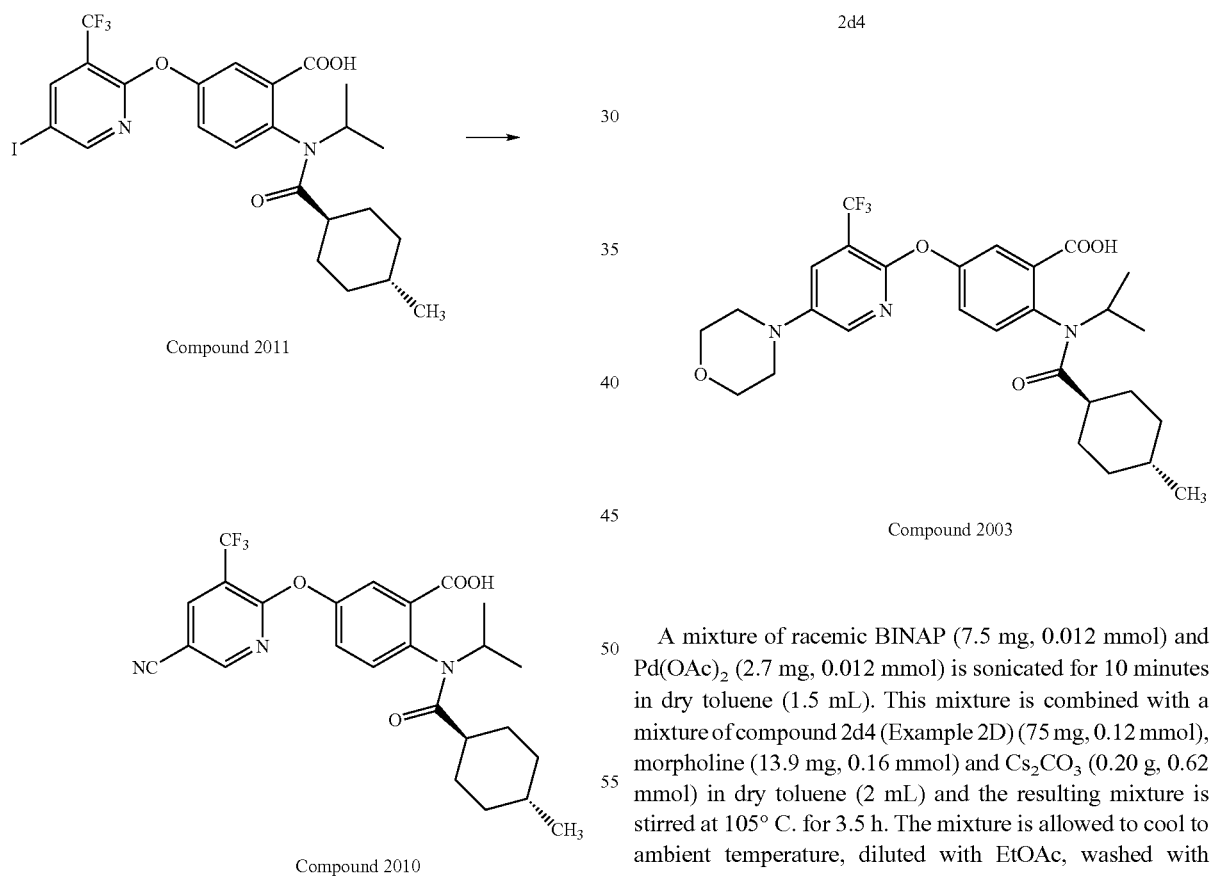

To a mixture of compound 2011 (Example 2D) (40 mg, 0.07 mmol) and anhydrous DMF (2 mL), are added Zn(CN)₂ (16 mg, 0.14 mmol) and Pd(PPh₃)₄ (8.1 mg, 0.01 mmol). The mixture is degassed with Ar and allowed to stir at 110° C. overnight. The mixture is acidified with TFA and purified by preparative HPLC to isolate compound 2010 (Table 2).

Example 4B

Preparation of Compound 2003, Table 2

A mixture of racemic BINAP (7.5 mg, 0.012 mmol) and Pd(OAc)₂ (2.7 mg, 0.012 mmol) is sonicated for 10 minutes in dry toluene (1.5 mL). This mixture is combined with a mixture of compound 2d4 (Example 2D) (75 mg, 0.12 mmol), morpholine (13.9 mg, 0.16 mmol) and Cs₂CO₃ (0.20 g, 0.62 mmol) in dry toluene (2 mL) and the resulting mixture is stirred at 105° C. for 3.5 h. The mixture is allowed to cool to ambient temperature, diluted with EtOAc, washed with water, saturated aqueous NaHCO₃ and brine, dried (MgSO₄) and filtered. The filtrate is concentrated under reduced pressure and the residue mixed with THF (3.0 mL), MeOH (1.5 mL) and H₂O (0.5 mL). Aqueous LiOH (5N, 0.40 mL, 2.0 mmol) is added at 0° C. and the mixture is allowed to stir at ambient temperature overnight. The mixture is acidified with TFA and purified by preparative HPLC to provide compound 2003 (Table 2).

Example 4C
Preparation of Compound 2069, Table 2

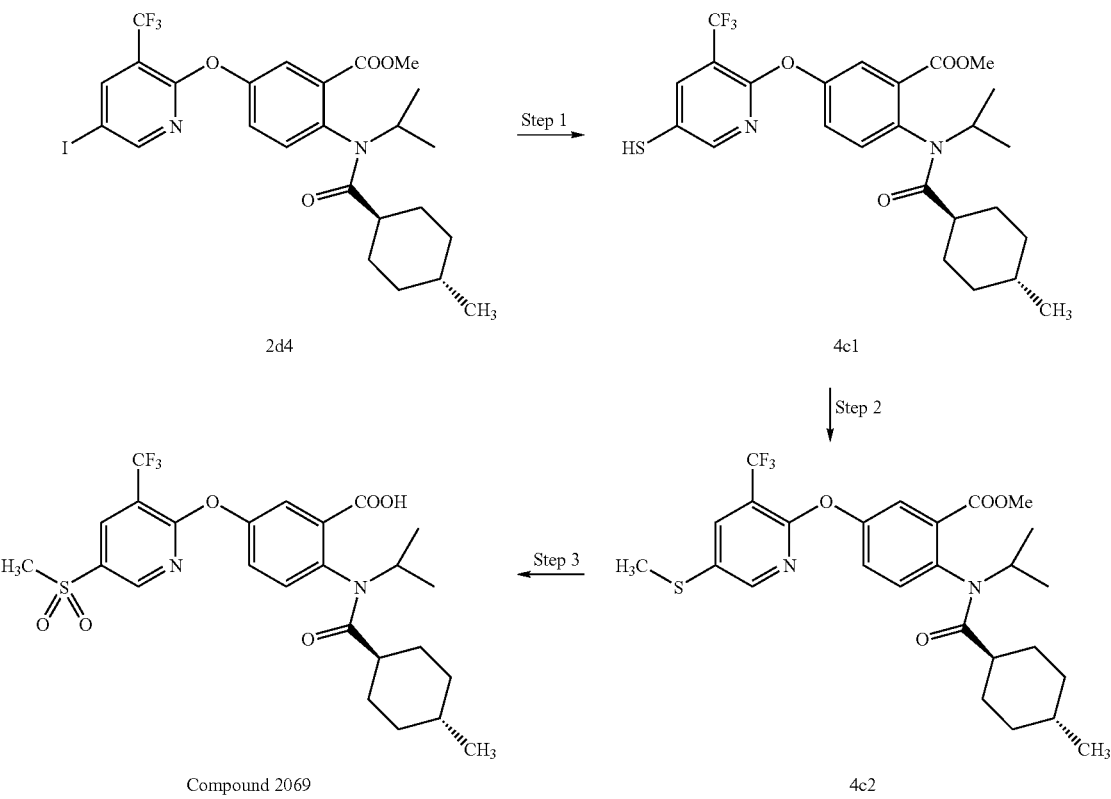

Step 1:

The following procedure is adapted from reference: Takagi, K. *Chem. Lett.* 1985, 1307. To a mixture of iodoarene 2d4 (Example 2D) (270 mg, 0.45 mmol) in anhydrous DMF (2 mL) are added thiourea (54 mg, 0.71 mmol), NiBr$_2$ (11 mg, 0.05 mmol) and NaBH$_3$CN (4.5 mg, 0.07 mmol). The mixture is heated to 120° C. in a microwave for 15 minutes and cooled to ambient temperature and diluted with DMF (3 ml). Aqueous NaOH (0.5 N, 3 mL) is added slowly and the mixture is stirred vigorously for 15 minutes and partitioned between aqueous 1 N HCl and EtOAc. The organic phase is washed with water and brine, dried with MgSO$_4$, filtered and concentrated under reduced pressure to provide compound 4c1.

Step 2:

A mixture of compound 4c1 (205 mg, 0.4 mmol), DBU (0.090 mL, 0.6 mmol) and MeI (0.038 mL, 0.6 mmol) in MeCN (4 mL) is stirred overnight at ambient temperature. The mixture is diluted with EtOAc (50 mL) and washed with 1 N aqueous HCl, water, 1 N aqueous NaOH, water, aqueous thiosulphate and brine. The organic phase is dried with MgSO$_4$, filtered and concentrated under reduced pressure to provide compound 4c2.

Step 3:

Aqueous LiOH (5 N, 0.18 mL, 0.9 mmol) is added to a mixture of methylthioether 4c2 (95 mg, 0.18 mmol) in THF (4 mL), MeOH (2 mL) and water (0.1 mL). The mixture is stirred at ambient temperature for 4 hours then heated to 50° C. for 5 hours and allowed to cool to ambient temperature. The mixture is acidified with 1N HCl, diluted with EtOAc and washed with water and brine. The organic phase is dried with MgSO$_4$, filtered and concentrated under reduced pressure. The residue is taken up in a mixture of acetone and water (5:2; 7 mL), Oxone™ (572 mg, 0.93 mmol) is added and the mixture is stirred at ambient temperature for 2.5 days. The mixture is then diluted with EtOAc and ether (3:2) and washed with 1 N aqueous HCl, water and brine. The organic phase is dried with MgSO$_4$, filtered and concentrated under reduced pressure. The residue is taken up in DMSO and purified by preparative HPLC to afford compound 2069 (Table 2).

Example 5A

Preparation of Compound 2002, Table 2

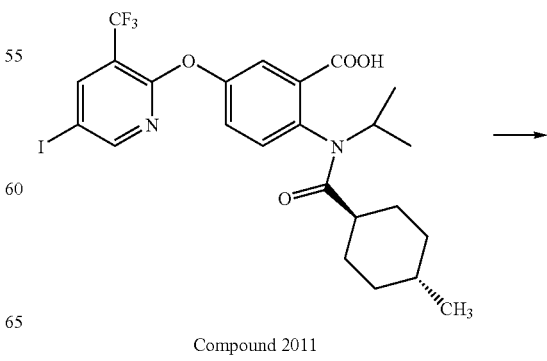

Compound 2011

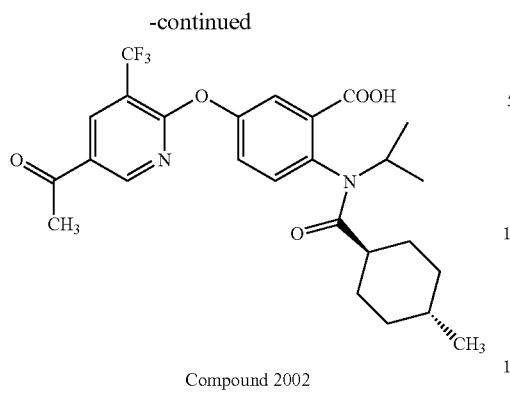

Compound 2002

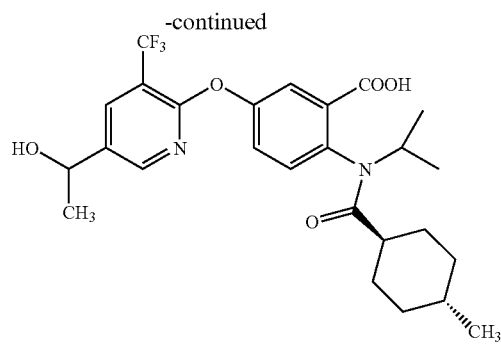

Compound 2004

To a mixture of compound 2011 (Example 2D) (110 mg, 0.19 mmol) in anhydrous DMF (3 mL), is added 1-ethoxyvinyltri-n-butyltin (0.085 mL, 0.25 mmol) and bis(tri-tert-butylphosphino)palladium(0) (9.7 mg, 0.02 mmol). The mixture is degassed with Ar and allowed to stir at 100° C. for 45 minutes. The mixture is allowed to cool to ambient temperature, MeCN (4 mL) and 1N HCl (4 mL) are added and stirring is continued at ambient temperature for 15 minutes. The mixture is concentrated under reduced pressure and DMSO (4 mL) is added to the resulting residue. The mixture is filtered and purified by preparative HPLC to isolate compound 2002 (Table 2).

Example 5B

Preparation of Compound 2004, Table 2

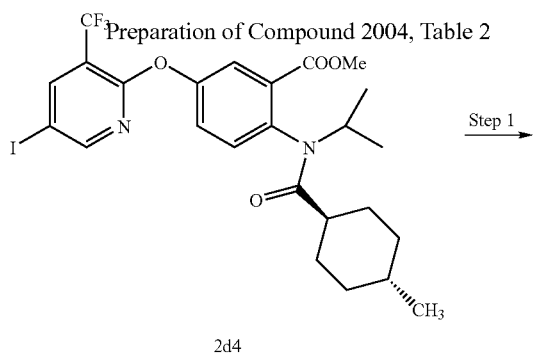

Step 1:
Intermediate 5b1 was prepared from compound 2d4 (Example 2D) utilizing the procedure described in Example 5A.

Step 2:
NaBH$_4$ (9.1 mg, 0.24 mmol) is slowly added to a mixture of compound 5b1 (50 mg, 0.10 mmol) and MeOH (6 mL), and the mixture is stirred at ambient temperature overnight. The mixture is diluted with EtOAc and washed with 1N HCl, water, saturated aqueous NaHCO$_3$ and brine, dried with MgSO$_4$, filtered and concentrated under reduced pressure. The residue is mixed with THF (2 mL), MeOH (1 mL) and water (0.5 mL), and aqueous LiOH (5 N, 0.20 mL, 1.0 mmol) is added. The mixture is allowed to stir overnight at ambient temperature, then is acidified with TFA and concentrated. DMSO (2 ml) is added to the residue and purification of the mixture by preparative HPLC affords compound 2004 (table 2).

Example 5C

Preparation of Compound 2154, Table 2

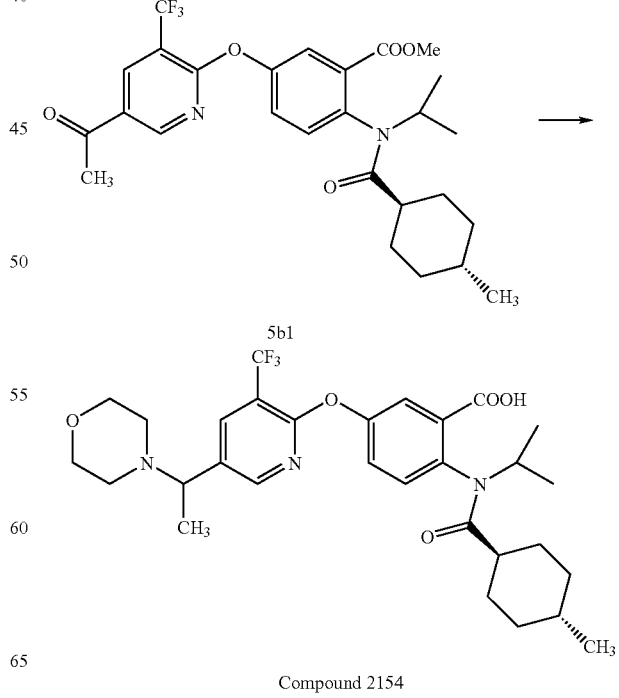

Compound 2154

A mixture of compound 5b1 (Example 5B) (48 mg, 0.09 mmol), NaBH₄ (5.3 mg, 0.14 mmol), AcOH (0.050 mL, 0.88 mmol) and morpholine (0.010 mL, 0.11 mmol) in EtOH (1 mL) is heated for 20 hours at 60° C. Excess NaBH₄ (2 mg, 0.05 mmol) and morpholine (0.017 mL, 0.18 mmol) are added and stirring is continued for an additional 20 hours at 60° C. Aqueous NaOH (2.5 N, 0.60 mL, 1.5 mmol) is added and the mixture is stirred for 1 hour at 50° C. After acidification with AcOH, the mixture is purified by preparative HPLC to isolate compound 2154 (Table 2).

Example 6A

Preparation of Compound 2103, Table 2 ambient temperature and concentrated under reduced pressure. The residue is purified by flash chromatography (1:1 EtOAc/Hex) to afford compound 6a1.

Step 2:

To a mixture of compound 6a1 (900 mg, 1.7 mmol) in CH₂Cl₂ (24 mL) is added oxalyl chloride (0.21 mL, 2.4 mmol) and DMF (0.060 mL, 0.8 mmol) and the mixture is allowed to stir for 1 hour at room temperature. The mixture is concentrated and the residue is taken up in CH₂Cl₂ (30 mL). CH₂N₂ (0.35 M in Et₂O, 46 mL, 16 mmol) is added dropwise with stirring and stirring is continued for 30 minutes. The mixture is concentrated under reduced pressure and the residue is taken up in THF (24 mL). 48% aqueous HBr (1.8 mL, 16 mmol) is added and the mixture is allowed to stir for 20

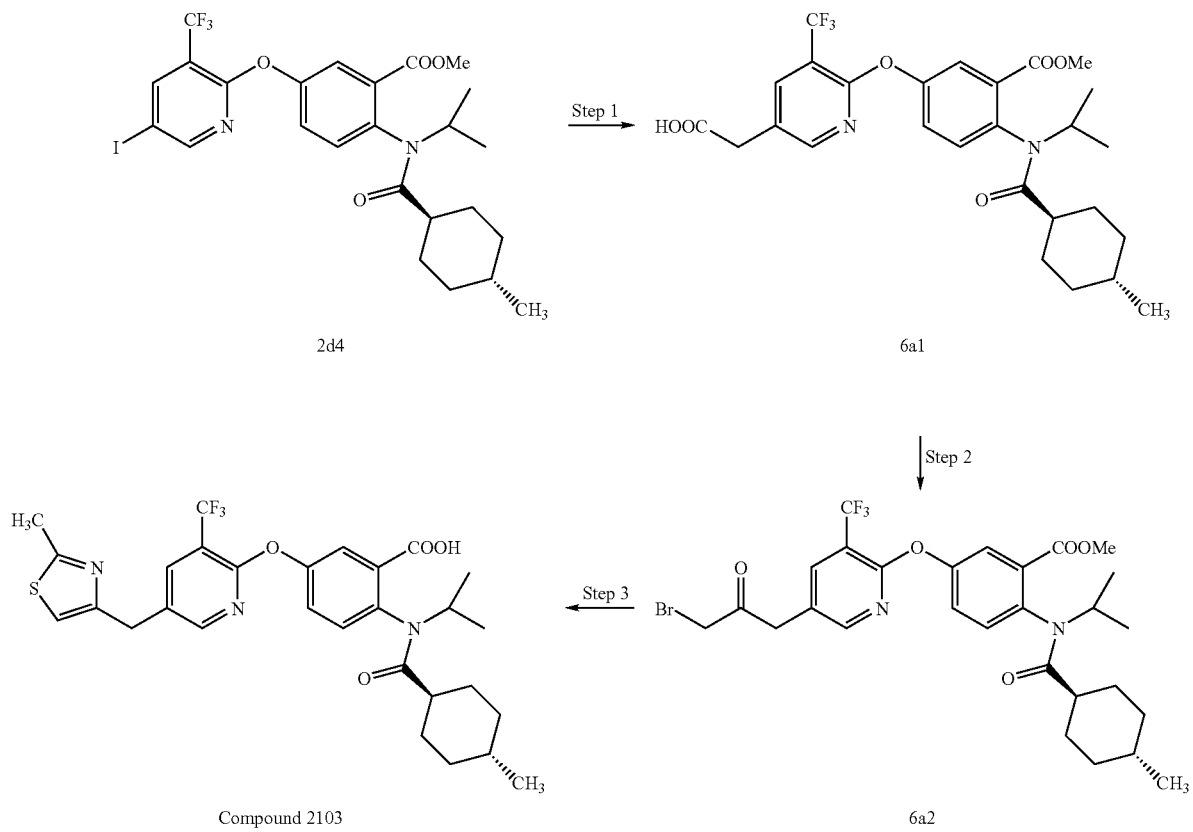

Step 1:

The procedure is adapted from a protocol described in: Hennessy, E. J.; Buchwald, S. L. Org. Lett. 2002, 4, 269.

A mixture of compound 2d4 (Example 2D) (2.0 g, 3.3 mmol), dibenzyl malonate (2.5 g, 9.9 mmol), CuI (76 mg, 0.4 mmol), 2-phenylphenol (68 mg, 0.4 mmol), Cs₂CO₃ (4.1 g, 12.5 mmol) in anhydrous THF (30 mL) is degassed with Ar 15 minutes, then stirred at 70° C. for 16 hours. Excess CuI (76 mg, 0.4 mmol) and 2-phenylphenol (68 mg, 0.4 mmol) are added and stirring is continued at 70° C. for an additional 20 hours. The mixture is diluted in EtOAc, washed with saturated aqueous NH₄Cl and brine, and concentrated. The residue is taken up in EtOH (20 mL) and 10% Pd/C (0.4 g) is added. The mixture is stirred under 1 atm of H₂ for 2 hours at ambient temperature and filtered through a pad of Celite™. The filtrate is stirred at 80° C. for 1 hour, allowed to cool to minutes. The mixture is concentrated under reduced pressure and diluted with EtOAc. The organic phase is washed with water, saturated aqueous NaHCO₃ and brine, dried over MgSO₄, filtered and concentrated under reduced pressure to provide compound 6a2.

Step 3:

A mixture of bromoketone 6a2 (60 mg, 0.1 mmol) and thioacetamide (14 mg, 0.19 mmol) in i-PrOH is allowed to stir at 70° C. for 1 hour. The mixture is allowed to cool to ambient temperature and NaOH (2.5 N, 0.18 mL, 0.44 mmol) is added. The mixture is stirred at 40° C. for 5 hours, then diluted with water and acidified with HCl. The solid is collected by filtration and washed with excess water, then taken up in DMSO and purified by preparative HPLC to afford compound 2103 (Table 2).

Example 7A

Preparation of Intermediate 7a5

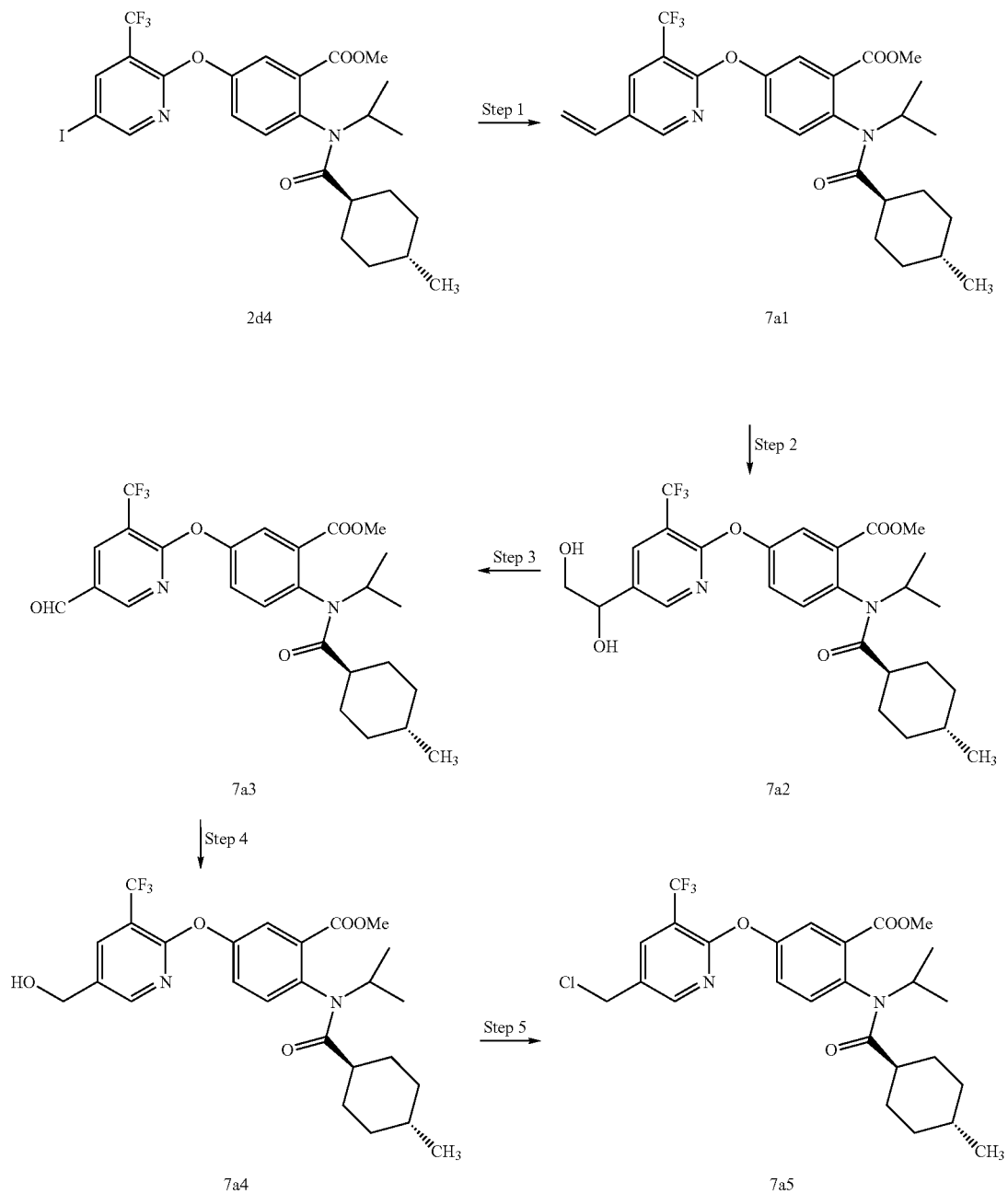

Step 1:

To a mixture of compound 2d4 (Example 2D) (40 g, 66.2 mmol) in anhydrous THF (280 mL) are added vinyltributyltin (23 mL, 25 g, 78.8 mmol) and $PdCl_2(PPh_3)_2$ (4.8 g, 6.8 mmol). The mixture is degassed with Ar for 5 minutes, then heated at reflux for 4-6 hours. The solvent is removed under reduced pressure and the residue is purified by flash chromatography (gradient from 19:1 to 3:2 Hexane/EtOAc) to afford intermediate 7a1.

Step 2:

To a solution of the alkene 7a1 (40.3 g, 79.9 mmol) in acetone (710 mL) are added tert-BuOH (176 mL), water (88 mL), 4-N-methylmorpholineoxide monohydrate (60% solution in water, 21 mL, 120 mmol) and $OSO_4$ (2.5 wt % in t-BuOH, 13.3 mL, 1.06 mmol). The mixture is stirred overnight at ambient temperature, then is concentrated and taken up in EtOAc (4 L). The organic phase is washed with 2M HCl (2×1 L), water, saturated aqueous $NaHCO_3$ (1 L) and brine.

Activated carbon and Na₂SO₄ are added to the organic phase and the mixture is stirred for 10 minutes. The mixture is filtered through a pad of Celite™ then concentrated to afford intermediate 7a2.

Step 3:

Sodium periodate (25 g, 116.9 mmol) is added to a chilled (0° C.) mixture of the diol 7a2 (40.6 g, 75.4 mmol) in THF (710 mL) and water (270 mL). The mixture is left 5 minutes at 0° C., then stirring is continued at room temperature for 4 h. Additional sodium periodate (3.3 g, 15.4 mmol, 0.2 eq) is added and stirring is continued for 2 hours. The mixture is diluted with ether/EtOAc (1.8 L/3.6 L) then washed with water and brine, dried over Na₂SO₄, filtered and concentrated under reduced pressure. The residue is purified by flash chromatography to afford intermediate 7a3.

Step 4:

Sodium borohydride (4.4 g, 116 mmol, 2 eq) is added slowly to a mixture of aldehyde 7a3 (30.7 g, 60.6 mmol) and MeOH (300 mL). The mixture is stirred for 2 hours at ambient temperature, then diluted with EtOAc and carefully washed with 1N HCl, saturated aqueous NaHCO₃ and brine. The organic phase is dried over Na₂SO₄, filtered and concentrated under reduced pressure to afford intermediate 7a4.

Step 5:

Thionyl chloride (5.5 mL, 8.1 mmol) is added slowly to a mixture of alcohol 7a4 (19 g, 37.4 mmol), anhydrous CH₂Cl₂ (450 mL) and DMF (9 mL). The mixture is stirred 30 minutes at ambient temperature, then diluted with EtOAc (1.5 L) and washed with saturated aqueous NaHCO₃ and brine. The organic phase is dried with Na₂SO₄, filtered and concentrated to give intermediate 7a5.

Example 8A

Preparation of Compound 2005, Table 2

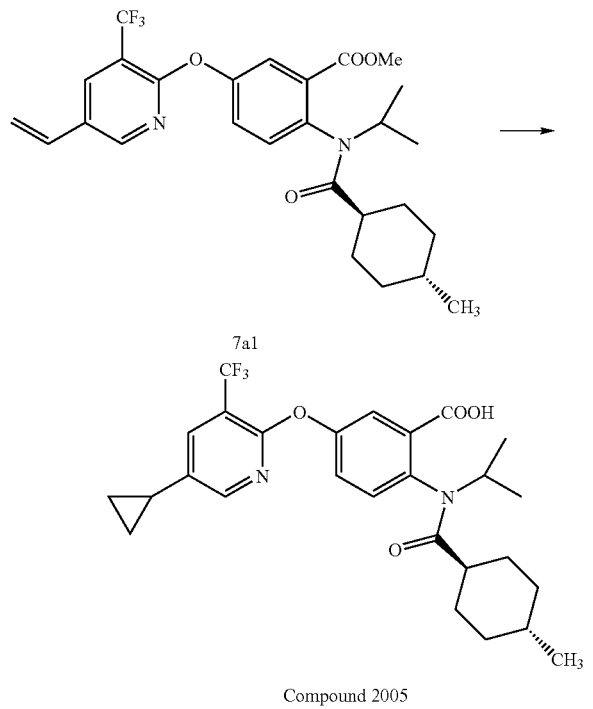

Compound 2005

Diazomethane in ether (4 mL) is slowly added to a chilled (0° C.) mixture of alkene 7a1 (Example 7A) (26 mg, 0.05 mmol) in ether (2 mL). Pd(OAc)₂ (2 mg, 0.01 mmol) is added and the mixture is stirred at ambient temperature for 1.5 hours. The mixture is concentrated under reduced pressure, and THF (2 mL), MeOH (1 mL) and water (0.2 mL) are added to the residue followed by aqueous LiOH (5 N, 0.6 mL, 3.0 mmol). The mixture is stirred at ambient temperature for 2.5 days. DMSO (1.5 mL) and excess aqueous LiOH (5 N, 0.3 mL, 1.5 mmol) are added and stirring is continued at ambient temperature overnight. The mixture is acidified with TFA and concentrated under reduced pressure. The residue is purified by preparative HPLC to isolate compound 2005 (Table 2).

Example 8B

Preparation of Compound 2007, Table 2

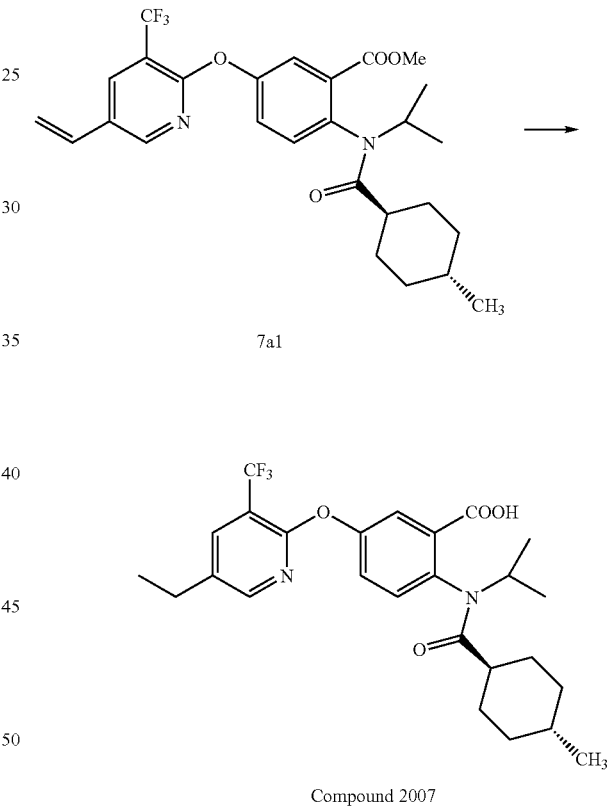

Compound 2007

To a mixture of alkene 7a1 (Example 7A) (23 mg, 0.05 mmol) in MeOH (2 mL) and EtOAc (4 mL) is added 10% palladium on carbon (2 mg). The mixture is stirred for 2.5 days under H₂ (~1 atm), then filtered and concentrated to dryness. The residue is taken up in THF (2 mL), MeOH (1 mL) and water (0.2 mL). Aqueous LiOH (5 N, 0.4 mL, 2.0 mmol) is added and the mixture is stirred at ambient temperature overnight. DMSO (1.0 mL) and excess aqueous LiOH (5 N, 0.2 mL, 1.0 mmol) are added and stirring is continued at 50° C. for 3 hours. The mixture is acidified with TFA and concentrated under reduced pressure. The residue is purified by preparative HPLC to isolate compound 2007 (Table 2).

Example 9A

Preparation of Compound 2120, Table 2

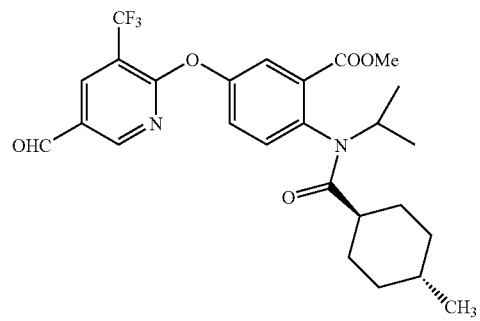

7a3

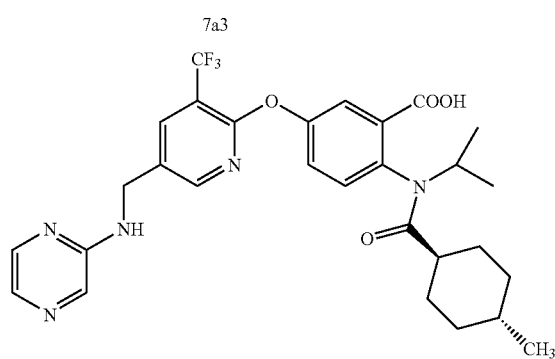

Compound 2120

A mixture of aldehyde 7a3 (Example 7A) (50 mg, 0.1 mmol) and 2-aminopyrazine (38 mg, 0.4 mmol) in AcOH (0.5 mL) is stirred at 80° C. for 2 hours. The mixture is allowed to cool to ambient temperature, NaCNBH$_3$ (7.9 mg, 0.13 mmol) is added and the mixture is stirred for 15 minutes, then concentrated under a stream of N$_2$. Aqueous NaOH (2.5N, 0.60 mL, 1.5 mmol) is added to the residue and the mixture is allowed to stir at 50° C. for 2 hours, then purified by preparative HPLC to isolate compound 2120 (Table 2).

Example 10A

Preparation of Compound 2026, Table 2

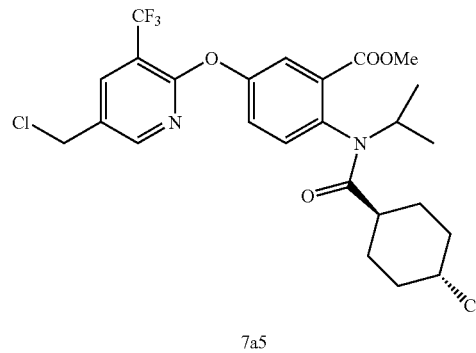

7a5

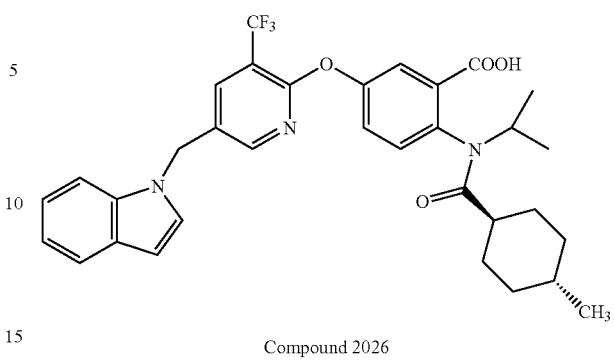

Compound 2026

A mixture of intermediate 7a5 (Example 7A) (25 mg, 0.05 mmol), indole (8.2 mg, 0.07 mmol), Cs$_2$CO$_3$ (23 mg, 0.07 mmol) and KI (3 mg, 0.02 mmol) in DMF (1 mL) is agitated on a J-Kem® orbital shaker (250 rpm) at 70° C. overnight. DMSO (0.5 mL) is added followed by aqueous NaOH (5 N, 0.10 mL, 0.5 mmol) and the mixture is stirred at 55° C. for 1 hour. The mixture is acidified with AcOH, then purified by preparative HPLC to isolate compound 2026 (Table 2).

Example 10B

Preparation of Compounds 2047 and 2057, Table 2

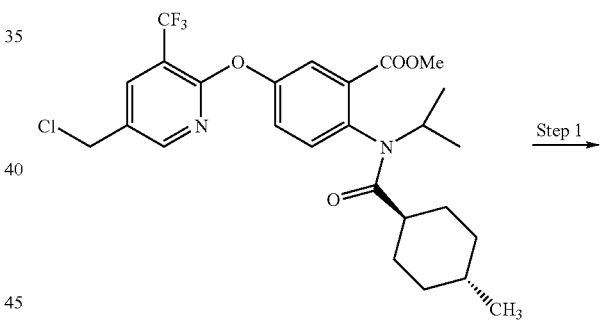

7a5

Step 1

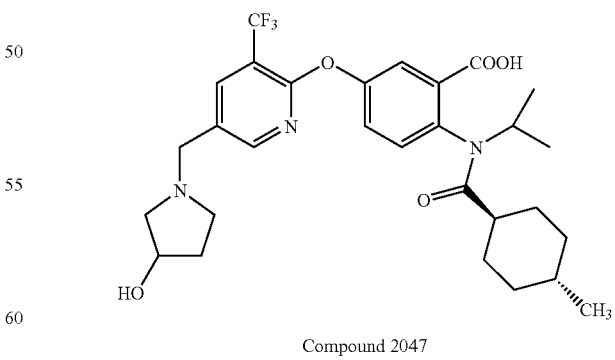

Compound 2047

Step 2

-continued

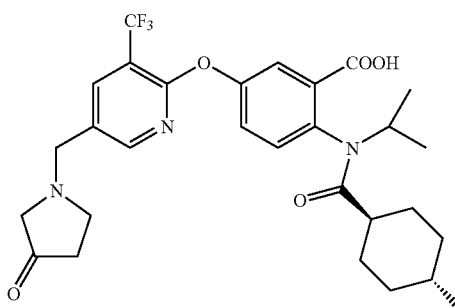

Compound 2057

Step 1:

A mixture of compound 7a5 (Example 7A) (25 mg, 0.05 mmol), 3-pyrrolidinol (0.006 mL, 0.07 mmol) and Et₃N (0.010 mL, 0.07 mmol) in THF (1 mL) is agitated on a J-Kem® orbital shaker (250 rpm) at 70° C. overnight. The mixture is concentrated under a stream of N₂ then taken up in DMSO (0.5 mL). Aqueous NaOH (5 N, 0.10 mL, 0.5 mmol) is added and the mixture is stirred at 55° C. for 1 hour. The mixture is acidified with AcOH and purified by preparative HPLC to isolate compound 2047 (Table 2).

Step 2:

A mixture of compound 2047 (12 mg, 0.02 mmol) and Dess-Martin periodinane (7.6 mg, 0.02 mmol) in DCM/CH₃CN (1:1, 1 mL) is stirred at ambient temperature for 20 hours. An additional portion of Dess-Martin periodinane (7.6 mg, 0.02 mmol) is added and is stirring is continued for a further 20 hours. The mixture is concentrated under reduced pressure and the residue is purified by preparative HPLC to afford compound 2057 (Table 2).

Example 10C

Preparation of Compound 2153 (Table 2)

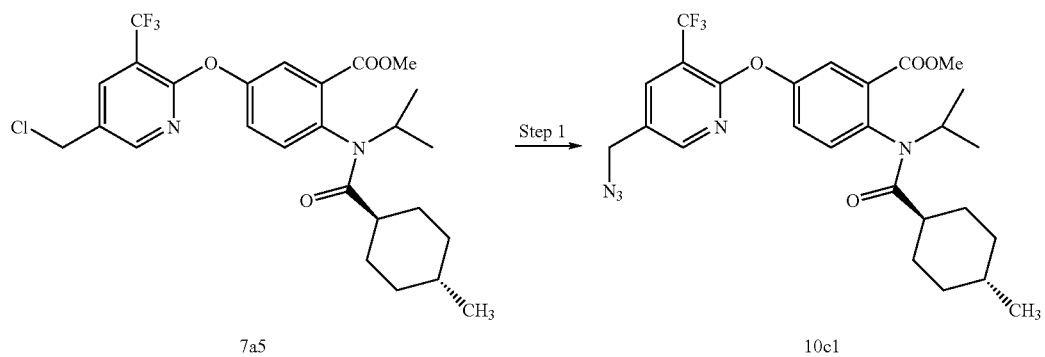

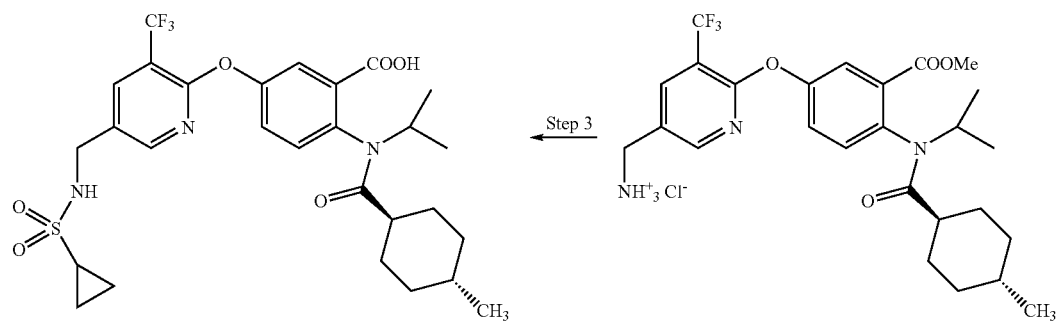

Step 1:

A mixture of compound 7a5 (Example 7A) (9.5 g, 18.05 mmol), NaN$_3$ (2.16 g, 33.4 mmol) and 60% (v/v) acetone-water (90 mL) is stirred at reflux under Ar overnight. The mixture is concentrated under reduced pressure and the residue is extracted with EtOAc (1 L) and washed with water (4×). The organic phase is dried over MgSO$_4$, filtered and concentrated under reduced pressure to provide compound 10c1.

Step 2:

Argon is bubbled though a mixture of compound 10c1 (9.68 g, 18.14 mmol) in methanol (100 mL) for 10 minutes and the mixture is added to Pd/C (10%, 1 g) under Ar. H$_2$ is bubbled through the stirred mixture for 2.5 hours. The mixture is filtered through Celite™ and rinsed with MeOH. The filtrate is concentrated to dryness and the residue is purified by flash column chromatography (SiO$_2$, MeOH/DCM: 5/95) to isolate the free amine. A mixture of the amine and 2M HCl solution in Et$_2$O (30 mL) is stirred at room temperature for 1 hour. The hydrochloride salt 10c2 is collected by filtration, rinsed with diethyl ether and air dried.

Step 3:

To a mixture of compound 10c2 (25 mg, 0.049 mmol) and DMF (0.50 mL) is added cyclopropanesulfonyl chloride (6.3 µL, 0.058 mmol) and Et$_3$N (16.9 µL, 0.121 mmol). The mixture is agitated on an orbital shaker (350 rpm) overnight at room temperature. NaOH (5N, 100 µL, 0.50 mmol) is added, the mixture is heated at 50° C. for 1 h, then acidified with AcOH and purified by preparative HPLC to give compound 2153 (Table 2).

Example 10D

Preparation of Compound 2159 (Table 2)

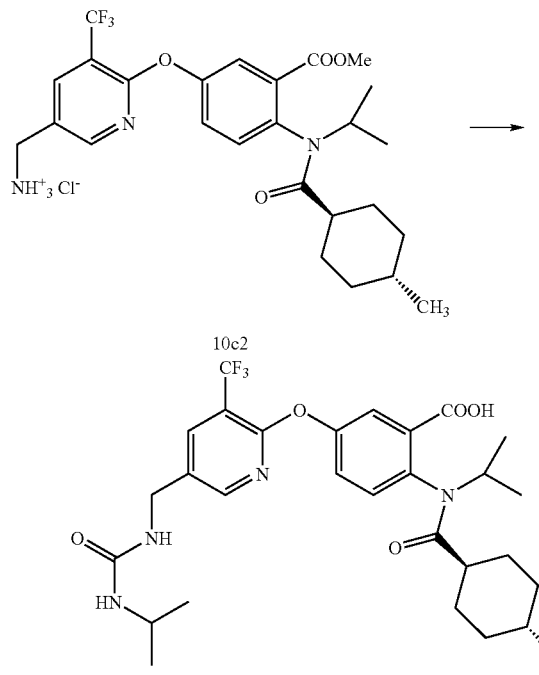

Compound 2159

To a mixture of compound 10c2 (Example 10C) (25 mg, 0.046 mmol, 1 equivalent) in DMF (0.5 mL) is added (CH$_3$)$_2$CH—NCO (1.3 equivalents). The mixture is stirred at room temperature until complete as determined by HPLC analysis. 5N NaOH (0.1 mL, 10 equivalents) is added and the mixture is heated to 50° C. for 1 h, then acidified with AcOH. Purification by reversed-phase HPLC provides compound 2159 (Table 2).

Example 10E

Preparation of Compound 2161 (Table 2)

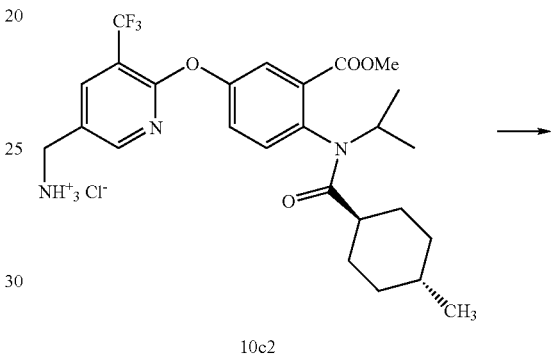

10c2

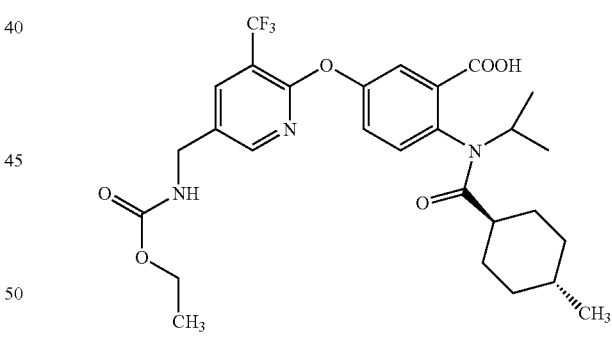

Compound 2161

To a mixture of compound 10c2 (Example 10C) (25 mg, 0.046 mmol, 1 equivalent) in THF (0.5 mL) is added DIEA (12 µL, 1.5 equivalents) followed by ethyl chloroformate (5.3 µL, 1.2 equiv.). The mixture is stirred at room temperature overnight, then concentrated under reduced pressure. The residue is mixed with DMSO (0.5 mL), 5N NaOH (0.1 mL, 11 equivalents) is added and the mixture is heated at 50° C. for 45 min. The mixture is acidified using AcOH and purified by reversed-phase HPLC to provide compound 2161 (Table 2).

Example 10F

Preparation of Compound 2188 (Table 2)

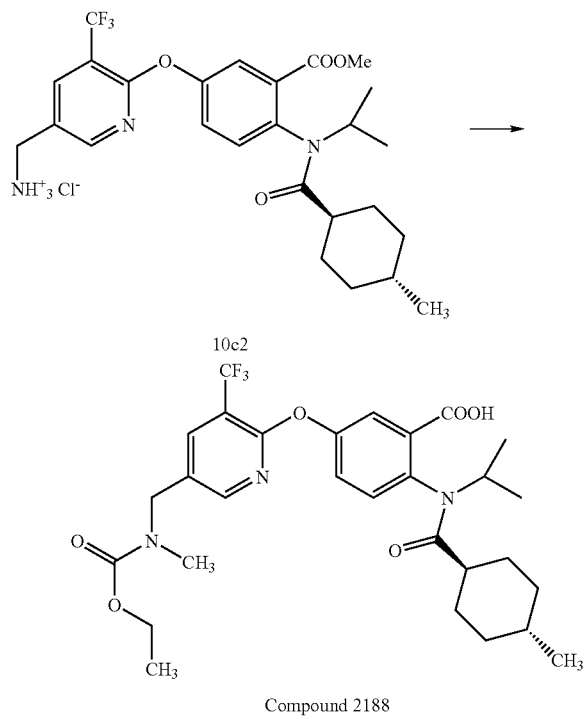

Compound 2188

To a mixture of compound 10c2 (Example 10C) (50 mg, 0.091 mmol) and DCM (1 mL) is added ethyl chloroformate (12 µL, 0.126 mmol) followed by Et₃N (40 µL, 0.287 mmol). The reaction mixture is stirred at room temperature overnight and concentrated under a stream of argon, and the residue is mixed with DMF (1 mL).

Half of the mixture is added to a vial containing NaH (60% oil dispersion, 6 mg, 3.3 equiv.) and the mixture is stirred for 5 min at room temperature. Iodomethane (10 µL, 3.5 equiv.) is added and stirring is continued at room temperature for 5 h. 5N NaOH (10 equiv.) is added and the mixture stirred an additional 14 h at room temperature and purified by preparative HPLC to provide compound 2188 (Table 2).

Example 11A

Preparation of Compound 2039, Table 2

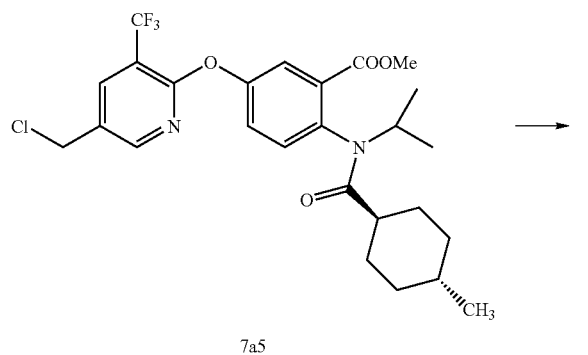

7a5

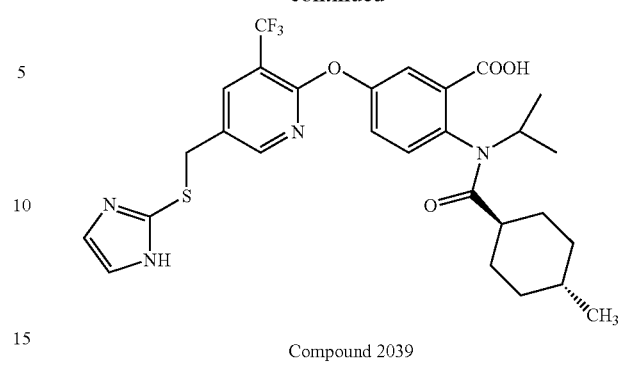

Compound 2039

A mixture of intermediate 7a5 (Example 7A) (25 mg, 0.05 mmol), 2-mercaptoimidazole (7.0 mg, 0.07 mmol), Cs₂CO₃ (23 mg, 0.07 mmol) and DMF (1 mL) is agitated on a J-Kem® orbital shaker (250 rpm) at 70° C. overnight. DMSO (0.5 mL) is added followed by aqueous NaOH (5 N, 0.10 mL, 0.5 mmol) and the mixture is stirred at 55° C. for 1 hour. The mixture is acidified with AcOH, then purified by preparative HPLC to isolate compound 2039 (Table 2).

Example 11B

Preparation of Compound 2071, Table 2

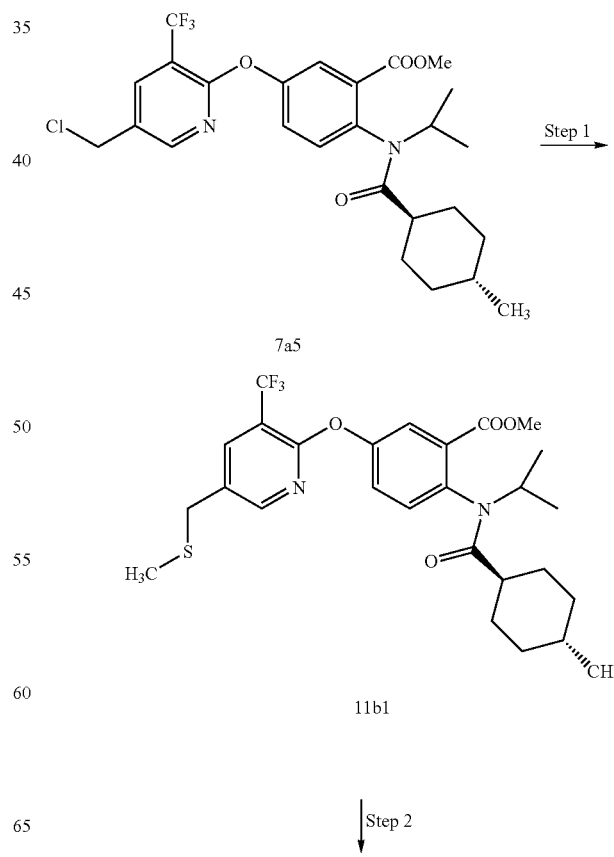

-continued

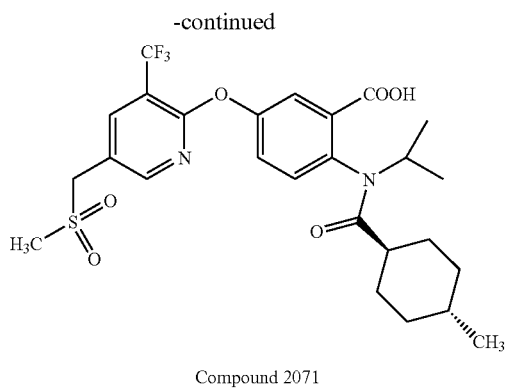

Compound 2071

Step 1:

A mixture of intermediate 7a5 (Example 7A) (55 mg, 0.1 mmol), KI (3 mg, 0.02 mmol), NaSMe (11 mg, 0.16 mmol) and Et₃N (0.031 mL, 0.23 mmol) in anhydrous DMF (1.5 mL) is stirred at 70° C. for 1.5 hours, then cooled to ambient temperature. The mixture is diluted with EtOAc and washed with 1 N aqueous HCl, water, saturated aqueous NaHCO₃ and brine, dried with MgSO₄, filtered and concentrated under reduced pressure to provide compound 11b1.

Step 2:

Oxone™ (298 mg, 0.49 mmol) is added to a mixture of compound 11b1 (52 mg, 0.1 mmol) in acetone/water (3:1; 8 mL). The mixture is stirred at ambient temperature for 2 hours, then diluted with EtOAc and washed with water and brine. The organic phase is dried with MgSO₄, filtered and concentrated under reduced pressure. The residue is taken up in mixture of DMSO (2 mL), MeOH (1 mL) and water (0.2 mL). Aqueous LiOH (5 N, 0.20 mL, 1.0 mmol) is added and the mixture is stirred at ambient temperature overnight followed by 4 hours at 50° C. The mixture is allowed to cool to ambient temperature then is acidified with TFA, concentrated and purified by preparative HPLC to isolate compound 2071 (Table 2).

Example 12A

Preparation of Compound 2084, Table 2

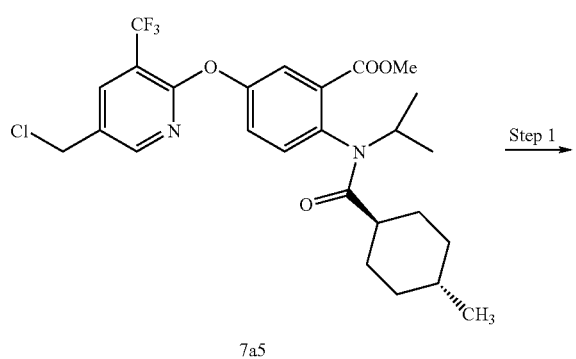

7a5

Step 1

-continued

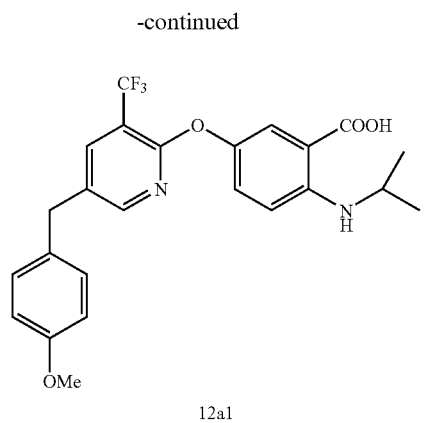

12a1

↓ Step 2

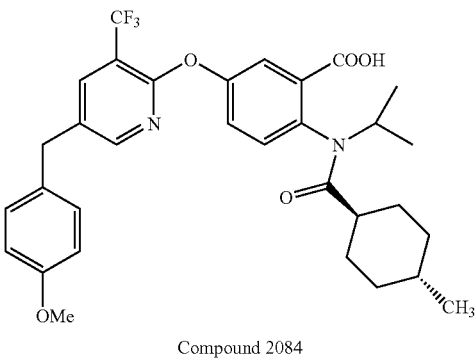

Compound 2084

Step 1:

A mixture of compound 7a5 (Example 7A) (30 mg, 0.06 mmol), FeCl₃ (9.7 mg, 0.06 mmol) and anisole (6.1 mg, 0.06 mmol) in CH₂Cl₂ (2 mL) is heated at 100° C. for 15 minutes in a microwave. The mixture is concentrated, then taken up in DMSO and purified by preparative HPLC to isolate intermediate 12a1.

Step 2:

A mixture of compound 12a1 (6 mg, 0.01 mmol), compound 1a7 (Example 1A) (13 mg, 0.08 mmol) and pyridine (0.3 mL) is heated to 180° C. for 12 minutes in a microwave. The mixture is purified by preparative HPLC to isolate compound 2084 (Table 2).

Example 13A

Preparation of Compound 2056, Table 2

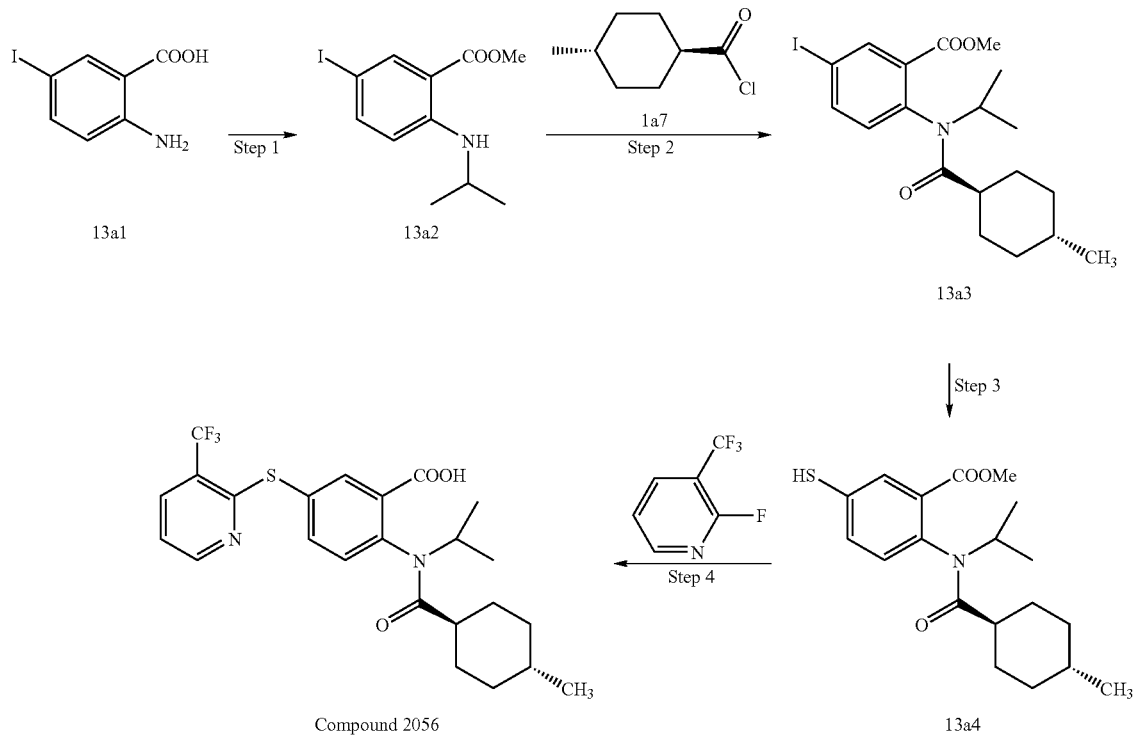

Step 1:

The procedure used is adapted from: Abdel-Magid, A. F.; Carson, K. G.; Harris, B. D.; Maryanoff, C. A.; Shah, R. D. *J. Org. Chem.* 1996, 61, 3849. To a mixture of compound 13a1 (10.0 g, 36 mmol) and $CH_2Cl_2$ (212 mL) is added 2-methoxypropene (13.8 mL, 144 mmol) followed by $NaBH(OAc)_3$ (15.3 g, 72 mmol) and AcOH (8.2 mL, 144 mmol). The mixture is stirred overnight at ambient temperature, then diluted with EtOAc and washed with $NaHCO_3$ and brine. The organic phase is dried with $MgSO_4$, filtered and concentrated under reduced pressure. The residue is subjected to flash chromatography (1:9 EtOAc/Hex) to isolate compound 13a2.

Step 2:

To a mixture of compound 13a2 (10.2 g, 32 mmol) in anhydrous pyridine (160 mL) is added compound 1a7 (Example 1A) (11.3 g, 70 mmol) and DMAP (~0.44 g). The mixture is stirred at 80° C. for 2 days, then is diluted with EtOAc (250 mL), and washed with 1N HCl, water, saturated aqueous $NaHCO_3$ and brine. The organic phase is dried with $MgSO_4$, filtered and concentrated under reduced pressure. The crude product is purified by flash chromatography (1:4 EtOAc/Hex) to afford amide 13a3.

Step 3:

The procedure used is adapted from: Takagi, K. *Chem. Lett.* (1985), 14: 1307. A mixture of compound 13a3 (100 mg, 0.23 mmol), $NiBr_2$ (5.7 mg, 0.03 mmol), thiourea (27 mg, 0.35 mmol) and $NaCNBH_3$ (2.2 mg, 0.04 mmol) in DMF (2 mL) is heated at 120° C. for 15 minutes in a microwave. Aqueous NaOH (2.5 N, 2.0 mL, 1.0 mmol) is added and the mixture is stirred for 15 minutes. The mixture is diluted with EtOAc and washed with aqueous 1 N HCl and brine. The organic phase is dried with $MgSO_4$, filtered and concentrated under reduced pressure to provide compound 13a4.

Step 4:

A mixture of compound 13a4 (40 mg, 0.11 mmol), 2-fluoro-3-trifluoromethylpyridine (21 mg, 0.13 mmol) and $K_2CO_3$ (55 mg, 0.40 mmol) in DMSO (1.0 mL) is stirred at 100° C. for 20 h. The mixture is cooled to room temperature and NaOH (2.5N, 300 μL, 0.75 mmol) is added. The mixture is stirred at 40° C. for 1 h, acidified with AcOH and purified by preparative HPLC to provide compound 2056 (Table 2).

Example 14A

Preparation of Compound 1004, Table 1

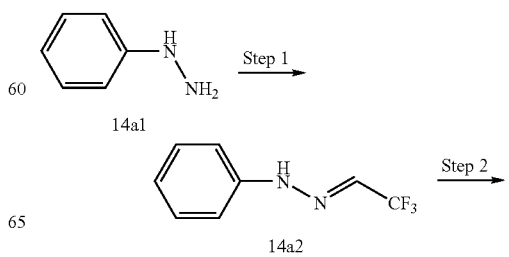

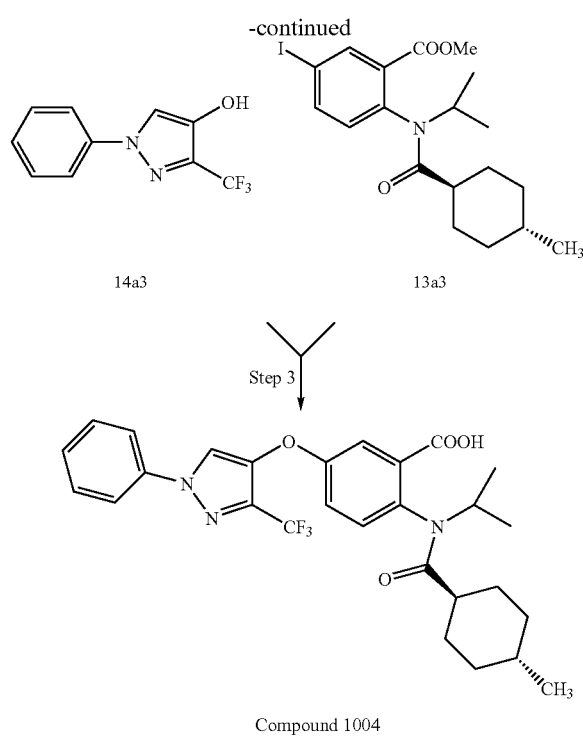

Reference: Tanaka, K.; Suzuki, T.; Maeno, S.; Mitsuhashi, K. *J. Heterocycl. Chem.* 1986, 23, 1537.

Step 1:

A mixture of compound 14a1 (500 mg, 4.62 mmol) and 1-ethoxy-2,2,2-trifluoroethanol (667 mg, 4.63 mmol) is heated at 80° C. for 2 h, then cooled and diluted with Et₂O. The mixture is washed with 1N HCl, water and brine, and the organic extract is dried (MgSO₄), filtered and concentrated to give compound 14a2.

Step 2:

A mixture of aqueous glyoxal (40%, 2.0 g, 13.8 mmol) and n-BuOAc (10 mL) is dried over MgSO₄ and filtered. To the filtrate is added compound 14a2 (853 mg, 4.5 mmol), AcOH (50 μL) and MgSO₄ (462 mg, 3.8 mmol), and the mixture is heated at 120° C. for 6 h. Further glyoxal is added (prepared by extracting aqueous glyoxal (40%, 27 g, 186 mmol) with EtOAc, drying the EtOAc extract over MgSO₄, adding n-BuOAc (10 mL) and concentrating the solution under reduced pressure) and heating at 120° C. is continued for a further 3.5 h. The mixture is filtered and concentrated, and the residue is mixed with 1N NaOH and washed with CH₂Cl₂. The aqueous phase is acidified to pH 2 with conc. HCl and extracted three times with CH₂Cl₂. The combined organic extracts are washed with water and brine, dried (MgSO₄), filtered and concentrated. The residue is purified by flash chromatography to provide compound 14a3.

Step 3:

A mixture of compound 13a3 (Example 13A) (39 mg, 0.088 mmol), compound 14a3 (20 mg, 0.088 mmol), Cs₂CO₃ (57 mg, 0.18 mmol), 2,2,6,6-tetramethylheptane-3,5-dione (2.0 μL, 0.01 mmol) and CuCl (4.4 mg, 0.044 mmol) in NMP (1.0 mL) under N₂ atmosphere is heated at 120° C. for 7 h on a J-Kem® orbital shaker (275 rpm). Aqueous NaOH (5N, 176 μL, 0.88 mmol) is added and the mixture is heated at 50° C. for 30 minutes. AcOH is added to a total volume of 1.5 mL and the mixture is filtered and purified by preparative HPLC to provide compound 1004 (Table 1).

Example 15A

Preparation of Compound 2196, Table 2

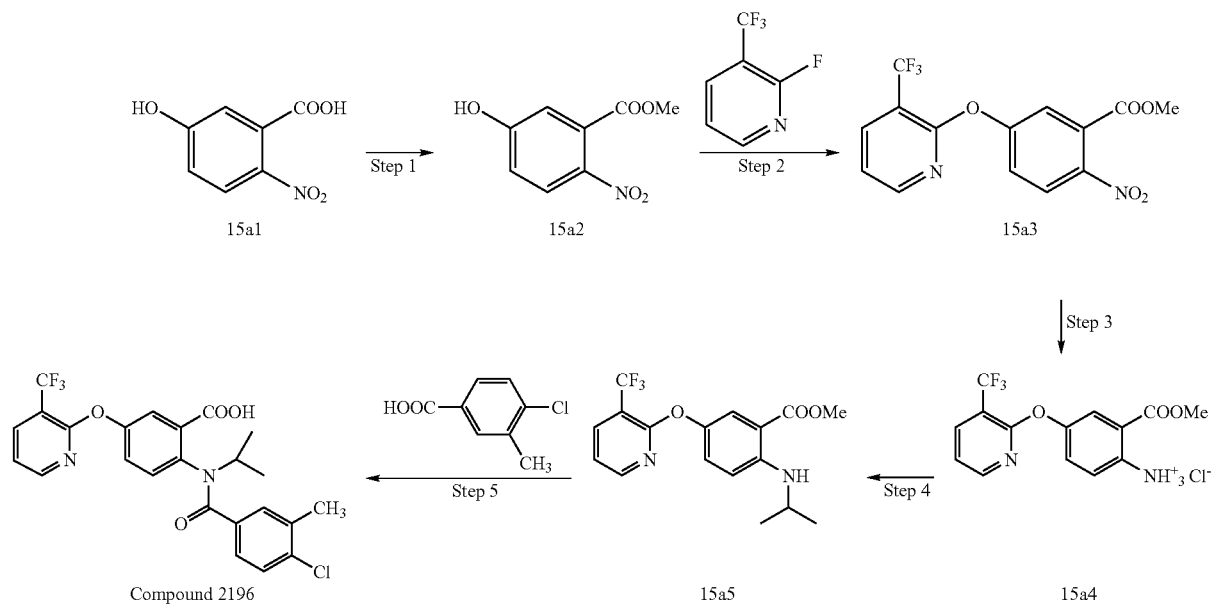

Step 1:

A mixture of carboxylic acid 15a1 (5.0 g, 27 mmol) and concentrated H₂SO₄ (4 mL) in MeOH (80 mL) is stirred at reflux for 12 hours. The mixture is concentrated under reduced pressure and poured onto a mixture of ice and saturated aqueous NaHCO₃. The aqueous mixture is acidified with citric acid and extracted twice with EtOAc. The combined organic extracts are washed with water and brine, dried with MgSO₄, filtered, and concentrated under reduced pressure. Purification by flash chromatography (3:7 EtOAc/Hexane) affords ester 15a2.

Step 2:

Compound 15a2 (10 g, 51 mmol), 2-fluoro-3-trifluoromethylpyridine (10 g, 61 mmol) and K₂CO₃ (8.4 g, 61 mmol) are mixed in anhydrous DMSO (150 mL) at room temperature under an argon atmosphere. The mixture is stirred at 100° C. overnight, cooled to room temperature and diluted with EtOAc (3 L). The organic phase is washed with saturated NH₄Cl solution and brine, dried over MgSO₄, filtered and concentrated under reduced pressure. Addition of Et₂O and hexanes to the residue provides compound 15a3; further compound 15a3 is obtained by concentrating the filtrate and purifying the residue by flash chromatography.

Step 3:

A mixture of compound 15a3 (12.5 g, 37 mmol), MeOH (600 mL) and Pd/C (1.4 g). is stirred at room temperature for 3.5 hours under H₂ (1 atm). The mixture is filtered through Celite™ and rinsed with MeOH. The filtrate is concentrated and the residue is purified by flash chromatography (gradient; 1/4 to 2/3 EtOAc/Hexanes). A mixture of the free aniline obtained and CH₂Cl₂ (250 mL) is cooled to 0° C. and 2M HCl in Et₂O (50 mL) is added. The mixture is stirred at room temperature for 1 h and the hydrochloride salt 15a4 is collected by filtration, rinsed with Et₂O and air dried.

Step 4:

To a mixture of compound 15a4 (2.1 g, 5.9 mmol) and 2-methoxypropene (2.3 mL, 24 mmol) in CH₂Cl₂ is added NaBH(OAc)₃ (2.5 g, 12 mmol) portionwise. The mixture is stirred at ambient temperature for 30 minutes, then diluted with EtOAc and washed with saturated aqueous NaHCO₃ and brine. The organic phase is dried with MgSO₄, filtered and concentrated under reduced pressure. Trituration of the residue in hexanes/ether followed by filtration, washing (hexanes) and drying affords compound 15a5.

Step 5:

Oxalyl chloride (2 M in DCM, 0.16 mL, 0.32 mmol) is added slowly to a mixture of 4-chloro-3-methylbenzoic acid (27 mg, 0.16 mmol) in DCM (1 mL). DMF (1 drop) is added and the mixture is stirred 30 minutes at ambient temperature and concentrated under reduced pressure. The residue is mixed with pyridine (0.5 mL), compound 15a5 (30 mg, 0.08 mmol) is added, and the mixture is stirred at 60° C. overnight. Aqueous NaOH (10 N, 0.096 mL, 0.96 mmol) and water (0.2 mL) are added and the mixture is stirred overnight at ambient temperature, then diluted with EtOAc and washed with 1N HCl and brine. The organic phase is dried with MgSO₄, filtered and concentrated under reduced pressure. Purification by preparative HPLC affords compound 2196 (Table 2).

Example 16A

Preparation of Compound 2124, Table 2

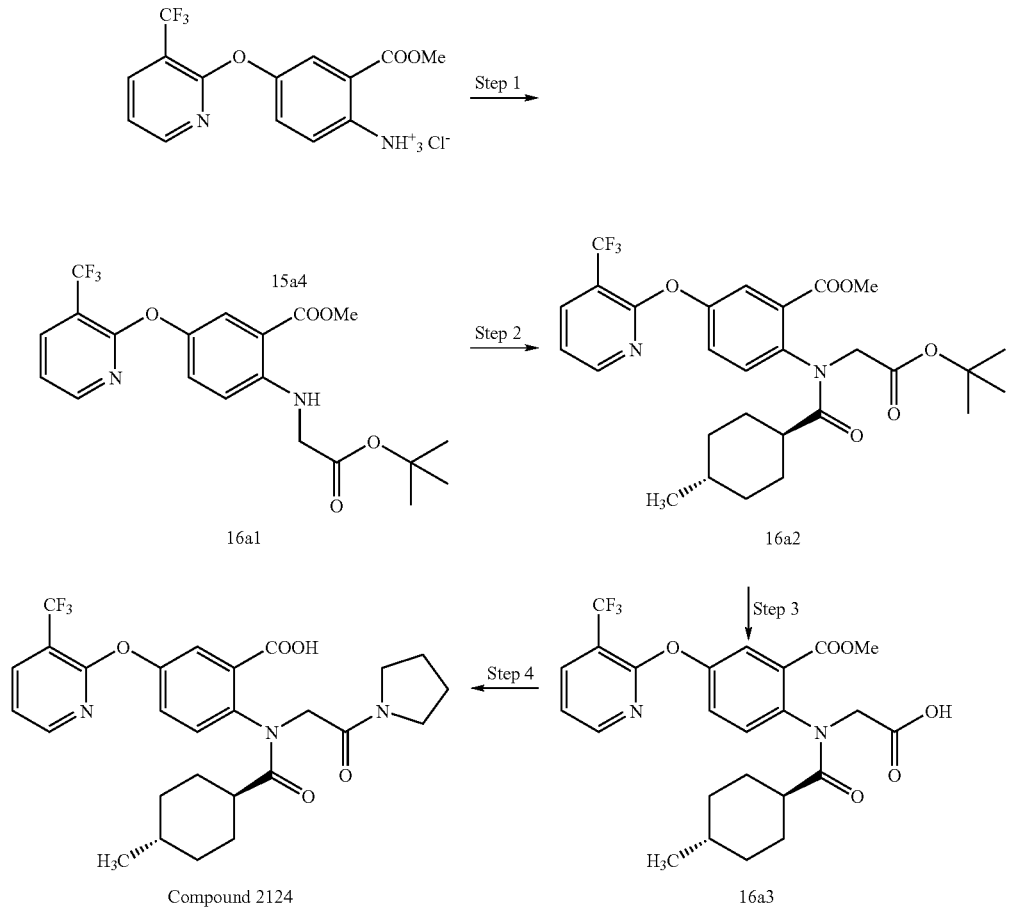

Step 1:

A mixture of compound 15a4 (Example 15A) (2.0 g, 5.8 mmol), tert-butylbromoacetate (4.3 mL, 29 mmol) and DIPEA (3.0 mL, 17 mmol) in DMF (20 mL) is stirred at 80° C. overnight. The mixture is diluted with EtOAc and washed with 0.5 N aqueous $KHSO_4$, saturated aqueous $NaHCO_3$ and brine. The organic phase is dried with $MgSO_4$, filtered and concentrated under reduced pressure. The residue is purified by flash chromatography (gradient; 1:9 to 1:1 EtOAc/Hex) to give compound 16a1.

Step 2:

To a mixture of 16a1 (1.6 g, 3.7 mmol) and DMAP (0.45 g, 3.7 mmol) in anhydrous pyridine (20 mL) is added compound 1a7 (Example 1A) (0.90 g, 5.6 mmol). The mixture is stirred at 70° C. overnight, then is diluted with EtOAc and washed with 1 N HCl, saturated aqueous $NaHCO_3$ and brine. The organic phase is dried with $MgSO_4$, filtered and concentrated under reduced pressure. Trituration with 1:9 EtOAc/Hex affords amide 16a2.

Step 3:

Trifluoroacetic acid (5 mL) is slowly added to a mixture of compound 16a2 (1.5 g, 2.8 mmol) and DCM (20 mL) at 0° C. The mixture is allowed to warm to ambient temperature and stir overnight, then is concentrated under reduced pressure. The residue is mixed with DCM and concentrated twice, then lyophilized from water and acetonitrile to afford acid 16a3.

Step 4:

To a mixture of compound 16a3 (25 mg, 0.05 mmol) and HATU (23 mg, 0.06 mmol) in DMF (0.5 mL) is added pyrrolidine (0.005 mL, 0.06 mmol), followed by $Et_3N$ (0.030 mL, 0.22 mmol). The mixture is agitated in a J-Kem® orbital shaker (250 rpm) for 1 hour at ambient temperature. Aqueous NaOH (5 N, 0.10 mL, 0.5 mmol) is added and agitation is continued overnight at ambient temperature. The mixture is acidified with AcOH (0.1 mL), diluted with DMSO (1 mL) and purified by preparative HPLC to isolate compound 2124 (Table 2).

Example 16B

Preparation of Compound 2149, Table 2

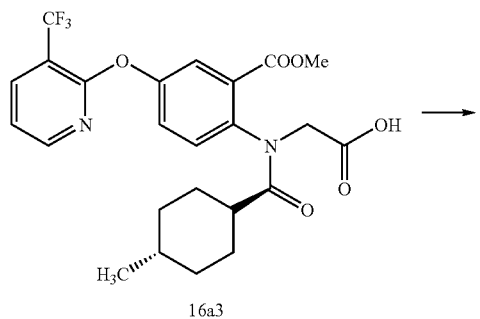

16a3

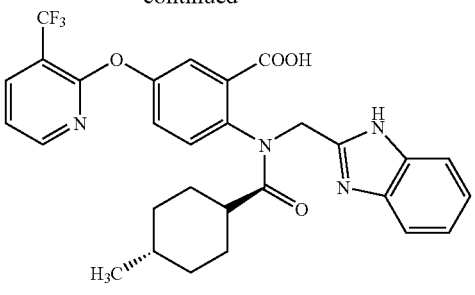

Compound 2149

To a mixture of acid 16a3 (Example 16A) (50 mg, 0.1 mmol) in DMF is added HATU (51 mg, 0.14 mmol), phenylenediamine (11 mg, 0.11 mmol) and $Et_3N$ (0.063 mL, 0.45 mmol). The mixture is stirred overnight at ambient temperature, then diluted with EtOAc and washed with 10% aqueous citric acid, water, saturated aqueous $NaHCO_3$ and brine. The organic phase is dried with $MgSO_4$, filtered and concentrated under reduced pressure. The residue is then mixed with AcOH (1 mL) and stirred at 100° C. for 1 hour. After cooling to ambient temperature, the mixture is diluted with EtOAc and washed with saturated aqueous $NaHCO_3$, water and brine. The organic phase is dried with $MgSO_4$, filtered and concentrated under reduced pressure. The residue (55 mg, 0.1 mmol) is combined with DMSO (2 mL), MeOH (1 mL) and water (0.15 mL). Aqueous NaOH (10 N, 0.097 mL, 0.10 mmol) is added and the mixture is stirred overnight at ambient temperature. The mixture is acidified with TFA and purified by preparative HPLC to isolate compound 2149 (Table 2).

Example 17

Inhibition of NS5B RNA Dependent RNA Polymerase Activity

Representative compounds of the invention are tested for inhibitory activity against the hepatitis C virus RNA dependent polymerase (NS5B), according to the protocol described below.

The HCV His-NS5BΔ21 polymerase [SEQ ID NO:1] lacks the C-terminal 21 amino acids and is expressed with an N-terminal hexa-histidine tag from a pET-based vector in *E. coli* strain JM109(DE3) and purified as described in McKercher et al., (2004) Nucleic Acids Res. 32: 422-431. The homogeneous enzyme preparation is stored at −20° C. in storage buffer (25 mM Tris/HCl pH 7.5, 300 mM NaCl, 5 mM DTT, 1 M EDTA and 30% (v/v) glycerol).

The purified His-NS5BΔ21 polymerase is reconstituted in an assay that measures the incorporation of $^3$H-UTP during the elongation of a biotin-oligo-$(U)_{12}$ RNA primer annealed to a homopolymeric poly(A) template. The test compound is added first, followed by the substrate, then the enzyme. At the end of the reaction, streptavidin scintillation proximity assay (SPA) beads are added and the radioactivity from the captured double-stranded RNA product is quantified on TopCount instrument (Packard). The components of the assay reaction are: 20 mM Tris-HCl pH 7.5, 1 mM TCEP, 1 mM EDTA, 5 mM $MgCl_2$, 0.01% w/v BSA, 5% v/v DMSO, 10 μg/mL Poly(A), 1 μg/mL Biotin-oligo-(U)$_{12}$, 333 nM UTP, 0.01 mCi/mL, (300 nM) $^3$H-UTP, 80 units/mL Rnasin, 12.5 nM His-NS5BΔ21 polymerase and test inhibitor compound that is serially diluted over a large concentration range. The assay is performed in 384-well plates with a 1.5 hour incubation at 22° C., and then stopped with a solution of 0.5 M EDTA and the products captured with Streptavidin-coated beads. Following the addition of 6 M CsCl to the bottom of each well, the plate is left at room temperature for 90 minutes before counting for 60 seconds on a TopCount. The calculated % inhibition values are then used to determine IC$_{50}$, slope factor (n) and maximum inhibition (I$_{max}$) by the non-linear regression routine NLIN procedure of SAS.

Example 18

Specificity of NS5B RNA Dependent RNA Polymerase Inhibition

Representative compounds of the invention are tested for inhibitory activity against polio virus RNA dependent RNA polymerase and calf thymus DNA dependent RNA polymerase II as described in McKercher et al., (2004) Nucleic Acids Res. 32: 422-431.

Example 19

Cell-Based Luciferase Reporter HCV RNA Replication Assay

Representative compounds of the invention are tested for activity as inhibitors of hepatitis C virus RNA replication in cells expressing a stable subgenomic HCV replicon, using the assay described in WO 2005/028501.

Tables of Compounds

The following tables list compounds representative of the invention. Representative compounds listed in Tables 1 and 2 below are tested in the NS5B polymerase activity inhibition assay of Example 33, and are found to have IC$_{50}$ values below 30 μM. Retention times (t$_R$) for each compound are measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

| Cpd | R$^2$ | R$^5$ | t$_R$ (min) | MS (M + H)$^+$ |
|---|---|---|---|---|
| 1001 | tetrahydropyran-4-yl | isopropyl | 5.8 | 404.2 |
| 1002 | tetrahydrofuran-3-yl | isopropyl | 5.2 | 390.2 |
| 1003 | 3-(trifluoromethyl)pyridin-4-yl | isopropyl | 6.1 | 465.1 |

TABLE 1-continued
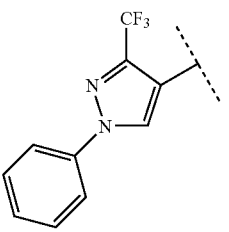
| Cpd | R² | R⁵ | t_R (min) | MS (M + H)⁺ |
|---|---|---|---|---|
| 1004 | 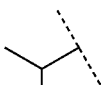 | 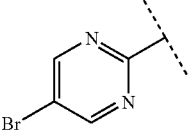 | 7.7 | 530 |
| 1005 | 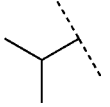 | 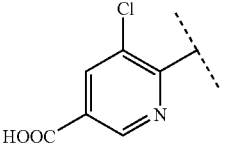 | 5.7 | 476.0 |
| 1006 | 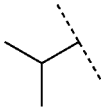 | 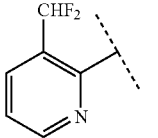 | 5.8 | 475.2 |
| 1007 | 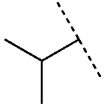 | 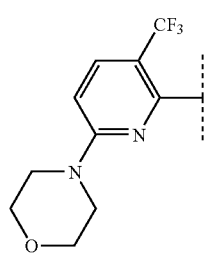 | 6.0 | 447.2 |
| 1008 | 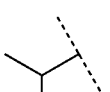 | 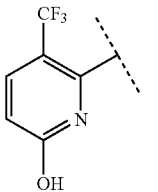 | 7.5 | 550 |
| 1009 | 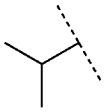 | | 6.6 | 481 |

TABLE 1-continued

[Structure: R²-O- substituted benzoic acid with COOH, N(R⁵)-C(=O)-cyclohexyl-CH₃ (trans)]

| Cpd | R² | R⁵ | $t_R$ (min) | MS $(M+H)^+$ |
|---|---|---|---|---|
| 1010 | 3-(pyridin-4-yl)-4-(trifluoromethyl)pyridin-2-yl | isobutyl | 5.6 | 542 |
| 1011 | pyridin-2-yl | isobutyl | 5.5 | 397.2 |
| 1012 | 3-cyanopyridin-2-yl | isobutyl | 5.5 | 422.2 |
| 1013 | 3-cyanopyrazin-2-yl | isobutyl | 5.5 | 423.2 |
| 1014 | 6-chloropyridin-2-yl | isobutyl | 6.2 | 431.2 |
| 1015 | 6-chloropyridazin-3-yl | isobutyl | 5.3 | 432.2 |
| 1016 | 6-chloropyrazin-2-yl | isobutyl | 5.8 | 432.2 |

TABLE 1-continued
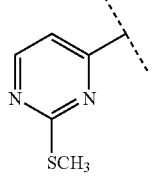
| Cpd | R² | R⁵ | t_R (min) | MS (M + H)⁺ |
|---|---|---|---|---|
| 1017 |  | 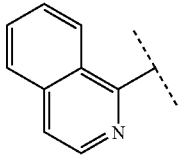 | 5.8 | 444.2 |
| 1018 |  | 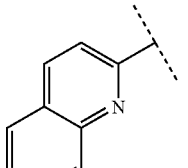 | 6.7 | 447.2 |
| 1019 |  | 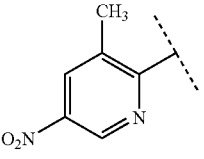 | 6.6 | 447.2 |
| 1020 |  | 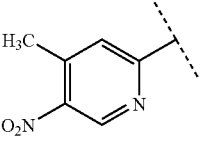 | 6.3 | 456.2 |
| 1021 |  | 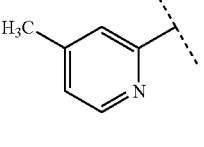 | 6.2 | 456.2 |
| 1022 |  | 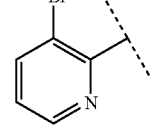 | 5.6 | 411.3 |
| 1023 |  | | 6.3 | 475.1 |

TABLE 1-continued

| Cpd | R² | R⁵ | t_R (min) | MS (M + H)⁺ |
|---|---|---|---|---|
| 1024 | 5-bromopyridin-2-yl | isobutyl | 6.4 | 475.1 |
| 1025 | 3-cyano-6-methylpyridin-2-yl | isobutyl | 5.8 | 436.2 |
| 1026 | 4-amino-6-chloropyridin-2-yl | isobutyl | 5.4 | 446.2 |
| 1027 | 4-carboxy-6-chloropyridin-2-yl | isobutyl | 5.6 | 475.1 |
| 1028 | 6-morpholinopyrazin-2-yl | isobutyl | 5.5 | 483.3 |
| 1029 | 2-(methoxymethyl)-6-(trifluoromethyl)-1H-benzimidazol-5-yl | isobutyl | 5.4 | 548 |

TABLE 1-continued

| Cpd | R² | R⁵ | t_R (min) | MS (M + H)⁺ |
|---|---|---|---|---|
| 1030 | 6-morpholinopyridin-2-yl | isobutyl | 6.3 | 482.2 |
| 1031 | thiophen-3-yl | isobutyl | 6.3 | 402.1 |
| 1032 | 3-chloropyridin-2-yl | isobutyl | 6.1 | 431.1 |
| 1033 | 2-phenyl-1H-benzimidazol-6-yl | isobutyl | 5.1 | 512.2 |
| 1034 | 2-(4-methoxyphenyl)-1H-benzimidazol-6-yl | isobutyl | 5.3 | 542.2 |
| 1035 | 6-CF₃-1-methyl-2-(methoxymethyl)-1H-benzimidazol-5-yl | isobutyl | 5.7 | 562.2 |
| 1036 | 5-CF₃-1-methyl-2-(methoxymethyl)-1H-benzimidazol-6-yl | isobutyl | 5.8 | 562 |

TABLE 2
| Cpd | R23 | X | R5 | R6 | tR (min) | MS (M + H)+ |
|---|---|---|---|---|---|---|
| 2001 | H | O | 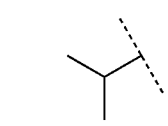 | 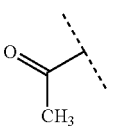 | 7.0 | 465.1 |
| 2002 | 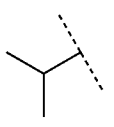 | O | 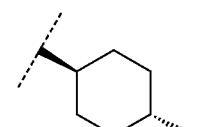 | 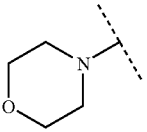 | 6.4 | 507.1 |
| 2003 | 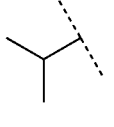 | O | 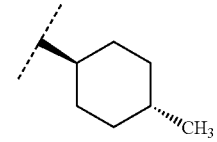 | 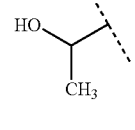 | 6.5 | 550.1 |
| 2004 | 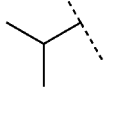 | O | 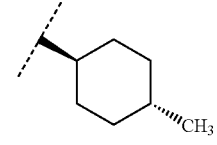 | 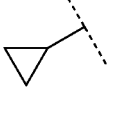 | 5.9 | 509.1 |
| 2005 | 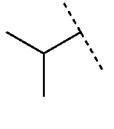 | O | 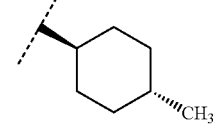 |  | 7.0 | 505.1 |
| 2006 | 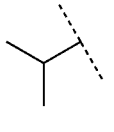 | O | 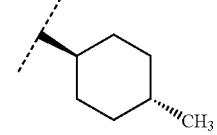 | 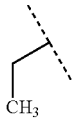 | 6.9 | 491.1 |
| 2007 | 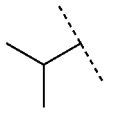 | O | 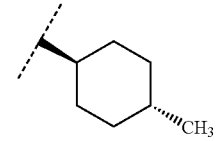 | 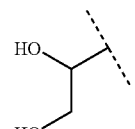 | 7.0 | 493.1 |
| 2008 | 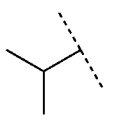 | O | 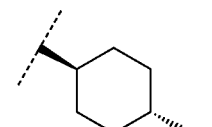 | | 5.4 | 525.1 |

TABLE 2-continued

| Cpd | R²³ | X | R⁵ | R⁶ | $t_R$ (min) | MS $(M + H)^+$ |
|---|---|---|---|---|---|---|
| 2009 | 3-(dimethylamino)pyrrolidin-1-yl | O | isopropyl | trans-4-methylcyclohexyl | 5.4 | 577.3 |
| 2010 | —CN | O | isopropyl | trans-4-methylcyclohexyl | 6.4 | 490.2 |
| 2011 | —I | O | isopropyl | trans-4-methylcyclohexyl | 7.1 | 591.1 |
| 2012 | 4-oxopyridin-1(4H)-yl-methyl | O | isopropyl | trans-4-methylcyclohexyl | 5.3 | 572.2 |
| 2013 | 1H-imidazol-1-ylmethyl | O | isopropyl | trans-4-methylcyclohexyl | 5.2 | 545.2 |
| 2014 | 1H-pyrazol-1-ylmethyl | O | isopropyl | trans-4-methylcyclohexyl | 6.2 | 545.2 |
| 2015 | (2-hydroxypyridin-4-yloxy)methyl | O | isopropyl | trans-4-methylcyclohexyl | 6.0 | 588.2 |

TABLE 2-continued

| Cpd | R²³ | X | R⁵ | R⁶ | t_R (min) | MS (M + H)⁺ |
|---|---|---|---|---|---|---|
| 2016 | 5-(methyl)pyridin-2-yloxyethyl | O | isobutyl | trans-4-methylcyclohexyl | 5.5 | 586.3 |
| 2017 | 3-(pyridin-N-oxide)oxyethyl | O | isobutyl | trans-4-methylcyclohexyl | 6.0 | 588.2 |
| 2018 | 6-hydroxypyrimidin-4-yloxyethyl | O | isobutyl | trans-4-methylcyclohexyl | 5.8 | 589.2 |
| 2019 | 2-cyanopyridin-3-yloxyethyl | O | isobutyl | trans-4-methylcyclohexyl | 6.6 | 597.2 |
| 2020 | 2,6-dimethylpyridin-3-yloxyethyl | O | isobutyl | trans-4-methylcyclohexyl | 5.6 | 600.3 |
| 2021 | 5-chloropyridin-3-yloxyethyl | O | isobutyl | trans-4-methylcyclohexyl | 7.0 | 606.2 |

TABLE 2-continued

| Cpd | R²³ | X | R⁵ | R⁶ | t_R (min) | MS (M + H)⁺ |
|---|---|---|---|---|---|---|
| 2022 | —CH₂OH | O | isobutyl | trans-4-methylcyclohexyl | 5.7 | 495.2 |
| 2023 | 1,3,5-triazin-2-ylamino-ethyl | O | isobutyl | trans-4-methylcyclohexyl | 5.6 | 573.2 |
| 2024 | (4-methylpyrazol-1-yl)methyl | O | isobutyl | trans-4-methylcyclohexyl | 7.1 | 559.2 |
| 2025 | (3,5-dimethylpyrazol-1-yl)methyl | O | isobutyl | trans-4-methylcyclohexyl | 6.9 | 573.2 |
| 2026 | (indol-1-yl)methyl | O | isobutyl | trans-4-methylcyclohexyl | 7.9 | 594.2 |
| 2027 | (7-azaindol-1-yl)methyl | O | isobutyl | trans-4-methylcyclohexyl | 7.2 | 595.2 |

TABLE 2-continued

| Cpd | R²³ | X | R⁵ | R⁶ | t_R (min) | MS (M + H)⁺ |
|---|---|---|---|---|---|---|
| 2028 | 1-indazolylmethyl | O | isobutyl | trans-4-methylcyclohexyl | 7.5 | 595.2 |
| 2029 | (2-oxooxazolidin-3-yl)methyl | O | isobutyl | trans-4-methylcyclohexyl | 6.4 | 564.2 |
| 2030 | -CH₂NHC(O)CH₂CH₂COOH | O | isobutyl | trans-4-methylcyclohexyl | 5.7 | 594.2 |
| 2031 | phenoxyethyl | O | isobutyl | trans-4-methylcyclohexyl | 7.9 | 571.2 |
| 2032 | (2-oxopyridin-1-yl)methyl | O | isobutyl | trans-4-methylcyclohexyl | 6.2 | 572.2 |
| 2033 | (pyridin-3-yloxy)ethyl | O | isobutyl | trans-4-methylcyclohexyl | 5.3 | 572.2 |
| 2034 | (2-methoxyphenoxy)ethyl | O | isobutyl | trans-4-methylcyclohexyl | 7.7 | 601.2 |

TABLE 2-continued
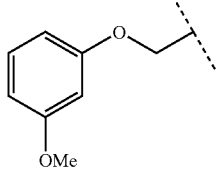
| Cpd | R23 | X | R5 | R6 | t_R (min) | MS (M + H)+ |
|---|---|---|---|---|---|---|
| 2035 | 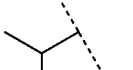 | O | 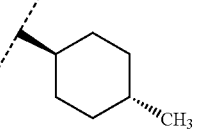 | 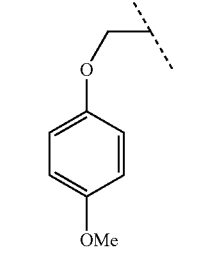 | 7.8 | 601.2 |
| 2036 | 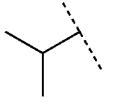 | O | 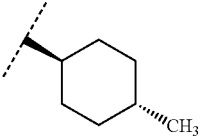 | 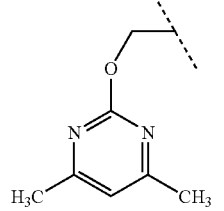 | 7.8 | 601.2 |
| 2037 | 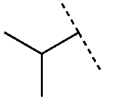 | O | 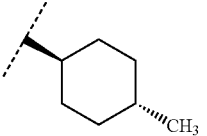 | 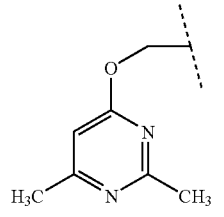 | 7.2 | 601.3 |
| 2038 | 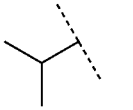 | O | 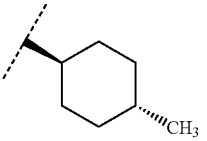 | 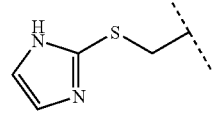 | 5.6 | 601.3 |
| 2039 | 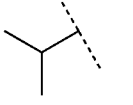 | O | 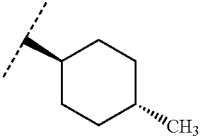 | 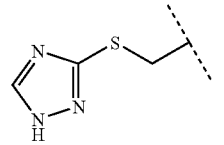 | 4.9 | 577.2 |
| 2040 | 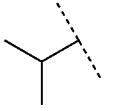 | O | 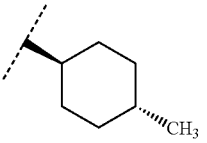 |  | 6.2 | 578.2 |

TABLE 2-continued

| Cpd | R²³ | X | R⁵ | R⁶ | t_R (min) | MS (M + H)⁺ |
|---|---|---|---|---|---|---|
| 2041 | 3-amino-1H-1,2,4-triazol-5-yl-S-CH₂- | O | isopropyl | trans-4-methylcyclohexyl | 5.4 | 593.2 |
| 2042 | 4-methyl-4H-1,2,4-triazol-3-yl-S-CH₂- | O | isopropyl | trans-4-methylcyclohexyl | 5.9 | 592.2 |
| 2043 | 2-methylfuran-3-yl-S-CH₂- | O | isopropyl | trans-4-methylcyclohexyl | 7.8 | 591.2 |
| 2044 | thiazol-2-yl-S-CH₂- | O | isopropyl | trans-4-methylcyclohexyl | 7.5 | 594.2 |
| 2045 | pyrrolidin-1-yl-CH₂- | O | isopropyl | trans-4-methylcyclohexyl | 4.9 | 548.3 |
| 2046 | (CH₃)₂N-CH₂- | O | isopropyl | trans-4-methylcyclohexyl | 4.8 | 522.2 |
| 2047 | 3-hydroxypyrrolidin-1-yl-CH₂- | O | isopropyl | trans-4-methylcyclohexyl | 4.8 | |

TABLE 2-continued
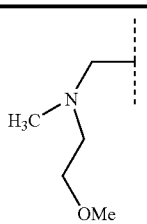
| Cpd | R[23] | X | R[5] | R[6] | $t_R$ (min) | MS (M + H)[+] |
|---|---|---|---|---|---|---|
| 2048 | 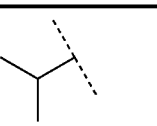 | O | 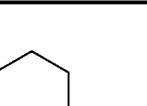 | 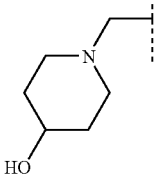 | 4.9 | 566.3 |
| 2049 | 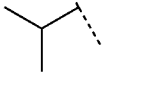 | O | 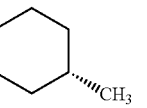 | 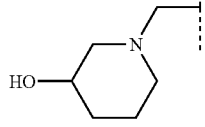 | 4.7 | 578.3 |
| 2050 | 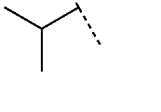 | O | 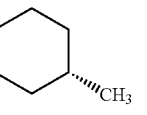 | 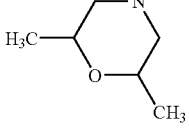 | 4.8 | 578.3 |
| 2051 |  | O | 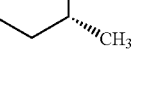 | 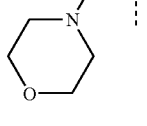 | 5.1 | 592.3 |
| 2052 |  | O | 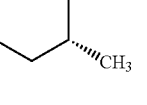 | 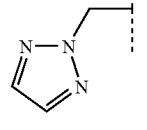 | 4.8 | 564.3 |
| 2053 | 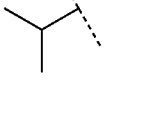 | O | 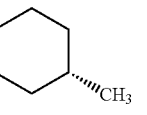 | 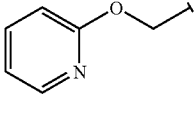 | 7.0 | 546.2 |
| 2054 | 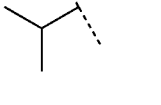 | O | 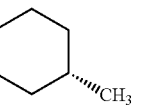 |  | 7.5 | 572.2 |

TABLE 2-continued

[Structure: pyridine with CF₃ group and R²³ substituent, connected via X to a benzene ring bearing COOH and N(R⁵)C(O)R⁶ groups]

| Cpd | R²³ | X | R⁵ | R⁶ | t_R (min) | MS (M + H)⁺ |
|---|---|---|---|---|---|---|
| 2055 | H | O | CH₃ | trans-4-methylcyclohexyl | 6.0 | 437.2 |
| 2056 | H | S | isobutyl | trans-4-methylcyclohexyl | 6.7 | 481.2 |
| 2057 | 3-oxopyrrolidin-1-ylmethyl | O | isobutyl | trans-4-methylcyclohexyl | 5.0 | 562.2 |
| 2058 | 4-oxopiperidin-1-ylmethyl | O | isobutyl | trans-4-methylcyclohexyl | 4.9 | 576.2 |
| 2059 | H | O | isobutyl | 3,4-dimethylphenyl | 6.0 | 473.1 |
| 2060 | (5-methylisoxazol-3-yl)aminomethyl | O | isobutyl | trans-4-methylcyclohexyl | 6.9 | 575.2 |
| 2061 | (5-amino-1H-tetrazol-1-yl)methyl | O | isobutyl | trans-4-methylcyclohexyl | 5.9 | 562.2 |

TABLE 2-continued

| Cpd | R23 | X | R5 | R6 | $t_R$ (min) | MS $(M+H)^+$ |
|---|---|---|---|---|---|---|
| 2062 | 2-amino-tetrazol-2-yl-methyl | O | isobutyl | trans-4-methylcyclohexyl | 6.2 | 562.2 |
| 2063 | (1H-benzimidazol-2-ylamino)methyl | O | isobutyl | trans-4-methylcyclohexyl | 5.5 | 610.2 |
| 2064 | (pyrimidin-2-ylthio)methyl | O | isobutyl | trans-4-methylcyclohexyl | 7.3 | 589.2 |
| 2065 | (pyridin-2-ylthio)methyl | O | isobutyl | trans-4-methylcyclohexyl | 7.6 | 588.2 |
| 2066 | (pyridin-3-ylamino)methyl | O | isobutyl | trans-4-methylcyclohexyl | 5.1 | 571.2 |
| 2067 | (5-chloropyrimidin-2-ylamino)methyl | O | isobutyl | trans-4-methylcyclohexyl | 7.5 | 606.2 |

TABLE 2-continued

| Cpd | R²³ | X | R⁵ | R⁶ | $t_R$ (min) | MS $(M + H)^+$ |
|---|---|---|---|---|---|---|
| 2068 | (1-methyl-tetrazol-5-yl)-S-CH₂– | O | isobutyl | trans-4-methylcyclohexyl | 6.9 | 593.2 |
| 2069 | CH₃-SO₂– | O | isobutyl | trans-4-methylcyclohexyl | 6.1 | 543.1 |
| 2070 | (CH₃)₂CH-SO₂– | O | isobutyl | trans-4-methylcyclohexyl | 6.4 | 571.1 |
| 2071 | CH₃-SO₂-CH₂– | O | isobutyl | trans-4-methylcyclohexyl | 5.8 | 557.1 |
| 2072 | (3,3-difluoropyrrolidin-1-yl)-CH₂– | O | isobutyl | trans-4-methylcyclohexyl | 5.2 | 584.1 |
| 2073 | (4-methylthiazol-2-yl)-NH-CH₂– | O | isobutyl | trans-4-methylcyclohexyl | 5.4 | 591.2 |
| 2074 | H | O | isobutyl | 4-cyclopropylphenyl | 6.0 | 485.1 |

TABLE 2-continued

| Cpd | R23 | X | R5 | R6 | t_R (min) | MS (M + H)+ |
|---|---|---|---|---|---|---|
| 2075 | 2-pyridyl N-oxide-SO2-CH2- | O | isobutyl | trans-4-methylcyclohexyl | 5.8 | 636.1 |
| 2076 | thiazol-2-yl-S-CH2- | O | CH3 | trans-4-methylcyclohexyl | 6.5 | 566.0 |
| 2077 | 2-oxo-pyridin-1-yl-CH2- | O | CH3 | trans-4-methylcyclohexyl | 5.6 | 544.1 |
| 2078 | pyridin-2-yloxy-CH2- | O | CH3 | trans-4-methylcyclohexyl | 6.4 | 544.1 |
| 2079 | morpholin-4-yl-CH2- | O | CH3 | trans-4-methylcyclohexyl | 4.8 | 536.1 |
| 2080 | 1H-1,2,3-triazol-1-yl-CH2- | O | CH3 | trans-4-methylcyclohexyl | 5.5 | 518.1 |
| 2081 | 2H-1,2,3-triazol-2-yl-CH2- | O | CH3 | trans-4-methylcyclohexyl | 5.9 | 518.1 |

TABLE 2-continued

| Cpd | R²³ | X | R⁵ | R⁶ | t_R (min) | MS (M + H)⁺ |
|---|---|---|---|---|---|---|
| 2082 | H | O | -CH₂CH₂CH₂COOH | trans-4-methylcyclohexyl | 5.6 | 495.1 |
| 2083 | 2-(1-oxidopyridinyl)thiomethyl | O | isobutyl | trans-4-methylcyclohexyl | 5.9 | 604.1 |
| 2084 | 4-methoxybenzyl | O | isobutyl | trans-4-methylcyclohexyl | 7.3 | 585.2 |
| 2085 | H | O | -CH₂CH₂C(O)N(CH₃)₂ | trans-4-methylcyclohexyl | 5.8 | 522.1 |
| 2086 | H | O | isobutyl | 2,4-dichlorophenyl | 7.0 | 512.9 |
| 2087 | H | O | isobutyl | 2,4-dimethylphenyl | 6.7 | 473.1 |
| 2088 | H | O | isobutyl | 3-bromo-4-methylphenyl | 6.9 | 537 |

TABLE 2-continued
| Cpd | R²³ | X | R⁵ | R⁶ | $t_R$ (min) | MS $(M + H)^+$ |
|---|---|---|---|---|---|---|
| 2089 | H | O | isobutyl | 4-Br-C₆H₄ | 6.7 | 522.9 |
| 2090 | H | O | isobutyl | 4-Cl-C₆H₄ | 6.6 | 479 |
| 2091 | H | O | isobutyl | 4-SCH₃-C₆H₄ | 6.5 | 491 |
| 2092 | H | O | isobutyl | 4-CH₂CH₃-C₆H₄ | 6.8 | 473.1 |
| 2093 | H | O | isobutyl | 3-CH₃-4-Br-C₆H₃ | 7.0 | 537 |
| 2094 | H | O | isobutyl | 2-CH₃-4-Br-C₆H₃ | 6.9 | 537 |
| 2095 | H | O | isobutyl | 2-F-4-Cl-C₆H₃ | 6.8 | 497 |
| 2096 | H | O | isobutyl | 3-Cl-4-CH₃-C₆H₃ | 6.9 | 493 |

TABLE 2-continued
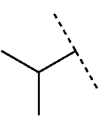
| Cpd | R23 | X | R5 | R6 | tR (min) | MS (M + H)+ |
|---|---|---|---|---|---|---|
| 2097 | H | O | 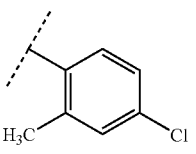 | 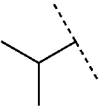 | 6.8 | 493 |
| 2098 | H | O | 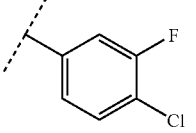 | 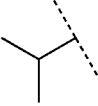 | 6.8 | 497 |
| 2099 | H | O | 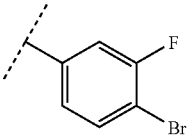 | 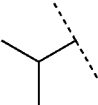 | 6.8 | 540.9 |
| 2100 | H | O | 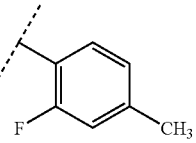 | 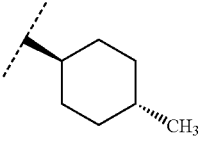 | 6.6 | 477.1 |
| 2101 | 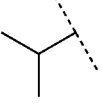 | O | CH3 | 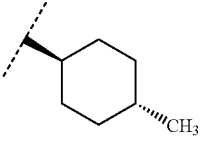 | 5.6 | 576.1 |
| 2102 | 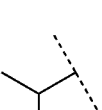 | O | 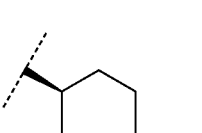 | 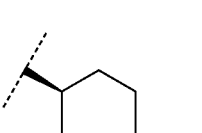 | 5.2 | 577.1 |
| 2103 | 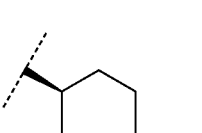 | O | | | 6.2 | 576.1 |

TABLE 2-continued

| Cpd | R23 | X | R5 | R6 | tR (min) | MS (M + H)+ |
|---|---|---|---|---|---|---|
| 2104 | 2-(methylamino)thiazol-4-ylmethyl | O | isopropyl | trans-4-methylcyclohexyl | 5.4 | 591.1 |
| 2105 | 2-(dimethylamino)thiazol-4-ylmethyl | O | isopropyl | trans-4-methylcyclohexyl | 5.5 | 605.1 |
| 2106 | 2-acetamidothiazol-4-ylmethyl | O | isopropyl | trans-4-methylcyclohexyl | 6.2 | 619.1 |
| 2107 | benzimidazol-1-ylmethyl | O | isopropyl | trans-4-methylcyclohexyl | 5.5 | 595.1 |
| 2108 | imidazo[4,5-b]pyridin-3-ylmethyl | O | isopropyl | trans-4-methylcyclohexyl | 5.6 | 596.1 |

TABLE 2-continued
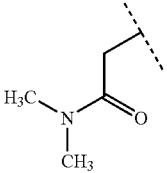
| Cpd | R23 | X | R5 | R6 | tR (min) | MS (M + H)+ |
|---|---|---|---|---|---|---|
| 2109 | H | O | 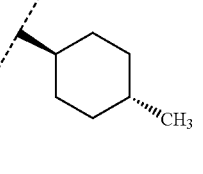 | 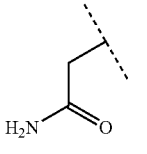 | 5.6 | 508.1 |
| 2110 | H | O | 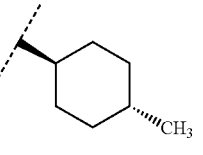 | 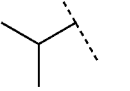 | 5.4 | 480.1 |
| 2111 |  | O | 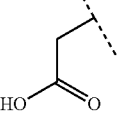 | 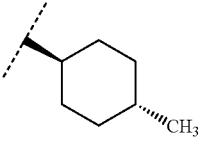 | 5.9 | 594.2 |
| 2112 | H | O | 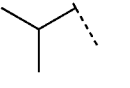 | 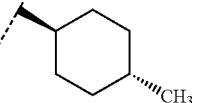 | 5.5 | 481.1 |
| 2113 | 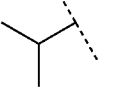 | O | | | 6.9 | 611.2 |
| 2114 |  | O | | | 5.1 | 580.2 |
| 2115 | 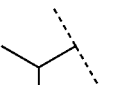 | O | | 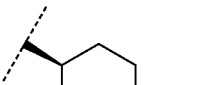 | 6.2 | 612.2 |

TABLE 2-continued

| Cpd | R23 | X | R5 | R6 | $t_R$ (min) | MS $(M + H)^+$ |
|---|---|---|---|---|---|---|
| 2116 | 6-methylpyridin-3-yloxyethyl | O | isobutyl | trans-4-methylcyclohexyl | 5.3 | 598.2 |
| 2117 | pyridin-3-yloxyethyl N-oxide | O | isobutyl | trans-4-methylcyclohexyl | 7.0 | 598.3 |
| 2118 | 6-hydroxypyrimidin-4-yloxyethyl | O | isobutyl | trans-4-methylcyclohexyl | 5.7 | 546.2 |
| 2119 | 2-cyanopyridin-3-yloxyethyl | O | isobutyl | trans-4-methylcyclohexyl | 5.2 | 577.2 |
| 2120 | 2,6-dimethylpyridin-3-yloxyethyl | O | isobutyl | trans-4-methylcyclohexyl | 5.8 | 572.3 |
| 2121 | 5-chloropyridin-3-yloxyethyl | O | isobutyl | trans-4-methylcyclohexyl | 5.3 | 574.3 |

TABLE 2-continued
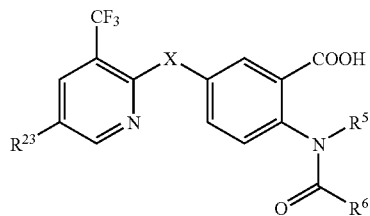
| Cpd | R²³ | X | R⁵ | R⁶ | $t_R$ (min) | MS $(M+H)^+$ |
|---|---|---|---|---|---|---|
| 2122 | H | O | -CH₂C(O)NHCH₃ | trans-4-methylcyclohexyl | 6.0 | 494.2 |
| 2123 | H | O | -CH₂C(O)N(CH₃)(Et) | trans-4-methylcyclohexyl | 6.6 | 522.2 |
| 2124 | H | O | -CH₂C(O)-pyrrolidinyl | trans-4-methylcyclohexyl | 6.6 | 534.2 |
| 2125 | H | O | -CH₂C(O)N(Et)₂ | trans-4-methylcyclohexyl | 6.9 | 536.2 |
| 2126 | H | O | -CH₂C(O)N(CH₃)(iPr) | trans-4-methylcyclohexyl | 6.9 | 536.2 |
| 2127 | H | O | -CH₂C(O)-piperidinyl | trans-4-methylcyclohexyl | 7.0 | 548.2 |

TABLE 2-continued

| Cpd | R23 | X | R5 | R6 | tR (min) | MS (M + H)+ |
|---|---|---|---|---|---|---|
| 2128 | H | O | cyclopentyl-NH-C(O)-CH2- | trans-4-methylcyclohexyl | 7.0 | 548.2 |
| 2129 | H | O | morpholino-C(O)-CH2- | trans-4-methylcyclohexyl | 6.2 | 550.2 |
| 2130 | H | O | 3-hydroxypyrrolidin-1-yl-C(O)-CH2- | trans-4-methylcyclohexyl | 5.7 | 550.3 |
| 2131 | H | O | N-methyl-N-isobutyl-NC(O)-CH2- | trans-4-methylcyclohexyl | 7.2 | 550.3 |
| 2132 | H | O | N-ethyl-N-isopropyl-NC(O)-CH2- | trans-4-methylcyclohexyl | 7.1 | 550.3 |

TABLE 2-continued
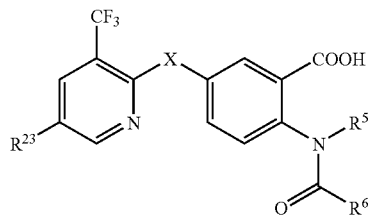
| Cpd | R²³ | X | R⁵ | R⁶ | $t_R$ (min) | MS (M + H)⁺ |
|---|---|---|---|---|---|---|
| 2133 | H | O | | | 5.0 | 551.3 |
| 2134 | H | O | | | 6.5 | 552.2 |
| 2135 | H | O | | | 5.6 | 563.2 |
| 2136 | H | O | | | 5.2 | 571.2 |
| 2137 | H | O | | | 6.0 | 578.3 |

TABLE 2-continued

| Cpd | R²³ | X | R⁵ | R⁶ | t_R (min) | MS (M + H)⁺ |
|---|---|---|---|---|---|---|
| 2138 | H | O | CH₂C(O)NH-CH₂-(tetrahydropyran-4-yl) | trans-4-methylcyclohexyl | 6.2 | 578.3 |
| 2139 | H | O | CH₂CH₂C(O)-(2,6-dimethylmorpholin-4-yl) | trans-4-methylcyclohexyl | 6.8 | 578.3 |
| 2140 | H | O | CH₂C(O)N(iPr)(CH₂CH₂OMe) | trans-4-methylcyclohexyl | 7.0 | 580.3 |
| 2141 | H | O | CH₂C(O)-(4-acetylpiperazin-1-yl) | trans-4-methylcyclohexyl | 5.9 | 591.3 |

TABLE 2-continued

| Cpd | R²³ | X | R⁵ | R⁶ | t_R (min) | MS (M + H)⁺ |
|---|---|---|---|---|---|---|
| 2142 | H | O | 3-acetamidopyrrolidin-1-yl-propanoyl | trans-4-methylcyclohexyl | 5.7 | 591.3 |
| 2143 | H | O | 4-(dimethylamino)piperidin-1-yl-propanoyl | trans-4-methylcyclohexyl | 5.0 | 591.3 |
| 2144 | H | O | thiomorpholine-1,1-dioxide-propanoyl | trans-4-methylcyclohexyl | 6.3 | 598.2 |
| 2145 | H | O | 2-(trifluoromethyl)pyrrolidin-1-yl-propanoyl | trans-4-methylcyclohexyl | 7.2 | 602.2 |
| 2146 | H | O | 3,3-difluoropyrrolidin-1-yl-propanoyl | trans-4-methylcyclohexyl | 6.8 | 570.2 |

TABLE 2-continued

| Cpd | R²³ | X | R⁵ | R⁶ | t_R (min) | MS (M + H)⁺ |
|---|---|---|---|---|---|---|
| 2147 | H | O | 3,3-difluoropiperidinyl-CH₂-C(O)- | trans-4-methylcyclohexyl | 7.0 | 584.2 |
| 2148 | H | O | 4,4-difluoropiperidinyl-CH₂-C(O)- | trans-4-methylcyclohexyl | 7.0 | 584.2 |
| 2149 | H | O | (1H-benzimidazol-2-yl)methyl | trans-4-methylcyclohexyl | 5.5 | 553.3 |
| 2150 | H | O | (1H-imidazo[4,5-c]pyridin-2-yl)methyl | trans-4-methylcyclohexyl | 5.2 | 554.3 |
| 2151 | pyrimidin-4-yl-NH-CH₂- | O | isopropyl | trans-4-methylcyclohexyl | 5.2 | 572.3 |

TABLE 2-continued
| Cpd | R²³ | X | R⁵ | R⁶ | $t_R$ (min) | MS (M + H)⁺ |
|---|---|---|---|---|---|---|
| 2152 | 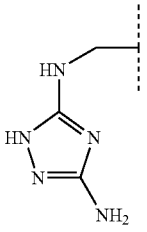 | O | 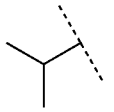 | 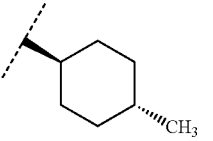 | 5.0 | 576.3 |
| 2153 | 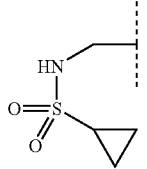 | O | 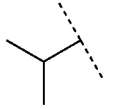 | 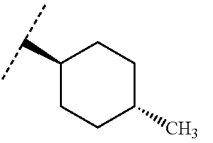 | 6.7 | 598.3 |
| 2154 | 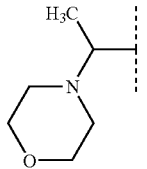 | O | 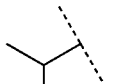 | 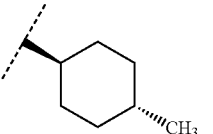 | 5.0 | 578.3 |
| 2155 | 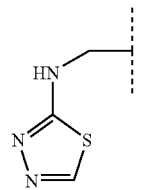 | O | 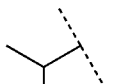 | 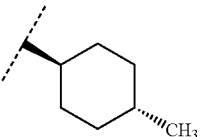 | 5.5 | 578.2 |
| 2156 | 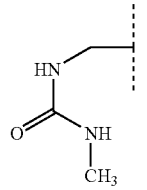 | O | 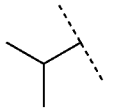 | 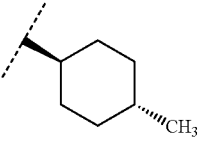 | 5.8 | 551.3 |
| 2157 | 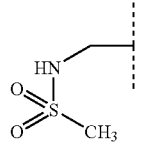 | O | 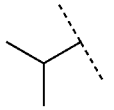 | 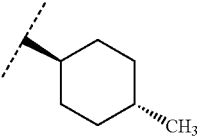 | 6.3 | 572.2 |

TABLE 2-continued

Structure:
- Central scaffold: pyridine with CF$_3$ at 3-position, R$^{23}$ at 5-position, connected via X at 2-position to a phenyl ring bearing COOH and N(R$^5$)C(O)R$^6$

| Cpd | R$^{23}$ | X | R$^5$ | R$^6$ | t$_R$ (min) | MS (M+H)$^+$ |
|---|---|---|---|---|---|---|
| 2158 | tert-butyl-NH-C(O)-NH-CH$_2$- | O | isobutyl | trans-4-methylcyclohexyl | 6.9 | 593.3 |
| 2159 | isopropyl-NH-C(O)-NH-CH$_2$- | O | isobutyl | trans-4-methylcyclohexyl | 6.4 | 579.3 |
| 2160 | isobutyl-O-C(O)-NH-CH$_2$- | O | isobutyl | trans-4-methylcyclohexyl | 7.4 | 594.3 |
| 2161 | ethyl-O-C(O)-NH-CH$_2$- | O | isobutyl | trans-4-methylcyclohexyl | 6.9 | 588.3 |
| 2162 | isopropyl-O-C(O)-NH-CH$_2$- | O | isobutyl | trans-4-methylcyclohexyl | 7.1 | 580.3 |
| 2163 | methyl-O-C(O)-NH-CH$_2$- | O | isobutyl | trans-4-methylcyclohexyl | 6.6 | 552.3 |

TABLE 2-continued

| Cpd | R²³ | X | R⁵ | R⁶ | t_R (min) | MS (M + H)⁺ |
|---|---|---|---|---|---|---|
| 2164 | benzimidazol-2-ylmethyl | O | isobutyl | trans-4-methylcyclohexyl | 5.4 | 595.3 |
| 2165 | 5-fluorobenzimidazol-2-ylmethyl | O | isobutyl | trans-4-methylcyclohexyl | 5.4 | 613.3 |
| 2166 | (3,3-dimethylureido)methyl | O | isobutyl | trans-4-methylcyclohexyl | 6.1 | 565.3 |
| 2167 | (pyrrolidine-1-carboxamido)methyl | O | isobutyl | trans-4-methylcyclohexyl | 6.4 | 591.3 |
| 2168 | (3-isopropyl-3-methylureido)methyl | O | isobutyl | trans-4-methylcyclohexyl | 6.7 | 593.3 |
| 2169 | (1-ethyl-1H-pyrazol-5-ylamino)methyl | O | isobutyl | trans-4-methylcyclohexyl | 6.0 | 588.3 |

TABLE 2-continued

| Cpd | R²³ | X | R⁵ | R⁶ | t_R (min) | MS (M + H)⁺ |
|---|---|---|---|---|---|---|
| 2170 | 2-chloropyridin-4-yl-NH-CH₂– | O | isobutyl | trans-4-methylcyclohexyl | 5.9 | 605.3 |
| 2171 | 2H-tetrazol-2-yl-CH₂– | O | isobutyl | trans-4-methylcyclohexyl | 6.0 | 547.2 |
| 2172 | 1H-tetrazol-1-yl-CH₂– | O | isobutyl | trans-4-methylcyclohexyl | 5.7 | 547.2 |
| 2173 | 1H-benzotriazol-1-yl-CH₂– | O | isobutyl | trans-4-methylcyclohexyl | 6.4 | 596.3 |
| 2174 | piperidin-1-yl-CH₂– | O | isobutyl | trans-4-methylcyclohexyl | 5.0 | 562.3 |
| 2175 | morpholin-4-yl-CH₂– | O | isobutyl | 4-bromo-2-fluorophenyl | 4.8 | 640.1 |

TABLE 2-continued
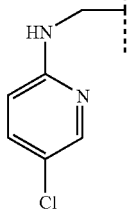
| Cpd | R²³ | X | R⁵ | R⁶ | t_R (min) | MS (M + H)⁺ |
|---|---|---|---|---|---|---|
| 2176 | 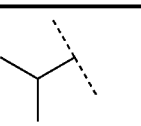 | O | 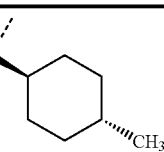 | 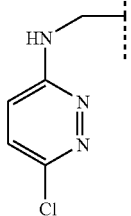 | 6.8 | 605.2 |
| 2177 | 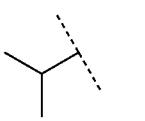 | O | 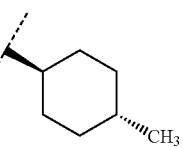 | 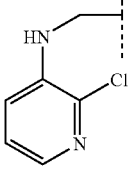 | 6.7 | 606.2 |
| 2178 | 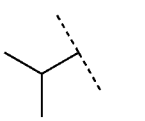 | O | 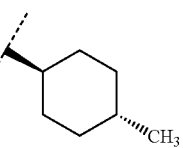 | 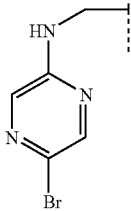 | 7.6 | 605.2 |
| 2179 | 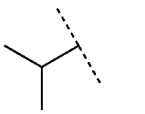 | O | 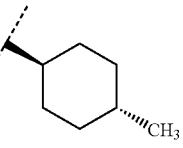 | 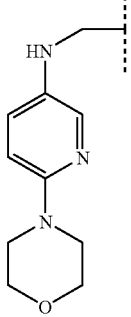 | 7.9 | 650.2 |
| 2180 | 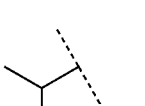 | O | 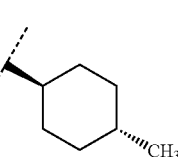 |  | 5.9 | 656.3 |

TABLE 2-continued

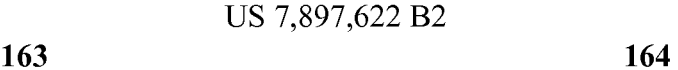

| Cpd | R²³ | X | R⁵ | R⁶ | t_R (min) | MS (M + H)⁺ |
|---|---|---|---|---|---|---|
| 2181 | 1,2,4-triazol-1-ylmethyl | O | isobutyl | trans-4-methylcyclohexyl | 5.6 | 546.3 |
| 2182 | (6-ethylpyridin-2-yl)aminomethyl | O | isobutyl | trans-4-methylcyclohexyl | 6.2 | 599.3 |
| 2183 | (4-aminopyridinium-1-yl)methyl | O | isobutyl | trans-4-methylcyclohexyl | 5.7 | 571.3 |
| 2184 | (pyrimidin-2-yl)aminomethyl | O | isobutyl | trans-4-methylcyclohexyl | 6.2 | 572.3 |
| 2185 | (3-imino-5,6-dimethyl-1,2,4-triazin-4-yl)methyl | O | isobutyl | trans-4-methylcyclohexyl | 5.8 | 601.3 |
| 2186 | (N-methyl-N-methoxycarbonylamino)methyl | O | isobutyl | trans-4-methylcyclohexyl | 7.2 | 565.2 |

TABLE 2-continued

| Cpd | R²³ | X | R⁵ | R⁶ | $t_R$ (min) | MS (M + H)⁺ |
|---|---|---|---|---|---|---|
| 2187 | H₃C-N(Et)-CH₂- with OC(O)OCH₃ | O | isobutyl | trans-4-methylcyclohexyl | 7.5 | 579.3 |
| 2188 | H₃C-N(Me)-CH₂- with OC(O)OCH₂CH₃ | O | isobutyl | trans-4-methylcyclohexyl | 7.5 | 579.3 |
| 2189 | H₃C-N(Et)-CH₂- with OC(O)OCH₂CH₃ | O | isobutyl | trans-4-methylcyclohexyl | 7.8 | 593.3 |
| 2190 | 6-chloropyridin-3-yl-NH-CH₂- | O | isobutyl | trans-4-methylcyclohexyl | 7.5 | 605.2 |
| 2191 | 5-imino-1,3,4-thiadiazol-4-yl-CH₂- | O | isobutyl | trans-4-methylcyclohexyl | 5.6 | 578.2 |
| 2192 | 2-methylquinolin-4-yl-NH-CH₂- | O | isobutyl | trans-4-methylcyclohexyl | 6.3 | 635.2 |

TABLE 2-continued

| Cpd | R²³ | X | R⁵ | R⁶ | t_R (min) | MS (M + H)⁺ |
|---|---|---|---|---|---|---|
| 2193 | 3-methylpyrazol-1-ylmethyl | O | isobutyl | trans-4-methylcyclohexyl | 7.0 | 559.2 |
| 2194 | (3-oxopiperazin-1-yl)methyl | O | isobutyl | trans-4-methylcyclohexyl | 4.8 | 577.3 |
| 2195 | H | O | isobutyl | 2-fluoro-4-bromophenylmethyl | 6.1 | 543.0 |
| 2196 | H | O | isobutyl | 3-methyl-4-chlorophenylmethyl | 6.1 | 493.1 |
| 2197 | (5-amino-1,2,4-triazol-1-yl)methyl | O | isobutyl | trans-4-methylcyclohexyl | 5.0 | 561.2 |
| 2198 | (3-amino-1,2,4-triazol-1-yl)methyl | O | isobutyl | trans-4-methylcyclohexyl | 5.3 | 561.2 |
| 2199 | (2-aminothiazol-3-ium-3-yl)methyl | O | isobutyl | trans-4-methylcyclohexyl | 5.0 | 577.2 |

TABLE 2-continued

| Cpd | R²³ | X | R⁵ | R⁶ | $t_R$ (min) | MS (M + H)⁺ |
|---|---|---|---|---|---|---|
| 2200 | 2-(pyridinyl)NH-CH₂- | O | isobutyl | trans-4-methylcyclohexyl | 5.0 | 571.2 |
| 2201 | (6-methoxypyrimidin-4-yl)NH-CH₂- | O | isobutyl | trans-4-methylcyclohexyl | 5.6 | 602.2 |
| 2202 | (5-amino-3-methyl-1,2,4-triazol-1-yl)-CH₂- | O | isobutyl | trans-4-methylcyclohexyl | 5.1 | 575.2 |
| 2203 | (5-oxo-pyrazolidin-1-yl)-CH₂- | O | isobutyl | trans-4-methylcyclohexyl | 5.6 | 563.2 |
| 2204 | (5-methyltetrazol-1-yl)-CH₂- | O | isobutyl | trans-4-methylcyclohexyl | 6.1 | 561.1 |
| 2205 | (imidazo[4,5-c]pyridin-1-yl)- | O | isobutyl | trans-4-methylcyclohexyl | 5.1 | 596.2 |

The invention claimed is:

1. A compound of formula (I):

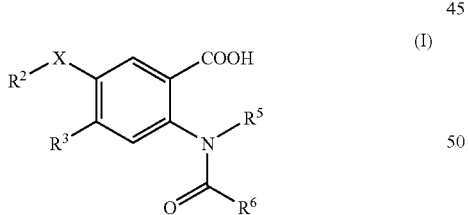

(I)

wherein:

X is selected from O and S;

$R^2$ is pyridine, optionally substituted with 1 to 5 $R^{20}$ substituents, wherein $R^{20}$ in each case is independently selected from:

a) halo, cyano or nitro;

b) $R^7$, —C(=O)—$R^7$, —C(=O)—O—$R^7$, —O—$R^7$, —S—$R^7$, —SO—$R^7$, —SO$_2$—$R^7$, —($C_{1-6}$)alkylene-$R^7$, —($C_{1-6}$)alkylene-C(=O)—$R^7$, —($C_{1-6}$)alkylene-C(=O)—O—$R^7$, —($C_{1-6}$)alkylene-O—$R^7$, —($C_{1-6}$)alkylene-S—$R^7$, —($C_{1-6}$)alkylene-SO—$R^7$ or —($C_{1-6}$)alkylene-SO$_2$—$R^7$;

wherein $R^7$ is in each instance independently selected from H, ($C_{1-6}$)alkyl, ($C_{2-6}$)alkenyl, ($C_{2-6}$)alkynyl, ($C_{1-6}$)haloalkyl, ($C_{3-7}$)cycloalkyl, aryl and Het;

wherein the ($C_{1-6}$)alkyl is optionally substituted with 1 or 2 substituents each independently selected from —OH, —O—($C_{1-6}$)alkyl, cyano, COOH, —NH$_2$, —NH($C_{1-4}$)alkyl, —NH($C_{3-7}$)cycloalkyl, —N(($C_{1-4}$)alkyl)($C_{3-7}$)cycloalkyl and —N(($C_{1-4}$)alkyl)$_2$; and wherein each of the aryl and Het is optionally substituted with 1 to 3 substituents each independently selected from:

i) halo, cyano, oxo, thioxo, imino, —OH, —O—($C_{1-6}$)alkyl, —O—($C_{1-6}$)haloalkyl, ($C_{3-7}$)cycloalkyl, ($C_{1-6}$)haloalkyl, —C(=O)—($C_{1-6}$)alkyl, —SO$_2$($C_{1-6}$)alkyl, —C(=O)—NH$_2$, —C(=O)—NH($C_{1-4}$)alkyl, —C(=O)—N(($C_{1-4}$)alkyl)$_2$, —C(=O)—NH($C_{3-7}$)cycloalkyl, —C(=O)—N(($C_{1-4}$)alkyl)($C_{3-7}$)cycloalkyl, —NH$_2$, —NH($C_{1-4}$)alkyl, —N(($C_{1-4}$)alkyl)$_2$, —NH($C_{3-7}$)cycloalkyl, —N(($C_{1-4}$)alkyl)($C_{3-7}$)cycloalkyl or —NH—C(=O)($C_{1-4}$)alkyl;

ii) ($C_{1-6}$)alkyl optionally substituted with —OH, —O—($C_{1-6}$)haloalkyl, or —O—($C_{1-6}$)alkyl; and iii) aryl or Het, wherein each of the aryl and Het is optionally substituted with halo or $(C_{1-6})$alkyl; and c) $-N(R^8)R^9$, $-C(=O)-N(R^8)R^9$, $-O-C(=O)-N(R^8)R^9$, $-SO_2-N(R^8)R^9$, $-(C_{1-6})$alkylene-$N(R^8)R^9$, $-(C_{1-6})$alkylene-$C(=O)-N(R^8)R^9$, $-(C_{1-6})$alkylene-$O-C(=O)-N(R^8)R^9$, or $-(C_{1-6})$alkylene-$SO_2-N(R^8)R^9$ wherein $R^8$ is in each instance independently selected from H, $(C_{1-6})$alkyl and $(C_{3-7})$cycloalkyl; and $R^9$ is in each instance independently selected from $R^7$, $-(C_{1-6})$alkylene-$R^7$, $-SO_2-R^7$, $-C(=O)-R^7$, $-C(=O)OR^7$ and $-C(=O)N(R^8)R^7$;

wherein $R^7$ and $R^8$ are as defined above;

$R^3$ is selected from H, halo, $(C_{1-4})$alkyl, $-O-(C_{1-4})$alkyl, $-S-(C_{1-4})$alkyl, $-NH_2$, $-NH(C_{1-4})$alkyl, $-NH(C_{3-7})$cycloalkyl, $-N((C_{1-4})$alkyl)$(C_{3-7})$cycloalkyl and $-N((C_{1-4})$alkyl)$_2$;

$R^5$ is H, $(C_{1-6})$alkyl, $(C_{3-7})$cycloalkyl or Het; the $(C_{1-6})$alkyl and Het each being optionally substituted with 1 to 4 substituents each independently selected from $(C_{1-6})$alkyl, Het, $-OH$, $-COOH$, $-C(=O)-(C_{1-6})$alkyl, $-C(=O)-O-(C_{1-6})$alkyl, $-SO_2(C_{1-6})$alkyl and $-C(=O)-N(R^{51})R^{52}$;

wherein $R^{51}$ is H, $(C_{1-6})$alkyl or $(C_{3-7})$cycloalkyl; and $R^{52}$ is H, $(C_{1-6})$alkyl, $(C_{3-7})$cycloalkyl, aryl, Het, aryl-$(C_{1-3})$alkyl- or Het-$(C_{1-3})$alkyl-; wherein each of the $(C_{1-6})$alkyl, $(C_{3-7})$cycloalkyl, aryl, Het, aryl-$(C_{1-3})$alkyl- and Het-$(C_{1-3})$alkyl- are optionally substituted with 1 to 3 substituents each independently selected from $(C_{1-6})$alkyl, $(C_{1-6})$haloalkyl, halo, oxo, $-OH$, $-O(C_{1-6})$alkyl, $-NH_2$, $-NH(C_{1-6})$alkyl, $-N((C_{1-6})$alkyl)$_2$, $-NH(C_{3-7})$cycloalkyl, $-N((C_{1-4})$alkyl)$(C_{3-7})$cycloalkyl, $-C(=O)(C_{1-6})$alkyl and $-NHC(=O)-(C_{1-6})$alkyl;

wherein the $(C_{1-6})$alkyl is optionally substituted with OH;

or $R^{51}$ and $R^{52}$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or $SO_2$;

wherein the heterocycle is optionally substituted with 1 to 3 substituents each independently selected from $(C_{1-6})$alkyl, $(C_{1-6})$haloalkyl, halo, oxo, $-OH$, $-O(C_{1-6})$alkyl, $-NH_2$, $-NH(C_{1-6})$alkyl, $-N((C_{1-6})$alkyl)$_2$, $-NH(C_{3-7})$cycloalkyl, $-N((C_{1-4})$alkyl)$(C_{3-7})$cycloalkyl, $-C(=O)(C_{1-6})$alkyl and $-NHC(=O)-(C_{1-6})$alkyl;

wherein the $(C_{1-6})$alkyl is optionally substituted with OH;

$R^6$ is $(C_{3-7})$cycloalkyl or aryl;

the $(C_{3-7})$cycloalkyl and aryl each being optionally substituted with 1 to 5 substituents each independently selected from halo, $(C_{1-6})$alkyl, $(C_{1-6})$haloalkyl, $(C_{3-7})$cycloalkyl, $-OH$, $-SH$, $-O-(C_{1-4})$alkyl and $-S-(C_{1-4})$alkyl; and Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$;

provided that when $R^2$ is selected from:

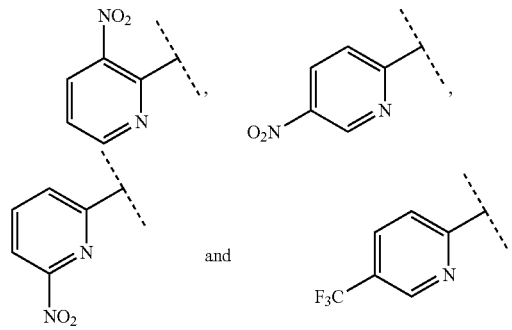

$X$ is O; $R^3$ is H; and $R^5$ is H; then $R^6$ is not

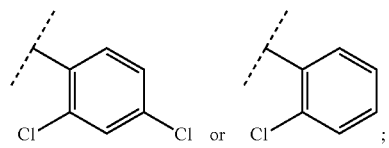

or a salt or ester thereof.

2. A compound according to claim 1 wherein X is O.
3. A compound according to claim 1 wherein X is S.
4. A compound according to claim 1 wherein $R^2$ is

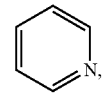

optionally substituted with 1 to 3 $R^{20}$ substituents, wherein $R^{20}$ is as defined in claim 1.

5. A compound according to claim 4 wherein $R^2$ is Het of the formula:

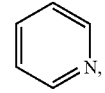

optionally substituted with 1 to 3 $R^{20}$ substituents;

wherein $R^{20}$ is selected from:

a) halo or cyano;

b) $R^7$, $-(C_{1-6})$alkylene-$R^7$, $-C(=O)-R^7$, $-(C_{1-6})$alkylene-$O-R^7$, $-SO_2-R^7$, $-(C_{1-6})$alkylene-$S-R^7$ or $-(C_{1-6})$alkylene-$SO_2-R^7$;

wherein $R^7$ is in each instance independently selected from H, $(C_{1-6})$alkyl, $(C_{2-6})$alkenyl, $(C_{1-6})$haloalkyl, $(C_{3-7})$cycloalkyl, aryl and Het; wherein the Het is a 5- or 6-membered heterocycle containing 1 to 4 heteroatoms, each independently selected from N, O and S, or Het is a 9- or 10-membered heteropolycycle containing 1 to 4 heteroatoms, each independently selected from N, O and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$; and wherein the $(C_{1-6})$alkyl is optionally substituted with 1 or 2 substituents each independently selected from —OH, —O—$(C_{1-6})$alkyl and COOH; and wherein each of the aryl and Het is optionally substituted with 1 to 3 substituents each independently selected from halo, cyano, oxo, imino, —OH, —O—$(C_{1-6})$alkyl, —$NH_2$, —NH$(C_{1-4})$alkyl, —N$((C_{1-4})$alkyl$)_2$, —NH—C(=O)$(C_{1-4})$alkyl, $(C_{1-6})$alkyl and Het, wherein the Het is a 5- or 6-membered heterocycle containing 1 to 4 heteroatoms, each independently selected from N, O and S; and c) —$(C_{1-6})$alkylene-N($R^8$)$R^9$ or —$(C_{1-6})$alkylene-C(=O)—N($R^8$)$R^9$ wherein $R^8$ is in each instance independently selected from H and $(C_{1-6})$alkyl; and $R^9$ is in each instance independently selected from $R^7$, —$SO_2$—$R^7$, —C(=O)—$R^7$, —C(=O)O$R^7$ and —C(=O)N($R^8$)$R^7$; wherein $R^7$ and $R^8$ are as defined above.

6. A compound according to claim 1 wherein $R^2$ is a group of the formula:

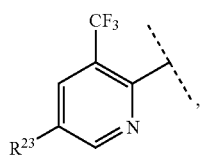

wherein $R^{23}$ is $R^{20}$; and
$R^{20}$ is as defined in claim 1.

7. A compound according to claim 5 wherein $R^2$ is a group of the formula:

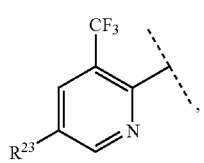

wherein $R^{23}$ is $R^{20}$; and
$R^{20}$ is selected from:

a) halo or cyano;

b) $R^7$, —$CH_2$—$R^7$, —C(=O)—$R^7$, —$CH_2$—O—$R^7$, —$SO_2$—$R^7$, —$CH_2$—S—$R^7$ or —$CH_2$—$SO_2$—$R^7$;

wherein $R^7$ is in each instance independently selected from H, $(C_{1-6})$alkyl, $(C_{2-6})$alkenyl, $(C_{1-6})$haloalkyl, $(C_{3-7})$cycloalkyl, phenyl and Het; wherein the Het is selected from:

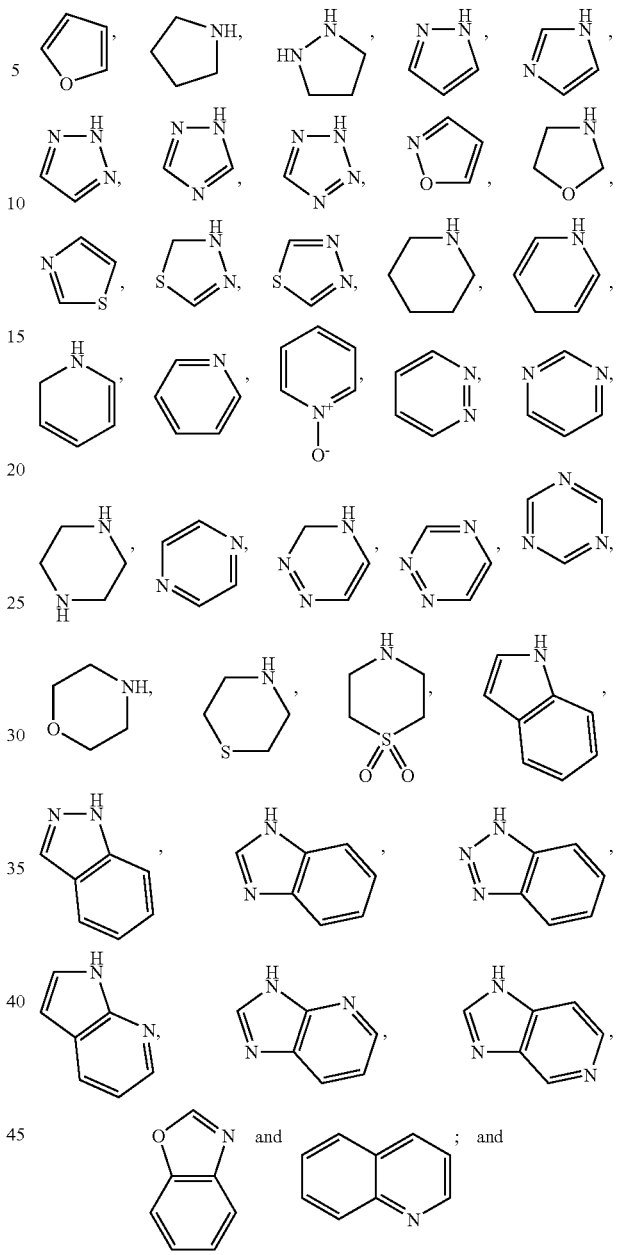

wherein the $(C_{1-6})$alkyl is optionally substituted with 1 or 2 substituents each independently selected from —OH, —O—$(C_{1-6})$alkyl and COOH; and wherein each of the phenyl and Het is optionally substituted with 1 to 3 substituents each independently selected from halo, cyano, oxo, imino, —OH, —O—$(C_{1-6})$alkyl, —$NH_2$, —NH$(C_{1-4})$alkyl, —N$((C_{1-4})$alkyl$)_2$, —NH—C(=O)$(C_{1-4})$alkyl, $(C_{1-6})$alkyl and

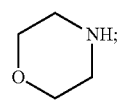

and c) —CH$_2$—N(R$^8$)R$^9$ or —CH$_2$—C(=O)—N(R$^8$)R$^9$
wherein
R$^8$ is in each instance independently selected from H and (C$_{1-6}$)alkyl; and
R$^9$ is in each instance independently selected from R$^7$, —SO$_2$—R$^7$, —C(=O)—R$^7$, —C(=O)OR$^7$ and —C(=O)N(R$^8$)R$^7$; wherein R$^7$ and R$^8$ are as defined above.

8. A compound according to claim 6 wherein R$^2$ is a group of the formula:

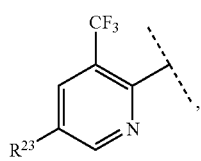

wherein R$^{23}$ is R$^{20}$; and
R$^{20}$ is selected from:

b) —CH$_2$—R$^7$, —CH$_2$CH$_2$—R$^7$, —CH$_2$—O—R$^7$, —CH$_2$—S—R$^7$ or —CH$_2$—SO$_2$—R$^7$;
wherein R$^7$ is Het; wherein the Het is selected from:

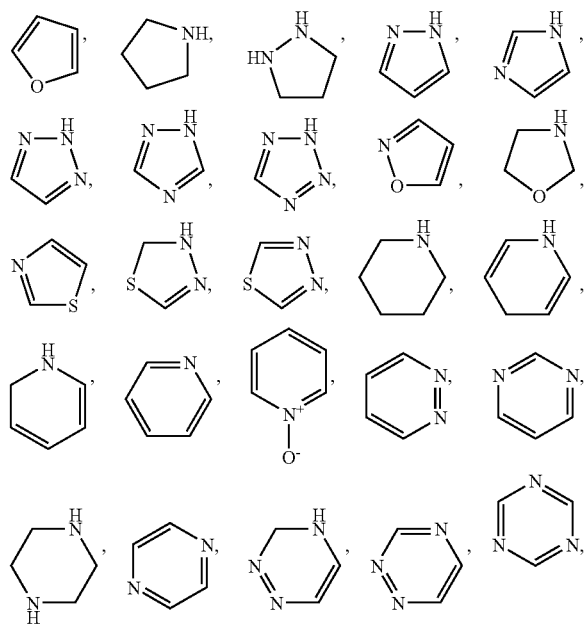

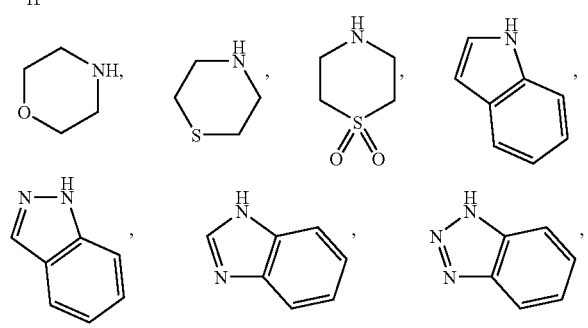

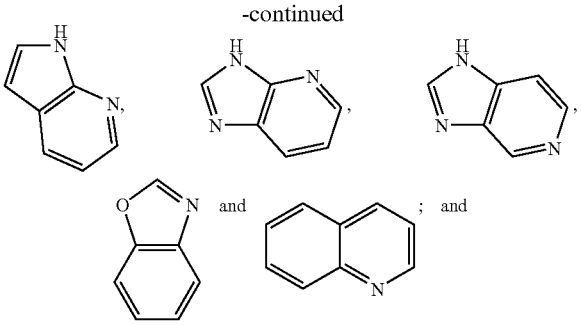

wherein the Het is optionally substituted with 1 to 3 substituents each independently selected from halo, cyano, oxo, imino, —OH, —O—(C$_{1-6}$)alkyl, —NH$_2$, —NH(C$_{1-4}$)alkyl, —N((C$_{1-4}$)alkyl)$_2$, —NH—C(=O)(C$_{1-4}$)alkyl, (C$_{1-6}$)alkyl and

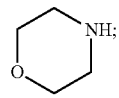

and c) —CH$_2$—N(R$^8$)R$^9$ wherein
R$^8$ is in each instance independently selected from H and (C$_{1-6}$)alkyl; and
R$^9$ is R$^7$ wherein R$^7$ is as defined above.

9. A compound according to claim 1 wherein R$^3$ is selected from H and halo.

10. A compound according to claim 9 wherein R$^3$ is H.

11. A compound according to claim 1 wherein R$^5$ is (C$_{1-6}$)alkyl.

12. A compound according to claim 11 wherein R$^5$ is 1-methylethyl.

13. A compound according to claim 1 wherein R$^5$ is (C$_{1-4}$)alkyl substituted with Het, —COOH or —C(=O)—N(R$^{51}$)R$^{52}$, wherein the Het is a 5- or 6-membered heterocycle containing from 1 to 4 N heteroatoms or Het is a 9- or 10-membered bicyclic heteropolycycle containing from 1 to 4 N heteroatoms;

and wherein R$^{51}$ is H or (C$_{1-6}$)alkyl and R$^{52}$ is selected from H, (C$_{1-6}$)alkyl, (C$_{3-7}$)cycloalkyl, Het and Het-(C$_{1-3}$)alkyl-;

wherein the (C$_{1-6}$)alkyl is optionally substituted with 1 or 2 substituents each independently selected from —O(C$_{1-6}$)alkyl and —N((C$_{1-6}$)alkyl)$_2$; and wherein the Het and the Het portion of Het-(C$_{1-3}$)alkyl- are each independently a 5- or 6-membered heterocycle containing 1 to 3 heteroatoms each independently selected from N, O and S, wherein the Het and the Het-(C$_{1-3}$)alkyl- are each optionally substituted with 1 to 3 substituents each independently selected from halo, oxo, —OH, (C$_{1-6}$)alkyl, (C$_{1-6}$)haloalkyl, —(C=O)(C$_{1-6}$)alkyl, —N((C$_{1-6}$)alkyl)$_2$ and —NH(C=O)(C$_{1-6}$)alkyl, wherein the (C$_{1-6}$)alkyl is optionally substituted with OH;

or R$^{51}$ and R$^{52}$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or $SO_2$;

wherein the heterocycle is optionally substituted with 1 to 3 substituents each independently selected from halo, oxo, —OH, $(C_{1-6})$alkyl, $(C_{1-6})$haloalkyl, —(C=O)$(C_{1-6})$alkyl, —N$((C_{1-6})$alkyl$)_2$ and —NH(C=O)$(C_{1-6})$alkyl, wherein the $(C_{1-6})$alkyl is optionally substituted with OH.

14. A compound according to claim 1 wherein $R^6$ is $(C_{3-7})$cycloalkyl optionally substituted with 1 to 5 substituents each independently selected from halo, $(C_{1-6})$alkyl, $(C_{1-6})$haloalkyl, $(C_{3-7})$cycloalkyl, —OH, —SH, —O—$(C_{1-4})$alkyl and —S—$(C_{1-4})$alkyl.

15. A compound according to claim 14 wherein $R^6$ is

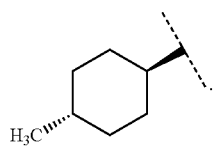

16. A compound according to claim 1 wherein $R^6$ is aryl optionally substituted with 1 to 5 substituents each independently selected from halo, $(C_{1-6})$alkyl, $(C_{1-6})$haloalkyl, $(C_{3-7})$cycloalkyl, —OH, —SH, —O—$(C_{1-4})$alkyl and —S—$(C_{1-4})$alkyl;

provided that when $R^2$ is selected from:

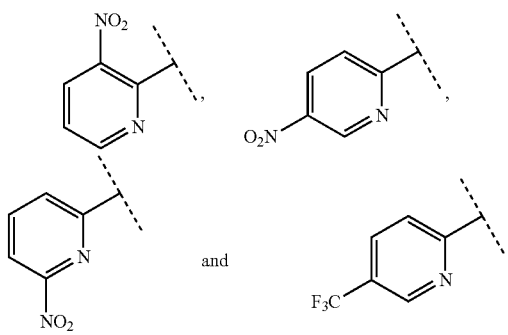

X is O; $R^3$ is H; and $R^5$ is H;
then $R^6$ is not

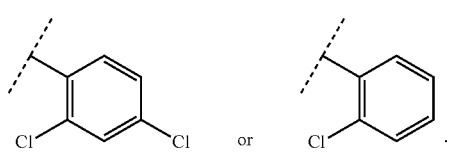

17. A compound according to claim 16 wherein $R^6$ is phenyl optionally substituted with 1 to 3 substituents each independently selected from halo, $(C_{1-4})$alkyl, $(C_{3-7})$cycloalkyl and —S—$(C_{1-4})$alkyl;

provided that when $R^2$ is selected from:

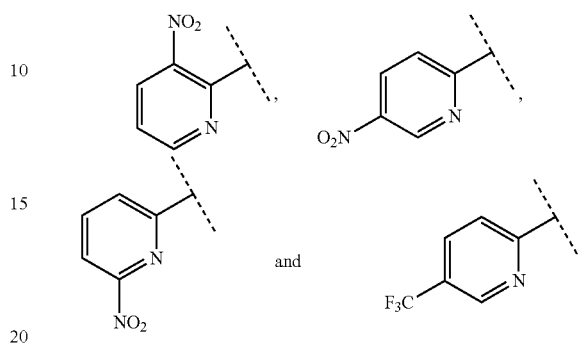

X is O; $R^3$ is H; and $R^5$ is H;
then $R^6$ is not

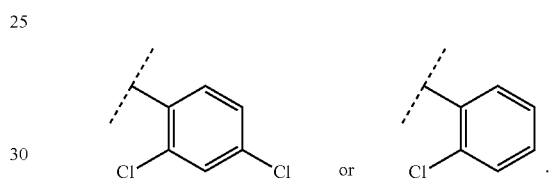

18. A compound according to claim 1, or a pharmaceutically acceptable salt or ester thereof; as a medicament.

19. A pharmaceutical composition comprising a therapeutically effective amount of a compound according to claim 1, or a pharmaceutically acceptable salt or ester thereof; and one or more pharmaceutically acceptable carriers.

20. The pharmaceutical composition according to claim 19 additionally comprising at least one other antiviral agent.

21. A method of treating a hepatitis C viral infection in a mammal having or at risk of having the infection, the method comprising administering to the mammal a therapeutically effective amount of a compound according to claim 1, a pharmaceutically acceptable salt or ester thereof, or a composition thereof.

22. A method of treating a hepatitis C viral infection in a mammal having or at risk of having the infection, the method comprising administering to the mammal a therapeutically effective amount of a combination of a compound according to claim 1 or a pharmaceutically acceptable salt or ester thereof, and at least one other antiviral agent; or a composition thereof.

* * * * *